United States Patent
Aldaz et al.

(10) Patent No.: US 9,328,173 B2
(45) Date of Patent: May 3, 2016

(54) MULTIFUNCTIONAL ANTIBODIES BINDING TO EGFR AND MET

(71) Applicant: Eli Lilly and Company, Indianapolis, IN (US)

(72) Inventors: Hector Aldaz, San Marcos, CA (US); Barrett Allan, Encinitas, CA (US); Ling Liu, Carmel, IN (US); Jirong Lu, Carmel, IN (US); Ying Tang, San Diego, CA (US); Sheng-Hung Rainbow Tschang, Carmel, IN (US); Pia Pauliina Yachi, San Diego, CA (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 14/573,373

(22) Filed: Dec. 17, 2014

(65) Prior Publication Data

US 2015/0175708 A1 Jun. 25, 2015

Related U.S. Application Data

(60) Provisional application No. 61/920,097, filed on Dec. 23, 2013.

(51) Int. Cl.
| | |
|---|---|
| C07K 16/40 | (2006.01) |
| C07K 16/28 | (2006.01) |
| C07K 16/30 | (2006.01) |
| A61K 39/00 | (2006.01) |

(52) U.S. Cl.
CPC ............ *C07K 16/40* (2013.01); *C07K 16/2863* (2013.01); *C07K 16/30* (2013.01); *C07K 16/3023* (2013.01); *C07K 16/3046* (2013.01); *A61K 2039/505* (2013.01); *C07K 2317/31* (2013.01); *C07K 2317/60* (2013.01); *C07K 2317/622* (2013.01); *C07K 2317/73* (2013.01); *C07K 2317/77* (2013.01); *C07K 2317/92* (2013.01)

(58) Field of Classification Search
CPC ........... C07K 16/2863; C07K 2317/60; C07K 2317/31
USPC ....................... 424/136.1; 435/328; 530/387.3
See application file for complete search history.

(56) References Cited

U.S. PATENT DOCUMENTS

| | | | |
|---|---|---|---|
| 7,723,484 | B2 | 5/2010 | Beidler et al. |
| 8,124,085 | B2 | 2/2012 | Nielsen et al. |
| 2009/0226443 | A1 | 9/2009 | Filvaroff et al. |
| 2012/0238728 | A1 | 9/2012 | Miller et al. |
| 2014/0294830 | A1 | 10/2014 | Lee et al. |
| 2014/0302029 | A1 | 10/2014 | Cho et al. |

FOREIGN PATENT DOCUMENTS

| | | |
|---|---|---|
| WO | WO 95/09917 A1 | 4/1995 |
| WO | WO 01/77342 A1 | 10/2001 |
| WO | WO 2009/068649 A2 | 6/2009 |
| WO | WO 2009/126834 A2 | 10/2009 |
| WO | WO 2010/039248 A1 | 4/2010 |
| WO | WO 2010/059654 A1 | 5/2010 |
| WO | WO 2010/084197 A1 | 6/2010 |
| WO | WO 2010/115551 A1 | 10/2010 |
| WO | WO 2010/136172 A1 | 12/2010 |
| WO | WO 2013/033008 A9 | 3/2013 |

OTHER PUBLICATIONS

Kobold et al. JNCI 107(1):1-8 (2015).*
Jarantow et al. JBC 29(41):24689-24704 (Oct. 9, 2015).*
Spiess et al Nature Biotech 31(8):753-759 (Aug. 2013).*
Castoldi, R., et al., "A novel bispecific EGFR/Met antibody blocks tumor-promoting phenotypic effects induced by resistance to EGFR inhibition and has potent antitumor activity," Oncogene; 32, pp. 5593-5601 (2013).
Xu, H., et al., "Dual Blockade of EGFR and c-Met Abrogates Redundant Signaling and Proliferation in Head and Neck Carcinoma Cells," Clinical Cancer Research; 17, pp. 4425-4438 (2011).
Engelman, J.A., et al., "MET amplification leads to gefitinib resistance in lung cancer by activating ERBB3 signaling," Science; 316, pp. 1039-1043 (2007).
McDermott, U., et al., "Acquired resistance of non-small cell lung cancer cells to MET kinase inhibition is mediated by a switch to epidermal growth factor receptor dependency," Cancer Res.; 70(4), pp. 1625-1634 (2010).
Spigel, D.R., et al., "Randomized Phase II Trial of Onartuzumab in Combination With Erlotinib in Patients With Advanced Non-Small-Cell Lung Cancer," J. Clinical Oncology; 31(32), pp. 4105-4114 (Nov. 2013).
Xiang H., et al., "Onartuzumab (MetMAb): Using Nonclinical Pharmacokinetic and Concentration—Effect Data to Support Clinical Development," Clin Cancer Res.; 19, pp. 5068-5078 (2013).
Zeng, W., et al., LY2875358, a bivalent antibody with anti-tumor activity through blocking HGF as well as inducing degradation of MET, differentiates from a one-armed 5D5 MET antibody, 104th AACR Annual Meeting, poster #5465 (Apr. 2013).
Dimasi, N., "The Design and Characterization of Oligospecific Antibodies for Simultaneous Targeting of Multiple Disease Mediators," J. Mol. Biol.; 393, pp. 672-692 (2009).
Moores, S., "Bispecific Antibody Targeting EGFR and cMet Demonstrates Superior Activity Compared to the Combination of Single Pathway Inhibitors Proceedings of the AACR-NCI-EORTC International Conference: Molecular Targets and Cancer Therapeutics," Boston, MA; Oct. 19-23, 2013.
Spiess, C., et al., "Bispecific antibodies with natural architecture produced by co-culture of bacteria expressing two distinct half-antibodies," Nature Biotechnology; 31(8), pp. 753-758 (Aug. 2013).

* cited by examiner

*Primary Examiner* — Lynn Bristol
(74) *Attorney, Agent, or Firm* — Robert L. Sharp

(57) ABSTRACT

Provided are multifunctional antibodies, and/or antigen-binding fragments, that bind to, and inhibit the activity of, both human epidermal growth factor receptor (EGFR) and MET, and that are effective in treating cancers and other diseases, disorders, or conditions where pathogenesis is mediated by EGFR and MET.

8 Claims, 7 Drawing Sheets

Lane 1: hIgG4; Lane 2: anti-MET Ab; Lane 3: cetuximab;
Lane 4 anti-MET Ab + cetuximab; Lane 5: NH-YK; Lane 6: NH-H9

Y-axis of graph = Tumor Volume (mm3), Mean ± Standard Error
X-axis of graph = Days Post Implantation

Key:
——————— Vehicle control
— — — — — 20 mpk cetuximab + 20 mpk anti-MET Ab
· · · · · · · · · 27 mpk NH-YK Y-axis of graph = Tumor Volume (mm$^3$), Mean ± Standard Error
X-axis of graph = Days Post Implantation Key:
——————— Vehicle control
— — — — 20 mpk cetuximab + 20 mpk anti-MET Ab
- - - - - - - 27 mpk NH-YK Y-axis of graph = Tumor Volume (mm3), Mean ± Standard Error
X-axis of graph = Days Post Implantation

Key:
──────── Vehicle control
- - - - - - 10 mpk NH-YK

Y-axis of graph = Tumor Volume (mm$^3$), Mean ± Standard Error
X-axis of graph = Days Post Implantation

Key:
——————— vehicle control
— — — — — 20 mpk cetuximab + 20 mpk anti-MET Ab
- - - - - - - - 27 mpk NH-YK

Fig. 6

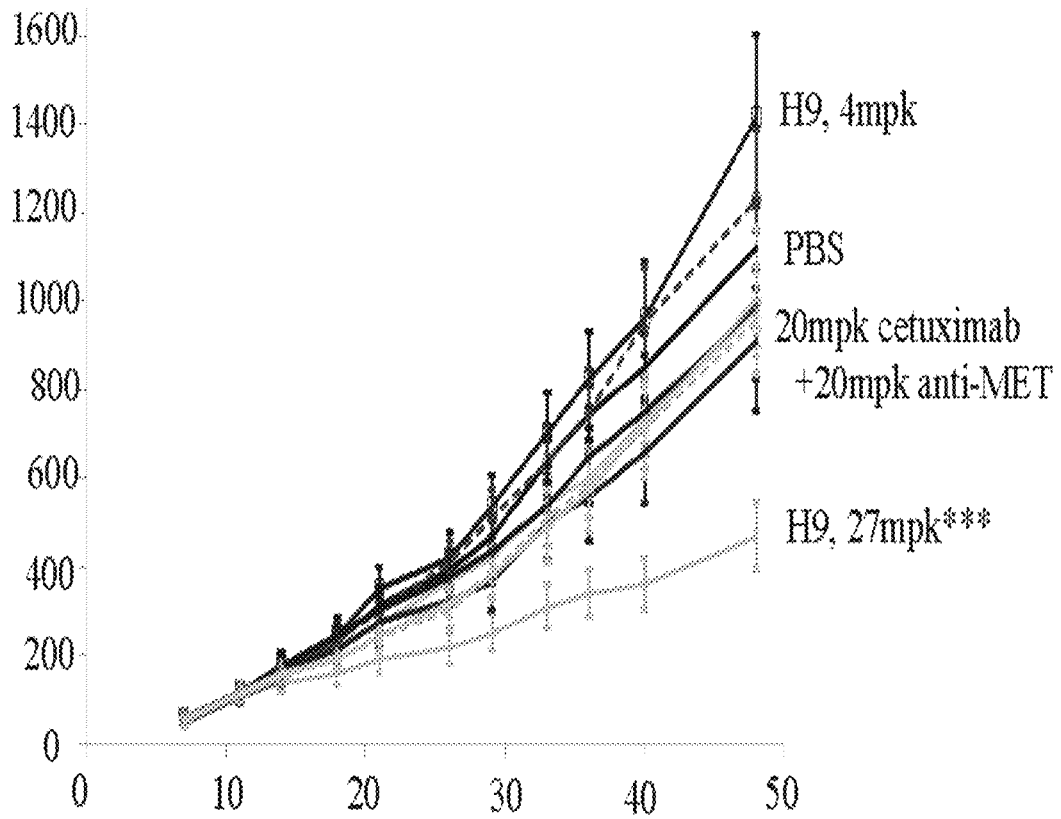

Y-axis of graph = Tumor Volume (mm3), Mean ± St. Err., Method = (LogVol,SP)
X-axis of graph = Days Post Implantation Key:

- PBS, 0.2 ml, IV, q7d x 5
- H9, 4 mg/kg, IV, q7d x 5
- H9, 27 mg/kg, IV, q7d x 5
- anti-MET, 3 mg/kg, IV, q7d x 5
- cetuximab, 3 mg/kg, IV, q7d x 5
- <n cetuximab, 3 mg/kg, IV, q7d x 5
- anti-MET, 3 mg/kg, IV, q7d x 5 / cetuximab, 3 mg/kg, IV, q7d x 5
- anti-MET, 20 mg/kg, IV, q7d x 5
- cetuximab, 20 mg/kg, IV, q7d x 5
- <n cetuximab, 20 mg/kg, IV, q7d x 5
- anti-MET, 20 mg/kg, IV, q7d x 5 / cetuximab, 20 mg/kg, IV, q7d x 5

Fig. 7

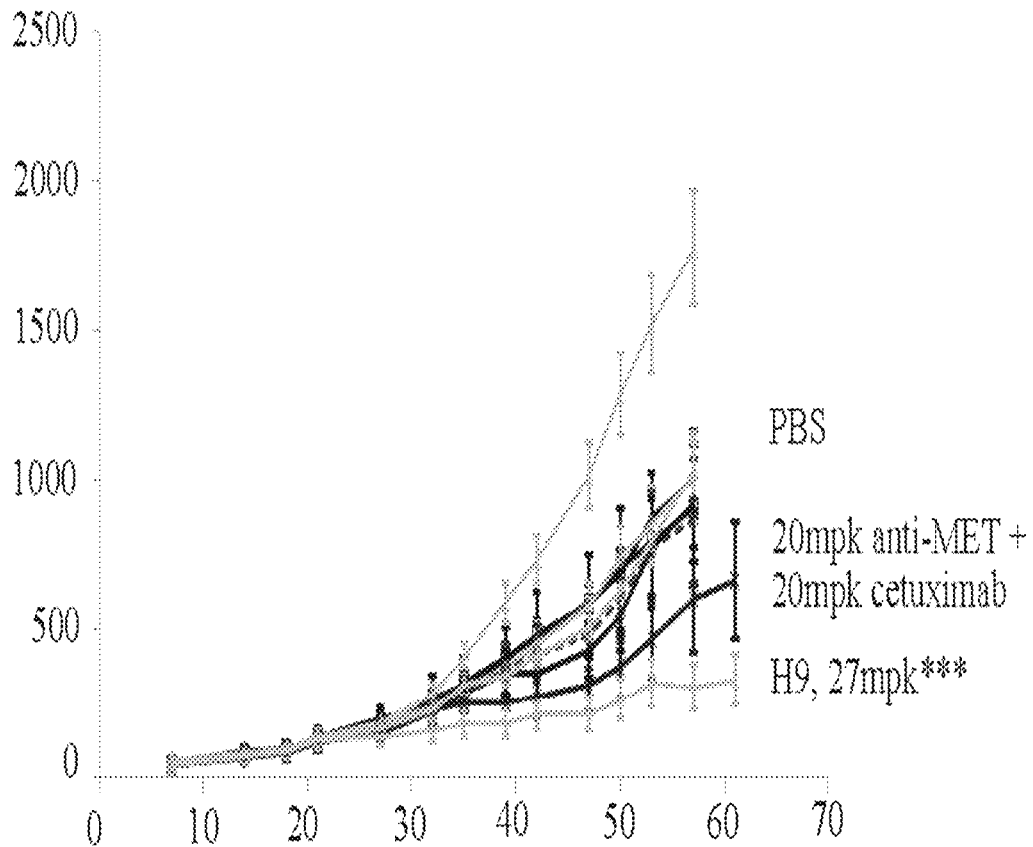

Y-axis of graph = Tumor Volume (mm$^3$), Mean ± St. Err., Method = (LogVol,SP)
X-axis of graph = Days Post Implantation

Key:

- PBS, 0.2 mL, IV, q7d x 5
- anti-MET, 0.6 mg/kg, IV, q7d x 5 / cetuximab, 0.6 mg/kg, IV, q7d x 5
- anti-MET, 3 mg/kg, IV, q7d x 5
- cetuximab, 3 mg/kg, IV, q7d x 5
- anti-MET, 3 mg/kg, IV, q7d x 5 / cetuximab, 3 mg/kg, IV, q7d x 5
- <n anti-MET, 3 mg/kg, IV, q7d x 5 / cetuximab, 3 mg/kg, IV, q7d x 5
- anti-MET, 20 mg/kg, IV, q7d x 5 / cetuximab, 20 mg/kg, IV, q7d x 5
- H9, 0.8 mg/kg, IV, q7d x 5
- H9, 4 mg/kg, IV, q7d x 5
- H9, 27 mg/kg, IV, q7d x 5

MULTIFUNCTIONAL ANTIBODIES BINDING TO EGFR AND MET

The present invention relates to multifunctional antibodies that bind to human epidermal growth factor receptor (EGFR) and MET, methods for their production, pharmaceutical compositions containing the multifunctional antibodies, and uses thereof.

EGFR is a member of the type 1 tyrosine kinase family of growth factor receptors, which plays critical roles in cellular growth, differentiation, and survival. Activation of these receptors typically occurs via specific ligand binding with subsequent autophosphorylation of the tyrosine kinase domain. This activation triggers a cascade of intracellular signaling pathways involved in both cellular proliferation and survival.

Various strategies of cancer therapy to target EGFR and block EGFR signaling pathways have been established. Small-molecule tyrosine kinase inhibitors, e.g., gefitinib and erlotinib, block autophosphorylation of EGFR in the intracellular tyrosine kinase region, thereby inhibiting downstream signaling events. One of the major challenges facing the clinical use of anti-EGFR tyrosine kinase inhibitors is the inherent and acquired resistance of cancers to this class of therapeutics. Certain therapeutic monoclonal antibodies (mAbs), on the other hand, target the extracellular portion of EGFR, which results in blocking ligand binding and thereby inhibits downstream events leading to the inhibition of cell proliferation. The chimeric mouse/human anti-EGFR monoclonal antibody C225 (or cetuximab), and panitumumab, a fully human anti-EGFR mAb, have been approved for treatment of metastatic colorectal and head and neck cancer which target the external part of EGFR. However, patients whose tumor contains a KRAS mutation often do not benefit from cetuximab or panitumumab therapy. KRAS mutations alter signaling properties in the tumor cells by continuously sending a growth signal even if EGFR has been blocked.

MET, a member of the tyrosine kinase superfamily, is the human receptor for human hepatocyte growth factor (HGF). Binding of HGF to MET leads to receptor dimerization or multimerization, phosphorylation of multiple tyrosine residues in the intracellular region, catalytic activation, and downstream signaling. MET is also activated via ligand-independent mechanisms, including receptor over-expression, amplification, and mutation. MET activation enhances cellular proliferation, migration, morphogenesis, and survival, which are associated with invasive cell phenotype and poor clinical outcomes. Thus, MET is also a target for anti-cancer therapy. For example, onartuzumab, also known in the art as one-armed 5D5, OA5D5 or MetMAb, has been developed for the potential treatment of cancer, and is a humanized, monovalent, antagonistic anti-MET antibody derived from the MET agonistic monoclonal antibody 5D5 (see, for example, Spigel, D. R., et al., Randomized Phase II Trial of Onartuzumab in Combination With Erlotinib in Patients With Advanced Non Small-Cell Lung Cancer, J. Clinical Oncology, 31(32):4105-4114 (November 2013) and Xiang H., et al., Onartuzumab (MetMAb): Using Nonclinical Pharmacokinetic and Concentration—Effect Data to Support Clinical Development, *Clin Cancer Res.*, (2013)). Onartuzumab binds to MET and remains on the cell surface with MET, preventing HGF binding and subsequent MET phosphorylation as well as downstream signaling activity and cellular responses.

WO 2010/059654 describes various MET antibodies including high-affinity antagonistic antibodies that bind to an epitope within the α-chain of MET and which induce internalization and/or degradation of MET in the presence or absence of HGF and in tumors characterized by gain of function mutations which are generally resistant to known MET antagonists. One of the MET antibodies disclosed in WO 2010/059654, LY2875358 has been reported to have no or otherwise negligible agonist activity on MET (see, for example, Zeng, W., et al., 104th AACR Annual Meeting, poster #5465 (2013)).

U.S. Pat. No. 7,723,484 describes humanized and affinity optimized EGFR specific antibodies, and antigen-binding portions thereof, that inhibit activation of EGFR. More specifically, this patent describes, inter alia, full-length monoclonal antibodies that bind to human epidermal growth factor receptor (EGFR) with subpicomolar binding affinities (Kd) as measured by a Sapidyne KINEXA performed at room temperature.

MET and EGFR are co-expressed in many tumors. Blocking one receptor tends to up-regulate the other, frequently and often quickly leading to resistance to single agent treatment (Engelman, J. A., et al. MET amplification leads to gefitinib resistance in lung cancer by activating ERBB3 signaling. *Science*, 316:1039-43 (2007)). Conversely, MET-amplified lung cancer cells exposed to MET-inhibiting agents for a prolonged period develop resistance via the EGFR pathway (McDermott, U., et al., Acquired resistance of non-small cell lung cancer cells to MET kinase inhibition is mediated by a switch to epidermal growth factor receptor dependency, *Cancer Res.*, 70(4):1625-34 (2010)). Co-administration of a MET antibody and an EGFR antibody requires injections of two separate products or a single injection of a co-formulation of two different antibodies. Two injections would permit flexibility of dose amount and timing, but would be inconvenient to patients both for compliance and pain. A co-formulation might also provide some flexibility of dose amounts, but it is often quite challenging or impossible to find formulation conditions that permit chemical and physical stability of both antibodies due to different molecular characteristics of the two different antibodies.

WO 199509917 discloses a method for producing bispecific, tetravalent antibodies using recombinant DNA technology by producing a single chain fragment variable (scFv) antibody fused to a complete antibody having a different specificity. This gene fusion is expressed by transfection resulting in a tetravalent antibody having dual specificity. However, it is generally recognized in the art that when the teachings in the art, including WO 199509917, are followed while attempting to create useful bispecific antibodies skilled artisans frequently encounter significant problems associated with chemical and physical stability of the resulting bispecific antibody(ies). Oftentimes, amino acid changes are required in the resulting bispecific antibody(ies) to sufficiently overcome these problems. Neither the need for amino acid changes, nor the actual changes that will overcome the resulting problems are suggested in the art. Further, the changes that are required are most often not routine or derived from common general knowledge. Likewise, bispecific antibodies generated from known antibodies are often found to be less desirable in at least one important functional pharmacokinetic or pharmacodynamic property as compared to the parental antibodies themselves.

PCT International Publication WO 2010/115551 discloses a trivalent, bispecific anti-human EGFR and MET antibody (BsAB01), in which a single chain Fab fragment, i.e., one-armed 5D5, was fused to the carboxyl-terminus of one of the two heavy chains of cetuximab. It has been reported that BsAB01 reduces the internalization of MET, compared to the internalization of MET induced by the monospecific, monovalent parent MET antibody. In OVCAR-8 proliferation assays, BsAB01 led to 8% inhibition compared to 2% inhibition with the combination of cetuximab and onartuzumab. In the presence of HGF, BsAB01 led to 15% inhibition compared to 10% inhibition with the combination of cetuximab and onartuzumab.

Additionally, the generation of a bispecific antibody targeting both EGFR and cMET, EMI-mAb, using controlled Fab Arm Exchange (cFAE), a process that involves mixing two parental antibodies (in this case, with specificity for either EGFR or MET) under reducing conditions, followed by re-oxidation has been disclosed (Moores, S., et al., EORTC Annual Meeting, poster #B241 (October 2013)). EM1-mAb was reported, inter alia, to exhibit superior activity compared to the combination of monovalent control antibodies in at least one in vitro ERK phosphorylation assay.

United States Patent Application Publication US 2014/0302029 describes the generation of bispecific antibodies targeting both EGFR and cMET which were constructed by fusing an anti-EGFR scFv based on the sequence of cetuximab to the C-terminus of the IgG2 Fc of an affinity matured and humanized derivative of a mouse antibody (i.e., AbF46) to c-Met.

Thus, a multifunctional antibody that binds MET and EGFR with high affinity, effectively neutralizes MET activation by HGF and EGFR activation by EGF family ligands, and/or provides superior activity in internalizing and/or degrading MET and EGFR (both wild-type and mutants) relative to combinations of single-agents is needed as an effective pharmacological intervention for certain cancers. Particularly, desirable are such anti-MET/EGFR antibodies that i) may more effectively treat cancers characterized by having one or more KRAS mutations, ii) demonstrate superior activity in preventing or delaying the development of resistance to other MET and/or EGFR inhibitors including, but not limited to, erlotinib, gefitinib, lapatinib and vemurafenib, as compared to relevant combinations of single-agents, iii) elicit minimal or no measurable agonist activity, and/or iv) demonstrate in vivo stability, physical and chemical stability including, but not limited to, thermal stability, solubility, low self-association, and pharmacokinetic characteristics which are acceptable for development and/or use in the treatment of cancer. However, while generally following the teachings in WO 199509917 when attempting to create tetravalent, multifunctional anti-MET/EGFR antibodies comprising certain anti-MET antibodies of WO 2010/059654 and certain anti-EGFR antibodies of U.S. Pat. No. 7,723,484, the present inventors encountered significant problems associated with chemical and physical stability and the loss of desired binding properties with respect to one or both of the target receptors, MET and EGFR. Therefore, an extensive engineering effort involving many amino acid changes were required to sufficiently overcome these problems. Neither the need for nor the actual changes are suggested in the art. Further, the several changes are not routine or derived from common general knowledge. Likewise, the parental antibodies themselves did not have these problems, suggesting that the local environment around critical areas differed in the context of multifunctional anti-MET/EGFR antibodies.

Accordingly, the present invention provides tetravalent, multifunctional antibodies that bind to EGFR and MET. These multifunctional antibodies induce co-localization of EGFR and MET on the cell surface, internalization and/or degradation of MET, and, surprisingly, even greater internalization and degradation of EGFR compared with cetuximab in tumor cells with high MET expression. Moreover, these anti-MET/EGFR multifunctional antibodies exhibit higher avidity binding to MET than the parent anti-MET antibody in tumor cells with low to moderate MET expression.

Accordingly, the present invention provides tetravalent, multifunctional antibodies that bind to EGFR and MET. These multifunctional antibodies induce co-localization of EGFR and MET on the cell surface, internalization and/or degradation of MET, and, surprisingly, even greater internalization and degradation of EGFR compared with cetuximab in tumor cells with high MET expression. Moreover, these anti-MET/EGFR multifunctional antibodies exhibit higher avidity binding to MET than the parent anti-MET antibody in tumor cells with low to moderate MET expression. Furthermore, these multifunctional anti-MET/EGFR antibodies exhibit superior activities compared to the combination of two individual antibodies in inhibition of tumor cell growth in cell culture as well as in mouse xenograft models. They also appear to have superior activity than the combination of individual MET and EGFR antibodies in restoring tumor cell sensitivity to various target therapies, including erlotinib and PLX4032 (i.e., a B-Raf inhibitor) in the presence of HGF and/or EGF. Such anti-MET/EGFR antibodies may also prove more effective against a high EGFR expressing tumor or a tumor which is resistant, or has become resistant, to one or more anti-EGFR antibodies (e.g., cetuximab, panitumumab, etc.) and/or one or more small molecule inhibitors of EGFR (e.g., erlotinib), including, but not limited to, tumors harboring KRAS mutations. In various embodiments of the present invention, these multifunctional antibodies bind to MET and EGFR simultaneously, neutralize activation of MET by HGF, and EGFR by EGF, inhibit ligand dependent and independent cell proliferation of many types of cancer cells expressing MET and EGFR, induce co-localization of EGFR and MET on the cell surface, induce internalization and/or degradation of MET, and, surprisingly, induce even greater internalization and degradation of EGFR compared with cetuximab in tumor cells with high MET expression.

An embodiment of the present invention is a multifunctional antibody comprising:

(a) an antibody that binds MET and comprises:
  i) a heavy chain comprising heavy chain complementarity determining regions (CDRs) HCDR1, HCDR2, and HCDR3 consisting of the amino acid sequences of GYTFTDYYMH (SEQ ID NO: 11), RVNPNRRGTTYNQKFEG (SEQ ID NO: 12), and ARANWLDY (SEQ ID NO: 13), respectively; and
  ii) a light chain comprising light chain CDRs LCDR1, LCDR2, and LCDR3 consisting of the amino acid sequences of SVSSSVSSIYLH (SEQ ID NO: 14), YSTSNLAS (SEQ ID NO: 15) and QVYSGYPLT (SEQ ID NO: 16), respectively; and
(b) a scFv polypeptide that binds to human EGFR and comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
  ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively, and wherein the C-terminus of the scFv polypeptide is fused via a peptide linker to the N-terminus of the MET antibody heavy chain.

Another embodiment of the present invention is a multifunctional antibody comprising:
(a) an antibody that binds MET and comprises:
  i) a first heavy chain and a second heavy chain wherein each of the heavy chains comprise heavy chain CDRs HCDR1, HCDR2, and HCDR3 consisting of the amino acid sequences of GYTFTDYYMH (SEQ ID NO: 11), RVNPNRRGTTYNQKFEG (SEQ ID NO: 12), and ARANWLDY (SEQ ID NO: 13), respectively; and
  ii) a first light chain and a second light chain wherein each of the light chains comprises light chain CDRs LCDR1, LCDR2, and LCDR3 consisting of the amino acid sequences of SVSSSVSSIYLH (SEQ ID NO: 14), YSTSNLAS (SEQ ID NO: 15) and QVYSGYPLT (SEQ ID NO: 16), respectively; and
(b) a first scFv polypeptide and a second scFv polypeptide wherein each of the scFv polypeptides binds to human EGFR and wherein each of the scFv polypeptides comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
  ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively, and wherein the C-terminus of the first scFv polypeptide is fused via a peptide linker to the N-terminus of the first heavy chain and the C-terminus of the second scFv polypeptide is fused via a peptide linker to the N-terminus of the second heavy chain.

A further embodiment of the present invention is a multifunctional antibody comprising two first polypeptides and two second polypeptides wherein both first polypeptides comprise the amino acid sequence of SEQ ID NO: 25, SEQ ID NO: 26, SEQ ID NO: 27, SEQ ID NO: 29, SEQ ID NO: 31, SEQ ID NO: 52 or SEQ ID NO: 53; and both second polypeptides comprise the amino acid sequence of SEQ ID NO: 33, and wherein said multifunctional antibody binds to EGFR and MET.

Another embodiment of the present invention is a pharmaceutical composition, comprising any one of the foregoing multifunctional antibodies, or MET and EGFR binding fragments thereof, and a pharmaceutically acceptable carrier, diluent, or excipient.

Another embodiment of the present invention is any one of the foregoing multifunctional antibodies, or a MET and EGFR binding fragment thereof, for use in therapy.

Another embodiment of the present invention is any one of the foregoing multifunctional antibodies, or a MET and EGFR binding fragment thereof, for use in treating a cancer.

Another embodiment of the present invention is any one of the foregoing multifunctional antibodies, or a MET and EGFR binding fragment thereof, for use in treating a cancer wherein both MET and EGFR are expressed by the patient's tumor.

Another embodiment of the present invention is any one of the foregoing multifunctional antibodies, or a MET and EGFR binding fragment thereof, for use in treating a cancer wherein MET and/or EGFR are expressed by the patient's tumor at a low, moderate, or high level and/or tumor or a tumor which is resistant, or has become resistant, to one or more anti-EGFR antibodies (e.g., cetuximab, panitumumab, etc.) and/or one or more small molecule inhibitors of EGFR (e.g., erlotinib), including, but not limited to, tumors harboring KRAS mutations. In various embodiments of such an invention, the use of a multifunctional antibody, or a MET and EGFR binding fragment thereof, for treating a cancer wherein MET and/or EGFR are expressed by the patient's tumor at a low, moderate, or high level and/or a tumor which is resistant, or has become resistant, to one or more anti-EGFR antibodies (e.g., cetuximab, panitumumab, etc.) and/or one or more small molecule inhibitors of EGFR (e.g., erlotinib), including, but not limited to, tumors harboring one or more KRAS mutations may further comprise a step of identifying the patient in need of the treatment of the cancer, prior to the step of administering the multifunctional antibody of the present invention, or a MET and EGFR binding fragment thereof, to the patient.

Another embodiment of the present invention is any one of the foregoing multifunctional antibodies, or a MET and EGFR binding fragment thereof, for use in treating NSCLC, SCLC, gastric cancer, colorectal cancer, cholangiocarcinoma, esophageal cancer, melanoma, including, but not limited to, uveal melanoma, renal cancer, liver cancer, bladder cancer, cervical cancer, or head and neck cancer.

Another embodiment of the present invention is a method of treating a cancer, comprising administering to a human patient in need thereof an effective amount of any one of the foregoing multifunctional antibodies, or a MET and EGFR binding fragment thereof.

FIG. 1 illustrates western blotting results showing that anti-MET/EGFR multifunctional antibodies NH-YK and NH-H9 induce degradation of EGFR and MET in the cancer cell lines H1993 (NSCLC), MKN45 (gastric carcinoma), and H441 (NSCLC). The cancer cell lines were treated overnight with 100 nM of antibody NH-YK, antibody NH-H9 or control antibodies. EGFR and MET degradation was determined by western blotting of cell lysates. The anti-MET/EGFR multifunctional antibodies NH-YK and NH-H9 trigger significant degradation of EGFR whereas cetuximab or a combination of the parental anti-MET antibody and cetuximab did not. Lane 1: hIgG4; Lane 2: anti-MET Ab; Lane 3: cetuximab; Lane 4 anti-MET Ab+cetuximab; Lane 5: NH-YK; Lane 6: NH-H9.

Figure 1:
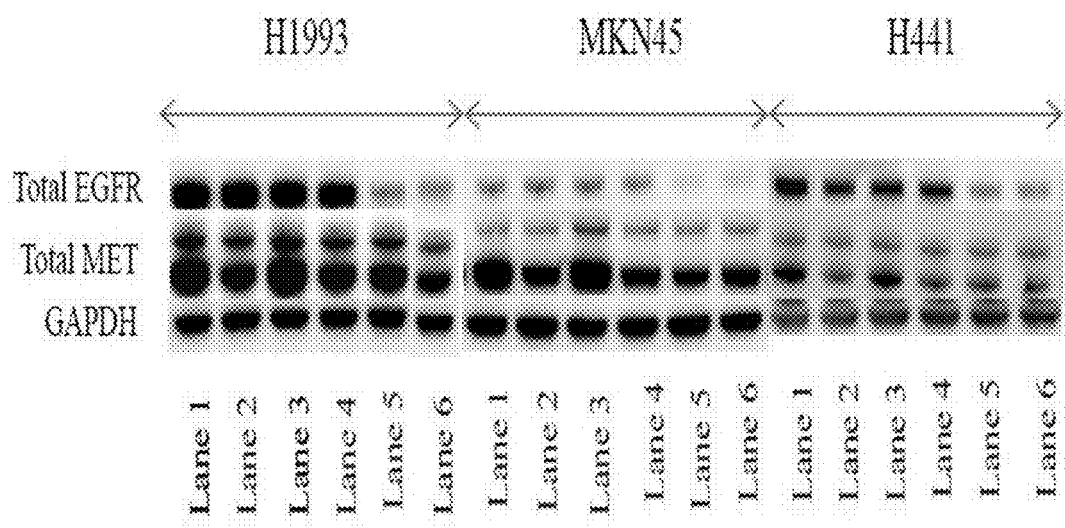

FIG. 6 is a graph showing that administration of the anti-MET/EGFR multifunctional antibody H9 at 27 mg/kg resulted in significantly greater antitumor efficacy than any other treatment in immunodeficient mice bearing H1993 NSCLC xenografts. Mice xenografts were treated with either vehicle control, the anti-MET/EGFR multifunctional antibody H9 (4 and 27 mg/kg), anti-MET alone (3 and 20 mg/kg), cetuximab (3 and 20 mg/kg) or the combination of anti-MET plus cetuximab (3 mg/kg and 20 mg/kg of each antibody) once a week for five consecutive weeks.

FIG. 7 is a graph showing that administration of the anti-MET/EGFR multifunctional antibody H9 at 27 mg/kg resulted in significantly greater antitumor efficacy than any other treatment in immunodeficient mice bearing H441 xenografts. Mice xenografts were treated with either vehicle control, the anti-MET/EGFR multifunctional antibody H9 (4 and 27 mg/kg), anti-MET alone (3 and 20 mg/kg), cetuximab (3 and 20 mg/kg) or the combination of anti-MET plus cetuximab (3 mg/kg and 20 mg/kg of each antibody) once a week for five consecutive weeks.

The terms "EGFR", "ErbB 1", and "EGF receptor" are used interchangeably herein to refer to EGFR protein (see, for example, UniProtKB/Swiss-Prot entry P00533). Herein, "EGFR extracellular domain" or "EGFR ECD" refers to a domain of EGFR that is outside of a cell, either anchored to a cell membrane, or in circulation, including fragments thereof. In one embodiment, the extracellular domain of EGFR may comprise four domains: "Domain I" (amino acid residues from about 1-158), "Domain II" (amino acid residues 159-336), "Domain III" (amino acid residues 337-470), and "Domain IV" (amino acid residues 471-645), where the boundaries are approximate, and may vary by about 1-3 amino acids.

The terms "MET polypeptide", "MET receptor", "MET", "HGF receptor" or "HGFR" are used interchangeably herein and, unless otherwise indicated, are intended to refer to the human receptor tyrosine kinase, as well as functionally active, mutated forms thereof, that bind human hepatocyte growth factor. Specific examples of MET include, e.g., a human polypeptide encoded by the nucleotide sequence provided in GenBank accession no. NM_000245, or the human protein encoded by the polypeptide sequence provided in GenBank accession no. NP_000236. The structure of MET is depicted schematically as:

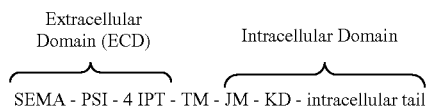

SEMA: Sema domain
PSI: Plexin, Semaphorins, and Integrins domain
IPT: 4 Immunoglobulins, Plexins, and Transcription factor domains
TM: Transmembrane region
JM: Juxtamembrane domain
KD: Kinase domain The extracellular domain of human MET (herein, MET-ECD) has the amino acid sequence shown in, for example, SEQ ID NO: 35. However, amino acids 1-24 of SEQ ID NO: 35 comprise the signal sequence. Therefore, unless stated otherwise, the term "MET-ECD" as used herein means the mature protein beginning and ending at amino acids 25 and 932, respectively, of SEQ ID NO: 35 (i.e., SEQ ID NO: 36). The SEMA domain consists of approximately 500 amino acid residues at the N-terminus of MET, and contains the α-chain (amino acid residues 25-307 of SEQ ID NO: 35 (i.e., SEQ ID NO: 37) and part of the β-chain (amino acid residues 308-519 of SEQ ID NO: 35 (i.e., SEQ ID NO: 38)).

As used herein, the terms "low", "moderate", and "high" in reference to the cell surface expression of MET or EGFR for a tumor or a cell line is intended to mean less than about 0.3 million, greater than about 0.3 million, and greater than about 1 million receptors per cell, respectively.

As used herein, a "multifunctional antibody" refers to a molecule comprising an antibody having one antigen-binding specificity and an antigen-binding fragment having a different antigen-binding specificity. Preferably, a multifunctional antibody refers to a molecule comprising i) an antibody having antigen-binding specificity to MET and ii) a single chain variable fragment (scFv) having antigen-binding specificity to EGFR.

Unless indicated otherwise, the term "antibody", as used herein, is intended to refer to an immunoglobulin molecule comprising two heavy chains (HC) and two light chains (LC) interconnected by disulfide bonds. The amino terminal portion of each chain includes a variable region of about 100 to about 110 amino acids primarily responsible for antigen recognition via the CDRs contained therein. The carboxy-terminal portion of each chain defines a constant region primarily responsible for effector function.

Unless indicated otherwise, the term "NH-YK", as used herein in reference to a multifunctional antibody of the invention, is intended to refer to a multifunctional antibody comprising two first polypeptides and two second polypeptides wherein both first polypeptides comprise the amino acid sequence of SEQ ID NO: 27; and both second polypeptides comprise the amino acid sequence of SEQ ID NO: 33, and wherein said multifunctional antibody binds to EGFR and MET.

Unless indicated otherwise, the term "NH-H9", as used herein in reference to a multifunctional antibody of the invention, is intended to refer to a multifunctional antibody comprising two first polypeptides and two second polypeptides wherein both first polypeptides comprise the amino acid sequence of SEQ ID NO: 29; and both second polypeptides comprise the amino acid sequence of SEQ ID NO: 33, and wherein said multifunctional antibody binds to EGFR and MET.

Unless indicated otherwise, the term "H9", as used herein in reference to a multifunctional antibody of the invention, is intended to refer to a multifunctional antibody comprising two first polypeptides and two second polypeptides wherein both first polypeptides comprise the amino acid sequence of SEQ ID NO: 52; and both second polypeptides comprise the amino acid sequence of SEQ ID NO: 33, and wherein said multifunctional antibody binds to EGFR and MET.

Unless indicated otherwise, the term "YK", as used herein in reference to a multifunctional antibody of the invention, is intended to refer to a multifunctional antibody comprising two first polypeptides and two second polypeptides wherein both first polypeptides comprise the amino acid sequence of SEQ ID NO: 31; and both second polypeptides comprise the amino acid sequence of SEQ ID NO: 33, and wherein said multifunctional antibody binds to EGFR and MET.

The term "antigen-binding fragment" as used herein is intended to mean any antibody fragment that retains the ability to bind to its antigen. Such "antigen-binding fragments" can be selected from the group consisting of Fv, scFv, Fab, F(ab')$_2$, Fab', scFv-Fc fragments and diabodies. An antigen-binding fragment of an antibody will typically comprise at least one variable region. Preferably, an antigen-binding fragment comprises a heavy chain variable region (HCVR) and a light chain variable region (LCVR). More preferably, an antigen-binding fragment comprises HCVRs and LCVRs which confer antigen-binding specificity to both MET and EGFR (i.e., a "MET and EGFR binding fragment").

The term "complementarity determining region" and "CDR" as used herein is intended to mean the non-contiguous antigen combining sites found within the variable region of both HC and LC polypeptides of an antibody or an antigen-binding fragment thereof. These particular regions have been described by others including Kabat, et al., *Ann. NY Acad. Sci.* 190:382-93 (1971); Kabat et al., J. Biol. Chem. 252:6609-6616 (1977); Kabat, et al., *Sequences of Proteins of Immunological Interest*, Fifth Edition, U.S. Department of Health and Human Services, NIH Publication No. 91-3242 (1991); Chothia, et al., J. Mol. Biol. 196:901-917 (1987); MacCallum, et al., J. Mol. Biol., 262:732-745 (1996); and North, et al., J. Mol. Biol., 406, 228-256 (2011) where the definitions include overlapping or subsets of amino acid residues when compared against each other.

The CDRs are interspersed with regions that are more conserved, termed framework regions ("FR"). Each LCVR and HCVR is composed of three CDRs and four FRs, arranged from amino-terminus to carboxy-terminus in the following order: FR1, CDRI, FR2, CDR2, FR3, CDR3, FR4. The three CDRs of the light chain are referred to as "LCDR1, LCDR2, and LCDR3" and the three CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with known conventions (e.g., Kabat (1991) Chothia (1987), and/or North (2011)). In different embodiments of the invention, the FRs of the antibody and/or antigen-binding fragment (e.g., scFv) may be identical to the human germline sequences, or may be naturally or artificially modified.

A "single chain fragment variable" or "scFv" or "scFv polypeptide" refers to a single folded polypeptide comprising the LCVR domain and the HCVR domain of an antibody linked through a linker molecule. In such a scFv polypeptide, the HCVR domain and LCVR domain can be either in the HCVR-linker-LCVR or LCVR-linker-HCVR order. The linker can be a flexible peptide linker which enables the HCVR domain and LCVR domains to be folded as a functional monomeric unit for recognizing an antigen. The three CDRs of the LCVR domain of the scFv are referred to herein as "scFv-LCDR1, scFv-LCDR2, and scFv-LCDR3" and the three CDRs of the HCVR domain of the scFv are referred to herein as "scFv-HCDR1, scFv-HCDR2, and scFv-HCDR3."

The term "surface plasmon resonance (SPR)", as used herein, refers to an optical phenomenon that allows for the analysis of real-time interactions by detection of alterations in protein concentrations within a biosensor matrix, for example using the BIAcore™ system (Biacore Life Sciences Division, GE Healthcare, Piscataway, N.J.).

The term "$K_D$", as used herein, is intended to refer to the equilibrium dissociation constant of a particular antibody-antigen or antibody fragment-antigen interaction.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, SPR, and the like. For example, an antibody that "specifically binds" MET or EGFR, as used in the context of the present invention, includes antibodies that bind MET-ECD (or a portion thereof) and/or EGFR-ECD (or a portion thereof) with a $K_D$ of less than about 10 nM, less than about 5 nM, less than about 4 nM, less than about 3 nM, less than about 2 nM, less than about 1 nM, less than about 0.5 nM, less than about 0.3 nM, less than about 0.2 nM, or less than about 0.1 nM as measured in a SPR assay. (see, e.g., Example 1, herein). Preferably, a multifunctional antibody of the present invention specifically binds MET-ECD (or portion thereof) and EGFR-ECD (or portion thereof) with a $K_D$ of between about 10 nM and about 0.1 nM, between about 5 nM and about 0.1 nM, between about 2 nM and about 0.1 nM, between about 1 nM and about 0.1 nM, between about 0.75 nM and about 0.1 nM, between about 0.5 nM and about 0.1 nM as measured in a SPR assay.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "linker molecule" or "linker" as used within the invention preferably denotes a peptide linker. The peptide linkers utilized in certain embodiments of the invention are used to link the antibody, antigen-binding sites, and/or antibody fragments comprising the different antigen-binding sites (e.g. scFv, full length antibody, a $V_H$ domain and/or a $V_L$ domain) together to form a multifunctional antibody according to the invention. Preferably, the peptide linkers are glycine-rich peptides with at least 5 amino acids, preferably of at least 10 amino acids, more preferably between 10 and 50 amino acids. In some embodiments of the present invention, said glycine-rich peptide linker is $(G_xS)_n$ with G=glycine, S=serine, (x=3 and n=3, 4, 5 or 6) or (x=4 and n=2, 3, 4 or 5). For example, in some embodiments of the present invention, said glycine-rich peptide linker is $(G_xS)_n$ with G=glycine, S=serine, x=4 and n=2, 3, 4 or 5 (i.e., GGGGSGGGGS (SEQ ID NO: 47), GGGGSGGGGSGGGGS (SEQ ID NO: 48), GGGGSGGGGSGGGGSGGGGS (SEQ ID NO: 49), or GGGGSGGGGSGGGGSGGGGSGGGGS (SEQ ID NO: 50), respectively. In certain embodiments of the present invention, additional glycines or threonines, e.g., GSTG, TG, GG, or GGGT can be added to either end of the $(G_xS)_n$ formatted glycine-rich peptide linker. For example, in some embodiments of the present invention, said glycine-rich peptide linker is GGGSGGGGSGGGGSGSTG (SEQ ID NO: 51).

The term "C-terminus", and grammatical variations thereof, including, but not limited to, carboxyl-terminus, carboxy-terminus, C-terminal, C-terminal end, or COOH-terminus, are used herein to denote the end of an amino acid chain (protein or polypeptide), which may be terminated by a free carboxyl group (—COOH). When the protein is translated from messenger RNA, it is created from N-terminus to C-terminus. The convention for denoting peptide sequences is to depict the C-terminal end on the right and list the sequence from N- to C-terminus.

The term "N-terminus", and grammatical variations thereof, including, but not limited to, amino-terminus, $NH_2$-terminus, N-terminal end or amine-terminus, are used herein to denote the beginning of an amino acid chain (protein or polypeptide), terminated by an amino acid with a free amine group (—$NH_2$). The convention for denoting peptide sequences is to put the N-terminus on the left and list the sequence from N- to C-terminus.

The phrase "human engineered antibody" or "humanized antibody" refers to the antibody compounds disclosed herein as well as antibodies and antigen-binding fragments thereof that have binding and functional properties similar to the antibody compounds disclosed herein, and that have framework regions that are substantially human or fully human surrounding CDRs derived from a non-human antibody. "Framework region" or "framework sequence" refers to any one of framework regions 1 to 4. Human engineered antibodies and antigen-binding fragments encompassed by the present invention include compounds wherein any one or more of framework regions 1 to 4 is substantially or fully human, i.e., wherein any of the possible combinations of individual substantially or fully human framework regions 1 to 4, is present. For example, this includes antigen-binding compounds in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, or about 95% sequence identity to a known human germline framework sequence.

Fully human frameworks are those that are identical to a known human germline framework sequence. Human framework germline sequences are known in the art and can be obtained from various sources including IMGT®, the international ImMunoGeneTics information system (see, for example, Marie-Paule Lefranc, et al., Nucleic Acid Research, volume 37, Database issue, D1006-D1012) or from *The Immunoglobulin Facts Book* by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L1I, L12, L2, L5, L15, L6, L8, O12, O2, and O8; and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Human engineered antibodies exhibiting functional properties similar to the antibody compounds disclosed herein can be generated using several different methods. The specific antibody compounds disclosed herein can be used as templates or parent antibody compounds to prepare additional antibody compounds. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816, 397; 5,225,539, and 5,693,761; computer programs ABMOD and ENCAD as described in Levitt, *J. Mol. Biol.* 168:595-620 (1983); and the method of Winter and co-workers (Jones et al. *Nature* 321:522-525 (1986); Riechmann, et al. *Nature,* 332: 323-327 (1988); and Verhoeyen, et al. *Science* 239:1534-1536 (1988).

Applying the teachings of the present invention, a person skilled in the art can use common techniques, e.g., site-directed mutagenesis, to substitute amino acids within the presently disclosed CDR and framework sequences and thereby generate further variable region amino acid sequences derived from the present sequences. Up to all 19 alternative naturally occurring amino acids can be introduced at a specific substitution site. The methods disclosed herein can then be used to screen these additional variable region amino acid sequences to identify sequences having the indicated in vivo functions. In this way, further sequences suitable for preparing human engineered antibodies and antigen-binding portions thereof in accordance with the present invention can be identified. Preferably, amino acid substitution within the frameworks is restricted to one, two, or three positions within any one or more of the three light chain and/or heavy chain framework regions disclosed herein. Preferably, amino acid substitution within the CDRs is restricted to one, two, or three positions within any one or more of the three light chain and/or heavy chain CDRs. Combinations of the various changes within these framework regions and CDRs described above is also contemplated herein.

Tables 1 and 2 below depict the amino acid sequences and consensus amino acid sequences of the CDRs for the preferred human engineered antibodies disclosed herein, and the SEQ ID NOs for the amino acid sequences of the HCVR and LCVR polypeptides for the preferred human engineered antibodies or antigen-binding fragments thereof, disclosed herein.

TABLE 1

| | HCDR1 | HCDR2 | HCDR3 | HCVR |
|---|---|---|---|---|
| Anti-EGFR scFv YK | GFSLTNYGVH (SEQ ID NO: 1) | VIYSGGNTDYNTPF KG (SEQ ID NO: 2) | ARALDYYDYDFA Y (SEQ ID NO: 3) | 17 |
| Anti-EGFR scFv H9 | GFSLTNYGVH (SEQ ID NO: 1) | VIWSGGNTDYNTPF TG (SEQ ID NO: 7) | ARALDYYDYDFA Y (SEQ ID NO: 3) | 19 |

TABLE 1-continued

| | HCDR1 | HCDR2 | HCDR3 | HCVR |
|---|---|---|---|---|
| Anti-EGFR scFv Consensus | GFSLTNYGVH (SEQ ID NO: 1) | VIX$_1$SGGNTDYNTPF X$_2$G (SEQ ID NO: 9) | ARALDYYDYDFA Y (SEQ ID NO: 3) | |
| Anti-Met Ab | GYTFTDYYMH (SEQ ID NO: 11) | RVNPNRRGTTYNQK FEG (SEQ ID NO: 12) | ARANWLDY (SEQ ID NO: 13) | 21 |

In Table 1 above, X$_1$ is Y or W and X$_2$ is K or T.

TABLE 2

| | LCDR1 | LCDR2 | LCDR3 | LCVR |
|---|---|---|---|---|
| Anti-EGFR scFv YK | RASYSIGTNIH (SEQ ID NO: 4) | RYAKESIS (SEQ ID NO: 5) | QQNNAWPTT (SEQ ID NO: 6) | 18 |
| Anti-EGFR scFv H9 | RASYSIGTNIH (SEQ ID NO: 4) | YYASRSIS (SEQ ID NO: 8) | QQNNAWPTT (SEQ ID NO: 6) | 20 |
| Anti-EGFR scFv Consensus | RASYSIGTNIH (SEQ ID NO: 4) | X$_1$YAX$_2$X$_3$SIS (SEQ ID NO: 10) | QQNNAWPTT (SEQ ID NO: 6) | |
| Anti-MET Ab | SVSSSVSSIYLH (SEQ ID NO: 14) | YSTSNLAS (SEQ ID NO: 15) | QVYSGYPLT (SEQ ID NO: 16) | 22 |

In Table 2 above, X$_1$ is R or Y, X$_2$ is K or S, and X$_3$ is E or R

An embodiment of the present invention is a multifunctional antibody comprising:
(a) an antibody that binds to an epitope within the α-chain of MET at an amino acid sequence selected from the group consisting of:

i) VVDTYYDDQL, (SEQ ID NO: 39)
 ii) ISCGSVNRGTCQRHVFPHNHTADIQS, (SEQ ID NO: 40)
 iii) ALGAKVLSSVKDRFINF, (SEQ ID NO: 41) and
 iv) VRRLKETKDGFM; (SEQ ID NO: 42)

and
(b) a scFv polypeptide that binds to EGFR and comprises:
 i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
 ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively, wherein the multifunctional antibody induces internalization and/or degradation of cell surface MET and EGFR.

In various embodiments of such invention, the multifunctional antibody binds to an epitope within the α-chain of MET at an amino acid sequence i) VVDTYYDDQL (SEQ ID NO: 39), ii) ISCGSVNRGTCQRHVFPHNHTADIQS (SEQ ID NO: 40), iii) ALGAKVLSSVKDRFINF (SEQ ID NO: 41), and/or iv) VRRLKETKDGFM (SEQ ID NO: 42). In various embodiments of such invention, the multifunctional antibody may bind to an epitope within the α-chain of MET at an amino acid sequence selected from the group consisting of:

i) DTYYDD, (SEQ ID NO: 43)
 ii) HVFPHNHTADIQS, (SEQ ID NO: 44)
 iii) FINF, (SEQ ID NO: 45) and
 iv) KETKDGFM. (SEQ ID NO: 46)

In various embodiments of such invention, the multifunctional antibody may bind a conformational epitope characterized by the amino acids sequence DTYYDD (SEQ ID NO: 43), HVFPHNHTADIQS (SEQ ID NO: 44), FINF (SEQ ID NO: 45), and KETKDGFM (SEQ ID NO: 46), inclusive. Furthermore, in various embodiments of such invention the multifunctional antibody induces HGF-independent and EGF-independent internalization and/or degradation of cell surface MET and EGFR, respectively. In other embodiments of such an invention, the scFv polypeptide that binds to EGFR comprises:
i) a HCVR domain comprising scFv CDRs scFv-HCDR1, scFv-HCDR2, and scFv-HCDR3 consisting of the amino acid sequences GFSLTNYGVH (SEQ ID NO: 1), VIYSGGNTDYNTPFKG (SEQ ID NO: 2), and ARALDYYDYDFAY (SEQ ID NO: 3), respectively, and ii) a LCVR domain comprising scFv CDRs scFv-LCDR1, scFv-LCDR2, and scFv-LCDR3 consisting of the amino acid sequences RASYSIGTNIH (SEQ ID NO: 4), RYAKESIS (SEQ ID NO: 5), and QQNNAWPTT (SEQ ID NO: 6), respectively. In other embodiments of such an invention the scFv polypeptide that binds to EGFR comprises: i) a HCVR domain comprising scFv CDRs scFv-HCDR1, scFv-HCDR2, and scFv-HCDR3 consisting of the amino acid sequences GFSLTNYGVH (SEQ ID NO: 1), VIYSG-GNTDYNTPFKG (SEQ ID NO: 2), and ARALDYYDY-DFAY (SEQ ID NO: 3), respectively; and ii) a LCVR domain comprising scFv CDRs scFv-LCDR1, scFv-LCDR2, and scFv-LCDR3 consisting of the amino acid sequences RASYSIGTNIH (SEQ ID NO: 4), RYAKESIS (SEQ ID NO: 5), and QQNNAWPTT (SEQ ID NO: 6), respectively, and wherein the C-terminus of the scFv polypeptide is fused via a peptide linker to the N-terminus of the MET antibody heavy chain.

An embodiment of the present invention is a multifunctional antibody comprising:
(a) an antibody that binds MET and comprises:
  i) a heavy chain comprising heavy chain CDRs HCDR1, HCDR2, and HCDR3 consisting of the amino acid sequences of GYTFTDYYMH (SEQ ID NO: 11), RVN-PNRRGTTYNQKFEG (SEQ ID NO: 12), and ARAN-WLDY (SEQ ID NO: 13), respectively; and
  ii) a light chain comprising light chain CDRs LCDR1, LCDR2, and LCDR3 consisting of the amino acid sequences of SVSSSVSSIYLH (SEQ ID NO: 14), YSTSNLAS (SEQ ID NO: 15) and QVYSGYPLT (SEQ ID NO: 16), respectively; and
(b) a scFv polypeptide that binds to EGFR and comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
  ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively.

In other embodiments of such an invention the scFv polypeptide that binds to EGFR comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIYSGGNTDYNTPFKG (SEQ ID NO: 2), and ARALDYYDYDFAY (SEQ ID NO: 3), respectively; and
  ii) a LCVR domain comprising scFv CDRs scFv-LCDR1, scFv-LCDR2, and scFv-LCDR3 consisting of the amino acid sequences RASYSIGTNIH (SEQ ID NO: 4), RYAKESIS (SEQ ID NO: 5), and QQNNAWPTT (SEQ ID NO: 6), respectively.

In other embodiments of such an invention the scFv polypeptide that binds to EGFR comprises a HCVR domain comprising the amino acid sequence of SEQ ID NO: 17 and a LCVR domain comprising the amino acid sequence of SEQ ID NO: 18. In other embodiments of such an invention the scFv polypeptide that binds to EGFR comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIYSGGNTDYNTPFKG (SEQ ID NO: 2), and ARALDYYDYDFAY (SEQ ID NO: 3), respectively; and
  ii) a LCVR domain comprising scFv CDRs scFv-LCDR1, scFv-LCDR2, and scFv-LCDR3 consisting of the amino acid sequences RASYSIGTNIH (SEQ ID NO: 4), RYAKESIS (SEQ ID NO: 5), and QQNNAWPTT (SEQ ID NO: 6), respectively, and wherein the C-terminus of the scFv polypeptide is fused via a peptide linker to the N-terminus of the MET antibody heavy chain.

In other embodiments of such an invention the multifunctional antibody comprises:
  i) a heavy chain comprising the amino acid sequence of SEQ ID NO: 53; and
  ii) a light chain comprising the amino acid sequence of SEQ ID NO: 33.

An embodiment of the present invention is a multifunctional antibody comprising:
(a) an antibody that binds MET and comprises:
  i) a heavy chain comprising heavy chain CDRs HCDR1, HCDR2, and HCDR3 consisting of the amino acid sequences of GYTFTDYYMH (SEQ ID NO: 11), RVN-PNRRGTTYNQKFEG (SEQ ID NO: 12), and ARAN-WLDY (SEQ ID NO: 13), respectively; and
  ii) a light chain comprising light chain CDRs LCDR1, LCDR2, and LCDR3 consisting of the amino acid sequences of SVSSSVSSIYLH (SEQ ID NO: 14), YSTSNLAS (SEQ ID NO: 15) and QVYSGYPLT (SEQ ID NO: 16), respectively; and
(b) a scFv polypeptide that binds to EGFR and comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIX$_1$SGGNTDYNTPFX$_2$G (SEQ ID NO: 9), wherein X$_1$ is Y or W and X$_2$ is K or T, and ARALDYYDYDFAY (SEQ ID NO: 3), respectively, and
  ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively.

In other embodiments of such an invention the scFv polypeptide that binds to EGFR comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIWSGGNTDYNTPFTG (SEQ ID NO: 7), and ARALDYYDYDFAY (SEQ ID NO: 3), respectively; and
  ii) a LCVR domain comprising scFv CDRs scFv-LCDR1, scFv-LCDR2, scFv-LCDR3 consisting of the amino acid sequences RASYSIGTNIH (SEQ ID NO: 4), YYASRSIS (SEQ ID NO: 8), and QQNNAWPTT (SEQ ID NO: 6), respectively.

In other embodiments of such an invention the scFv polypeptide that binds to EGFR comprises:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIWSGGNTDYNTPFTG (SEQ ID NO: 7), and ARALDYYDYDFAY (SEQ ID NO: 3), respectively; and
  ii) a LCVR domain comprising scFv CDRs scFv-LCDR1, scFv-LCDR2, scFv-LCDR3 consisting of the amino acid sequences RASYSIGTNIH (SEQ ID NO: 4), YYASRSIS (SEQ ID NO: 8), and QQNNAWPTT (SEQ ID NO: 6), respectively, and wherein the C-terminus of the scFv polypeptide is fused via a peptide linker to the N-terminus of the MET antibody heavy chain.

In other embodiments of such an invention the multifunctional antibody comprises:
i) a heavy chain comprising the amino acid sequence of SEQ ID NO: 53; and
ii) a light chain comprising the amino acid sequence of SEQ ID NO: 33.

Another embodiment of the present invention is a multifunctional antibody comprising:
(a) an antibody that binds MET and comprises:
   i) a first heavy chain and a second heavy chain wherein each of the heavy chains comprise heavy chain CDRs HCDR1, HCDR2, and HCDR3 consisting of the amino acid sequences of GYTFTDYYMH (SEQ ID NO: 11), RVNPNRRGTTYNQKFEG (SEQ ID NO: 12), and ARANWLDY (SEQ ID NO: 13), respectively; and
   ii) a first light chain and a second light chain wherein each of the light chains comprises light chain CDRs LCDR1, LCDR2, and LCDR3 consisting of the amino acid sequences of SVSSSVSSIYLH (SEQ ID NO: 14), YSTSNLAS (SEQ ID NO: 15) and QVYSGYPLT (SEQ ID NO: 16), respectively; and
(b) a first scFv polypeptide and a second scFv polypeptide wherein each of the scFv polypeptides binds to human EGFR and wherein each of the scFv polypeptides comprises:
   i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
   ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively, and wherein the C-terminus of the first scFv polypeptide is fused via a peptide linker to the N-terminus of the first heavy chain and the C-terminus of the second scFv polypeptide is fused via a peptide linker to the N-terminus of the second heavy chain.

In various embodiments of such invention, the multifunctional antibody binds to an epitope within the α-chain of MET at an amino acid sequence selected from the group consisting of:

```
i)
                                       (SEQ ID NO: 39)
VVDTYYDDQL, ii)
                                       (SEQ ID NO: 40)
ISCGSVNRGTCQRHVFPHNHTADIQS, iii)
                                       (SEQ ID NO: 41)
ALGAKVLSSVKDRFINF,
and iv)
                                       (SEQ ID NO: 42)
VRRLKETKDGFM.
```

In various embodiments of such invention, the multifunctional antibody may bind to an epitope within the α-chain of MET at an amino acid sequence i) VVDTYYDDQL (SEQ ID NO: 39), ii) ISCGSVNRGTCQRHVFPHNHTADIQS (SEQ ID NO: 40), iii) ALGAKVLSSVKDRFINF (SEQ ID NO: 41), and/or iv) VRRLKETKDGFM (SEQ ID NO: 42). In various embodiments of such invention, the multifunctional antibody may bind a conformational epitope characterized by the amino acids sequence DTYYDD (SEQ ID NO: 43), HVFPHNHTADIQS (SEQ ID NO: 44), FINF (SEQ ID NO: 45), and KETKDGFM (SEQ ID NO: 46), inclusive. In other embodiments of such an invention the multifunctional antibody comprises:
i) a first heavy chain and a second heavy chain wherein both heavy chains comprise the amino acid sequence of SEQ ID NO: 53; and
ii) a first light chain and a second light chain wherein both light chains comprise the amino acid sequence of SEQ ID NO:33.

Furthermore, in various embodiments of such invention the multifunctional antibody induces HGF-independent and EGF-independent internalization and/or degradation of cell surface MET and EGFR, respectively.

Another embodiment of the present invention is a multifunctional antibody comprising:
(a) an antibody that binds MET and comprises:
   i) a first heavy chain and a second heavy chain wherein each of the heavy chains comprise heavy chain CDRs HCDR1, HCDR2, and HCDR3 consisting of the amino acid sequences of GYTFTDYYMH (SEQ ID NO: 11), RVNPNRRGTTYNQKFEG (SEQ ID NO: 12), and ARANWLDY (SEQ ID NO: 13), respectively; and
   ii) a first light chain and a second light chain wherein each of the light chains comprises light chain CDRs LCDR1, LCDR2, and LCDR3 consisting of the amino acid sequences of SVSSSVSSIYLH (SEQ ID NO: 14), YSTSNLAS (SEQ ID NO: 15) and QVYSGYPLT (SEQ ID NO: 16), respectively; and
(b) a first scFv polypeptide and a second scFv polypeptide wherein each of the scFv polypeptides binds to human EGFR and wherein each of the scFv polypeptides comprises:
   i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
   ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively, and wherein the C-terminus of the first scFv polypeptide is fused via a peptide linker to the N-terminus of the first heavy chain and the C-terminus of the second scFv polypeptide is fused via a peptide linker to the N-terminus of the second heavy chain.

In other embodiments of such an invention each of the first and second scFv polypeptides that binds to EGFR comprises: i) a HCVR domain comprising scFv CDRs scFv-HCDR1, scFv-HCDR2, and scFv-HCDR3 consisting of the amino acid sequences GFSLTNYGVH (SEQ ID NO: 1), VIYSGGNTDYNTPFKG (SEQ ID NO: 2), and ARALDYYDYDFAY (SEQ ID NO: 3), respectively; and ii) a LCVR domain comprising scFv CDRs scFv-LCDR1, scFv-LCDR2, and scFv-LCDR3 consisting of the amino acid sequences RASYSIGTNIH (SEQ ID NO: 4), RYAKESIS (SEQ ID NO: 5), and QQNNAWPTT (SEQ ID NO: 6), respectively. Alternatively, each of the first and second scFv polypeptides that binds to EGFR comprises: i) a HCVR domain comprising scFv CDRs scFv-HCDR1, scFv-HCDR2, and scFv-HCDR3 consisting of the amino acid sequences GFSLTNYGVH (SEQ ID NO: 1), VIWSGGNTDYNTPFTG (SEQ ID NO: 7), and ARALDYYDYDFAY (SEQ ID NO: 3), respectively; and
ii) a LCVR domain comprising scFv CDRs scFv-LCDR1, scFv-LCDR2, and scFv-LCDR3 consisting of the amino acid sequences RASYSIGTNIH (SEQ ID NO: 4), YYASRSIS (SEQ ID NO: 8), and QQNNAWPTT (SEQ ID NO: 6), respectively.

Another embodiment of the present invention is a multifunctional antibody comprising:
(a) an antibody that binds MET and comprises:
  i) a first heavy chain and a second heavy chain wherein both of the heavy chains comprise the amino acid sequence of SEQ ID NO: 53; and
  ii) a first light chain and a second light chain wherein both of the light chains comprise the amino acid sequence of SEQ ID NO: 33; and
(b) a first scFv polypeptide and a second scFv polypeptide wherein both of the scFv polypeptides bind to EGFR and both of the scFv polypeptides comprise:
  i) a HCVR domain comprising scFv CDRs scFv-HCDR1, scFv-HCDR2, and scFv-HCDR3 consisting of the amino acid sequences GFSLTNYGVH (SEQ ID NO: 1), VIXISGGNTDYNTPFX$_2$G (SEQ ID NO: 9), wherein X$_1$ is Y or W and X$_2$ is K or T, and ARALDYYDYDFAY (SEQ ID NO: 3), respectively; and
  ii) a LCVR domain comprising scFv CDRs scFv-LCDR1, scFv-LCDR2, and scFv-LCDR3 consisting of the amino acid sequences RASYSIGTNIH (SEQ ID NO: 4), X$_1$YAX$_2$X$_3$SIS (SEQ ID NO: 10), wherein X$_1$ is R or Y, X$_2$ is K or S, and X$_3$ is E or R, and QQNNAWPTT (SEQ ID NO: 6), respectively, and wherein the C-terminus of the first scFv polypeptide is fused via a peptide linker to the N-terminus of the first heavy chain and the C-terminus of the second scFv polypeptide is fused via a peptide linker to the N-terminus of the second heavy chain.

In other embodiments of such an invention the first and second scFv polypeptides comprise: i) a HCVR domain comprising scFv CDRs scFv-HCDR1, scFv-HCDR2, and scFv-HCDR3 consisting of the amino acid sequences GFSLTNYGVH (SEQ ID NO: 1), VIYSGGNTDYNTPFKG (SEQ ID NO: 2), and ARALDYYDYDFAY (SEQ ID NO: 3), respectively; and ii) a LCVR domain comprising scFv CDRs scFv-LCDR1, scFv-LCDR2, and scFv-LCDR3 consisting of the amino acid sequences RASYSIGTNIH (SEQ ID NO: 4), RYAKESIS (SEQ ID NO: 5), and QQNNAWPTT (SEQ ID NO: 6), respectively. Alternatively, both scFv polypeptides comprise: i) a HCVR domain comprising scFv CDRs scFv-HCDR1, scFv-HCDR2, and scFv-HCDR3 consisting of the amino acid sequences GFSLTNYGVH (SEQ ID NO: 1), VIWSGGNTDYNTPFTG (SEQ ID NO: 7), and ARALDYYDYDFAY (SEQ ID NO: 3), respectively; and ii) a LCVR domain comprising scFv CDRs scFv-LCDR1, scFv-LCDR2, and scFv-LCDR3 consisting of the amino acid sequences RASYSIGTNIH (SEQ ID NO: 4), YYASRSIS (SEQ ID NO: 8), and QQNNAWPTT (SEQ ID NO: 6), respectively.

In one embodiment the present invention provides, a multifunctional tetravalent antibody comprising:
(a) an antibody comprising two heavy chains and two light chains and capable of binding to an epitope within the α-chain of MET at an amino acid sequence selected from the group consisting of:

i)
VVDTYYDDQL, (SEQ ID NO: 39)

ii)
ISCGSVNRGTCQRHVFPHNHTADIQS, (SEQ ID NO: 40)

iii)
ALGAKVLSSVKDRFINF, (SEQ ID NO: 41)
and iv)
VRRLKETKDGFM; (SEQ ID NO: 42)

and
(b) two scFv polypeptides capable of binding to EGFR comprising the heavy chain variable region of SEQ ID NO: 17 or SEQ ID NO: 19, and the light chain variable region of SEQ ID NO: 18 or SEQ ID NO: 20, wherein the multifunctional antibody induces internalization and/or degradation of cell surface MET and EGFR. In various embodiments of such invention, the multifunctional antibody may bind to an epitope within the α-chain of MET at an amino acid sequence i) VVDTYYDDQL (SEQ ID NO: 39), ii) ISCGSVNRGTCQRHVFPHNHTADIQS (SEQ ID NO: 40), iii) ALGAKVLSSVKDRFINF (SEQ ID NO: 41), and/or iv) VRRLKETKDGFM (SEQ ID NO: 42). In various embodiments of such invention, the multifunctional antibody may bind a conformational epitope characterized by the amino acids sequence DTYYDD (SEQ ID NO: 43), HVFPHNHTADIQS (SEQ ID NO: 44), FINF (SEQ ID NO: 45), and KETKDGFM (SEQ ID NO: 46), inclusive. Furthermore, in various embodiments of such invention the multifunctional antibody induces HGF-independent and EGF-independent internalization and/or degradation of cell surface MET and EGFR, respectively.

In one embodiment of the present invention, a multifunctional tetravalent antibody comprising: (a) two identical scFv polypeptides each capable of binding to EGFR; and (b) an antibody, or antigen-binding fragment thereof, that specifically binds to MET-ECD consisting of the amino acid sequence as in SEQ ID NO: 36, the antibody, or antigen-binding fragment thereof, comprising:
light chain CDRs LCDR1, LCDR2, and LCDR3 consisting of the amino acid sequences SVSSSVSSIYLH (SEQ ID NO: 14), YSTSNLAS (SEQ ID NO: 15), and QVYSGYPLT (SEQ ID NO: 16), respectively, and
heavy chain CDRs HCDR1, HCDR2, and HCDR3 consisting of the amino acid sequences GYTFTDYYMH (SEQ ID NO: 11), RVNPNRRGTTYNQKFEG (SEQ ID NO: 12), and ARANWLDY (SEQ ID NO: 13), respectively, is provided.

In one embodiment of the present invention, a multifunctional tetravalent antibody comprising: (a) two identical scFv polypeptides each capable of binding to EGFR; and (b) a MET antibody comprising two heavy chains and two light chains and capable of binding to MET wherein the two identical scFv polypeptides capable of binding to EGFR are C-terminally fused to the MET antibody via a peptide linker at the C-terminus of each heavy chain of said full-length antibody is provided. In some embodiments of the present invention, the heavy chain variable region of SEQ ID NO: 21, and the light chain variable region of SEQ ID NO: 22, which are both derived from the anti-MET Clone C8-H241 (which is described in detail in WO 2010/059654), can be used to form the antigen-binding sites of the MET antibody that specifically binds to MET.

By gene synthesis and recombinant molecular biology techniques, the HCVR of SEQ ID NO: 17 and the LCVR of SEQ ID NO: 18, or the HCVR of SEQ ID NO: 19 and the LCVR of SEQ ID NO: 20, are linked by a glycine-rich linker of the formula $(G_xS)_n$, x=4, n=5 to form a scFv that specifically binds to EGFR. The EGFR-binding scFv is then attached to the N- or C-terminus of the heavy chain of the anti-MET antibody C8-H241 (human IgG4 subtype) by another glycine-rich linker, creating multifunctional antibodies NH-YK (comprising an anti-EGFR $YK_n$-scFv and anti-Met HC fusion (i.e., SEQ ID NO: 27)), NH-H9 (comprising an anti-EGFR $H9_n$-scFv and anti-Met HC fusion (i.e., SEQ ID NO: 29)), YK (comprising an anti-Met HC and anti-EGFR YK-scFv fusion (i.e., SEQ ID NO: 31)), and H9 (comprising an anti-Met HC and anti-EGFR H9-scFv fusion (i.e., SEQ ID NO: 52)).

Another embodiment of the present invention is a multifunctional antibody that binds MET and EGFR comprising: (a) two first polypeptides wherein both of the first polypeptides comprise the amino acid sequence of SEQ ID NO: 25, SEQ ID NO: 26, SEQ ID NO: 27, SEQ ID NO: 29, SEQ ID NO: 31, SEQ ID NO: 52, or SEQ ID NO: 53; and (b) two second polypeptides wherein both of the second polypeptides comprise the amino acid sequence of SEQ ID NO: 33.

Another embodiment of the present invention is a pharmaceutical composition comprising a multifunctional antibody that binds MET and EGFR comprising: (a) two first polypeptides wherein both of the first polypeptides comprise the amino acid sequence of SEQ ID NO: 25, SEQ ID NO: 26, SEQ ID NO: 27, SEQ ID NO: 29, SEQ ID NO: 31, SEQ ID NO: 52, or SEQ ID NO: 53; and (b) two second polypeptides wherein both of the second polypeptides comprise the amino acid sequence of SEQ ID NO: 33, and a pharmaceutically acceptable carrier, diluent, or excipient.

Another embodiment of the present invention is a method of treating cancer, comprising administering to a patient in need thereof an effective amount of a multifunctional antibody that binds MET and EGFR comprising: (a) two first polypeptides wherein both of the first polypeptides comprise the amino acid sequence of SEQ ID NO: 25, SEQ ID NO: 26, SEQ ID NO: 27, SEQ ID NO: 29, SEQ ID NO: 31, SEQ ID NO: 52, or SEQ ID NO: 53; and (b) two second polypeptides wherein both of the second polypeptides comprise the amino acid sequence of SEQ ID NO: 33. In some embodiments of such an invention the cancer is NSCLC, SCLC, gastric cancer, colorectal cancer, cholangiocarcinoma, esophageal cancer, melanoma, uveal melanoma, renal cancer, liver cancer, bladder cancer, cervical cancer, or head and neck cancer. In some embodiments of such an invention the cancer patient is a human. In other embodiments of such an invention the patient's tumor is characterized by comprising cells having one or more KRAS mutations. In other embodiments of the present invention provides a method of treating a cancer, including administering a pharmaceutically effective amount of one of the foregoing multifunctional antibodies, or a MET and EGFR binding fragment thereof, to a patient in need thereof wherein MET and/or EGFR are expressed by the patient's tumor at a low, moderate, or high level and/or tumor or a tumor which is resistant, or has become resistant, to one or more anti-EGFR antibodies (e.g., cetuximab, panitumumab, etc.) and/or one or more small molecule inhibitors of EGFR (e.g., erlotinib), including, but not limited to, tumors harboring KRAS mutations. In various embodiments of such an invention, the method of treating a cancer wherein MET and/or EGFR are expressed by the patient's tumor at a low, moderate, or high level and/or wherein the tumor is resistant, or has become resistant, to one or more anti-EGFR antibodies (e.g., cetuximab, panitumumab, etc.) and/or one or more small molecule inhibitors of EGFR (e.g., erlotinib), including, but not limited to, tumors harboring KRAS mutations may further comprise a step of identifying the patient in need of the treatment of the cancer, prior to the step of administering the multifunctional antibody, or a MET and EGFR binding fragment thereof, to the patient by measuring the levels of MET and EGFR expressed by the patient's tumor and/or assessing whether the patient's tumor comprises cells having one or more KRAS mutations.

Table 3 below depicts the SEQ ID NOs of the amino acid sequences of scFv and scFv fusions of the present invention.

TABLE 3

| | YK-scFv | $YK_n$-scFv and anti-MET HCVR fusion | $YK_n$-scFv and anti-MET HC fusion | anti-MET HC and YK-scFv fusion |
|---|---|---|---|---|
| SEQ ID NO: | 23 | 25 | 27 | 31 |

| | H9-scFv | $H9_n$-scFv and anti-MET HCVR fusion | $H9_n$-scFv and anti-MET HC fusion | anti-MET HC and H9-scFv fusion |
|---|---|---|---|---|
| SEQ ID NO: | 24 | 26 | 29 | 52 |

When used herein in reference to a scFv, including in Table 3 above, the subscript "n" indicates that the anti-EGFR YK scFv or the anti-EGFR H9 scFv is fused to the N-terminus of the MET antibody heavy chain.

A further embodiment of the present invention is a multifunctional antibody comprising two identical first polypeptides and two identical second polypeptides wherein the amino acid sequence of the first polypeptide is SEQ ID NO: 27 or SEQ ID NO: 29 and the amino acid sequence of the second polypeptide is SEQ ID NO: 33, wherein said multifunctional antibody binds to EGFR and MET. Furthermore, in various embodiments of such invention the multifunctional antibody induces HGF-independent and EGF-independent internalization and/or degradation of cell surface MET and EGFR, respectively.

Standard molecular biology techniques are used to prepare the recombinant expression vector, transfect the host cells, select for transformants, isolated host cell lines producing a multifunctional antibody of the invention, culture these host cells and recover the antibody from the culture medium.

The present invention is also directed to host cells that express a multifunctional antibody of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells).

A multifunctional antibody of the invention can be prepared by recombinant expression of immunoglobulins in a host cell. To express an antibody recombinantly in a host cell, a host cell is transformed, transduced, infected or the like with one or more recombinant expression vectors carrying DNA fragments encoding the light chain and/or the scFv-heavy chain fusion of the multifunctional antibody. The heavy chain and the light chain may be expressed independently from different promoters to which they are operably linked in one vector or, alternatively, the heavy chain and the light chain may be expressed independently from different promoters to which they are operably linked in two vectors—one expressing the heavy chain and one expressing the light chain. Optionally, the heavy chain and light chain may be expressed in different host cells. Preferably, the recombinant antibodies are secreted into the medium in which the host cells are cultured, from which the antibodies can be recovered or purified.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., IgG$_1$, IgG$_2$, IgG$_3$ and IgG$_4$) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and/or polyoma virus.

Additionally, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, as described in Urlaub and Chasin, *Proc. Natl. Acad. Sci. USA* 77:4216-20, 1980, used with a DHFR selectable marker, e.g., as described in Kaufman and Sharp, *J. Mol. Biol.* 159:601-21, 1982], NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

Host cells can also be used to produce portions, or fragments, of intact antibodies, e.g., Fab fragments or scFv molecules by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to EGFR and MET. The molecules expressed from such truncated DNA molecules are also encompassed by the antibodies of the invention.

The invention provides a host cell comprising a nucleic acid molecule of the present invention. Preferably, a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxylapatite chromatography, gel electrophoresis, and the like. Substantially pure immunoglobulins of at least about 90%, about 92%, about 94% or about 96% homogeneity are preferred, and about 98% to about 99% or more homogeneity most preferred, for pharmaceutical uses. Once purified, partially or to homogeneity as desired, the sterile antibodies may then be used therapeutically, as directed herein.

The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated" multifunctional antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, an antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, SimplyBlue™ SafeStain (Life Technologies) or, preferably, silver stain. Isolated antibody includes the antibody in situ within recombinant cells since at least one component of the antibody's natural environment will not be present.

As used herein, "substantially pure" or "substantially purified" means a compound or species that is the predominant species present (i.e., on a molar basis it is more abundant than any other individual species in the composition). In certain embodiments, a substantially purified composition is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

In another embodiment, the present invention provides an isolated polynucleotide that encodes the amino acid sequence selected from the group consisting of SEQ ID NOs: 27, 29, and 33.

In another embodiment, the present invention provides a recombinant expression vector comprising polynucleotide that encodes the amino acid sequence selected from the group consisting of SEQ ID NOs: 27, 29, and 33.

The invention also provides any one of the foregoing anti-MET/EGFR multifunctional antibodies, or a MET and EGFR binding fragment thereof, for use in therapy.

The invention also provides any one of the foregoing anti-MET/EGFR multifunctional antibodies, or a MET and EGFR binding fragment thereof, for use in treating a cancer.

The invention also provides any one of the foregoing anti-MET/EGFR multifunctional antibodies, or a MET and EGFR binding fragment thereof, for use in treating a cancer wherein both MET and EGFR are expressed.

The invention also provides any one of the foregoing anti-MET/EGFR multifunctional antibodies, or a MET and EGFR binding fragment thereof, for use in treating NSCLC, SCLC, gastric cancer, colorectal cancer, cholangiocarcinoma, esophageal cancer, melanoma, including, but not limited to, uveal melanoma, renal cancer, liver cancer, bladder cancer, cervical cancer, or head and neck cancer.

The invention also provides a method of treating a cancer, comprising administering to a human patient in need thereof an effective amount of any one of the foregoing multifunctional antibodies, or a MET and EGFR binding fragment thereof.

The term "treating" (or "treat" or "treatment") refers to slowing, interrupting, arresting, controlling, stopping, reducing, or reversing the progression or severity of a symptom, disorder, condition, or disease, but does not necessarily involve a total elimination of all disease-related symptoms, conditions, or disorders.

The term "cancer" (or "a cancer") refers to proliferative diseases, such as lung cancer, non-small cell lung cancer (NSCLC), small cell lung cancer (SCLC), cancer of the head or neck, rectal cancer, cancer of the anal region, stomach cancer, gastric cancer, colon cancer, colorectal carcinoma (CRC), esophageal cancer, melanoma, including, but not limited to, uveal melanoma, liver cancer, cervical cancer, cancer of the bladder, cancer of the kidney or ureter, renal cell carcinoma, carcinoma of the renal pelvis, including refractory versions of any of the above cancers, or a combination of one or more of the above cancers.

The phrase "effective amount" as used herein refers to an amount necessary (at dosages and for periods of time and for the means of administration) to achieve the desired therapeutic result. An effective amount of the multifunctional antibody may vary according to factors such as the disease state, age, gender, and weight of the individual, and the ability of the antibody, or MET and EGFR binding fragment thereof, to elicit a desired response in the individual. An effective amount is also one in which any detrimental effect(s) of the antibody, or MET and EGFR binding fragment thereof, are outweighed by the therapeutically beneficial effects.

An effective amount is at least the minimal amount, but less than an overall harmful amount, of an active agent which is necessary to impart therapeutic benefit to a subject. Stated another way, an effective amount or therapeutically effective amount of an antibody of the invention is an amount which in mammals, preferably humans, reduces the number of cancer cells; reduces the tumor size; inhibits (i.e., slow to some extent or stop) cancer cell infiltration into peripheral tissues organs; inhibit (i.e., slow to some extent or stop) tumor metastasis; inhibits, to some extent, tumor growth; and/or relieves to some extent one or more of the symptoms associated with the cancer. An effective amount of an anti-MET/EGFR multifunctional antibody of the invention may be administered in a single dose or in multiple doses. Furthermore, an effective amount of an anti-MET/EGFR multifunctional antibody of the invention may be administered in multiple doses of amounts that would be less than an effective amount if not administered more than once.

As is well known in the medical arts, dosages for any one subject depends upon many factors, including the patient's size, body surface area, age, the particular compound to be administered, gender, time and route of administration, general health, and other drugs being administered concurrently. Dose may further vary depending on the type and severity of the disease. A typical dose can be, for example, in the range of about 1 mg to about 100 mg; preferably, about 2 mg to about 100 mg; more preferably, about 5 mg to about 100 mg; even more preferably, about 5 mg to about 50 mg, even more preferably, about 5 mg to about 25 mg; even more preferably, about 5 mg to about 20 mg; even more preferably, about 5 mg to about 15 mg; however, doses below or above this exemplary range are envisioned, especially considering the aforementioned factors. A daily parenteral dosage regimen can be from about 10 μg/kg to about 10 mg/kg. Progress may be monitored by periodic assessment, and the dose adjusted accordingly.

In some embodiments of the present invention, a single dose of a multifunctional antibody of the present invention may be administered intravenously for treating a cancer in an adult patient. A typical single dose for intravenous administration can be, for example, in the range of about 100 mg to about 1250 mg; preferably, about 200 mg to about 1250 mg; more preferably, about 500 mg to about 1250 mg; even more preferably, about 750 mg to about 1250 mg, even more preferably, about 800 mg to about 1250 mg; even more preferably, or most preferably about 800 mg to about 1000 mg; however, doses below or above this exemplary range are envisioned, especially considering the aforementioned factors. Alternatively, a typical single dose for intravenous administration of a multifunctional antibody of the present invention can be, for example, from about 10 mg/kg to about 20 mg/kg body weight, more preferably about 12 mg/kg to about 15 mg/kg, or even more preferably about 12 mg/kg to about 13 mg/kg. Such doses can be administered intravenously once every week, once every two weeks, once every three weeks, or once every month, for example. Progress may be monitored by periodic assessment, and the dose adjusted accordingly.

These suggested amounts of antibody are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the antibody, the particular type of antibody, the method of administration, the scheduling of administration, and other factors known to medical practitioners.

The anti-MET/EGFR multifunctional antibodies of the present invention can be used as medicaments in human medicine, administered by a variety of routes. Accordingly, the invention also provides pharmaceutical compositions comprising any one of the foregoing multifunctional antibodies, or a MET and EGFR binding fragments thereof, and a pharmaceutically acceptable carrier, diluent, or excipient. Most preferably, such compositions are for parenteral administration. The term parenteral as used herein includes intravenous, intramuscular, subcutaneous, rectal, vaginal, or intraperitoneal administration. Parenteral delivery by intravenous or intraperitoneal or subcutaneous administration is preferred. Intravenous administration is most preferred. Suitable vehicles for such administration are well known in the art.

The pharmaceutical composition typically must be sterile and stable under the conditions of manufacture and storage in the container provided, including e.g., a sealed vial, syringe or other delivery device, e.g., a pen. Therefore, pharmaceutical compositions may be sterile filtered, or otherwise made free of microbial contamination, after making the formulation.

An antibody of the invention may be administered to a human subject alone or with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents including but not limited to sodium chloride, stabilizing agents and the like are used as appropriate. Said compositions can be designed in accordance with conventional techniques disclosed in, e.g., *Remington, The Science and Practice of Pharmacy*, 19$^{th}$ Edition, Gennaro, Ed., Mack Publishing Co., Easton, Pa. (1995) which provides a compendium of formulation techniques as are generally known to practitioners. Suitable carriers for pharmaceutical compositions include any material which, when combined with an antibody of the invention, retains the molecule's activity and is non-reactive with the subject's immune system.

The following non-limiting examples illustrate various properties of the present multifunctional antibodies.

EXAMPLES

Reference Example 1

1.1. Expression and Purification of the Multifunctional Antibody NH-YK

The multifunctional antibody, NH-YK, can be expressed and purified essentially as follows. A glutamine synthetase (GS) expression vector containing the DNA of SEQ ID NO: 28 (encoding the first polypeptide having the amino acid sequence of SEQ ID NO: 27) and SEQ ID NO: 34 (encoding the light chain amino acid sequence of SEQ ID NO: 33) is used to transfect the Chinese hamster cell line, CHOK1SV (Lonza Biologics PLC, Slough, United Kingdom) by electroporation. The expression vector encodes an SV Early (Simian Virus 40E) promoter and the gene for GS. Expression of GS allows for the biochemical synthesis of glutamine, an amino acid required by the CHOK1SV cells. Post-transfection, cells undergo bulk selection with 50 μM L-methionine sulfoximine (MSX). The inhibition of GS by MSX is utilized to increase the stringency of selection. Cells with integration of the expression vector cDNA into transcriptionally active regions of the host cell genome are selected against CHOK1SV wild type cells, which express an endogenous level of GS. Transfected pools are plated at low density to allow for close-to-clonal outgrowth of stable expressing cells. The masterwells may be screened for multifunctional antibody expression and then scaled up as needed in serum-free, suspension cultures. Alternatively, bulk-selected transfectants may be subjected to single-cell cloning procedures such as Fluorescence-Activated Cell Sorting (FACS) or limited dilution and screened for multifunctional antibody expression. Once a suitable cell line is identified, it may be scaled up as needed in serum-free, suspension cultures. Clarified medium, into which the multifunctional antibody has been secreted, is applied to a Protein A affinity column that has been equilibrated with a compatible buffer, such as phosphate buffered saline (pH 7.4) or Tris buffer (pH 7.4). The column is washed to remove nonspecific binding components. The bound multifunctional antibody is eluted, for example, by pH gradient (such as 0.1 M sodium phosphate buffer pH 6.8 to 0.1 M sodium citrate buffer pH 2.5-3.0). Multifunctional antibody fractions are detected and/or collected, such as by absorbance cutting at 280 nm, SDS-PAGE or analytical size-exclusion. Soluble aggregate and multimers may be effectively removed by common techniques, including size exclusion, hydrophobic interaction, ion exchange, or hydroxyapatite chromatography. The multifunctional antibody may be concentrated and/or sterile filtered using common techniques. The purity of the multifunctional antibody after these chromatography steps is greater than 90%, preferably, greater than 98%. The multifunctional antibody may be immediately frozen at −70° C. or stored at 4° C. for several months.

1.2. Expression and Purification of the Multifunctional Antibodies, NH-H9

The multifunctional antibody, NH-H9, can be expressed and purified essentially as described above in Reference Example 1.1 except a glutamine synthetase (GS) expression vector containing the DNA of SEQ ID NO: 30 (encoding the first polypeptide having the amino acid sequence of SEQ ID NO: 29) and SEQ ID NO: 34 (encoding the light chain amino acid sequence of SEQ ID NO: 33) is used to transfect the Chinese hamster cell line, CHOK1SV (Lonza Biologics PLC, Slough, United Kingdom) by electroporation.

1.3. Expression and Purification of the Multifunctional Antibody, H9

The multifunctional antibody, H9, can be expressed and purified essentially as described above in Reference Example 1.1 except a glutamine synthetase (GS) expression vector containing a DNA encoding the first polypeptide having the amino acid sequence of SEQ ID NO: 52 and the DNA of SEQ ID NO: 34 (encoding the light chain amino acid sequence of SEQ ID NO: 33) is used to transfect the Chinese hamster cell line, CHOK1SV (Lonza Biologics PLC, Slough, United Kingdom) by electroporation.

1.4. Expression and Purification of the Multifunctional Antibody, YK

The multifunctional antibody, H9, can be expressed and purified essentially as described above in Reference Example 1.1 except a glutamine synthetase (GS) expression vector containing a DNA encoding the first polypeptide having the amino acid sequence of SEQ ID NO: 31 and the DNA of SEQ ID NO: 34 (encoding the light chain amino acid sequence of SEQ ID NO: 33) is used to transfect the Chinese hamster cell line, CHOK1SV (Lonza Biologics PLC, Slough, United Kingdom) by electroporation.

Example 1

Binding Analysis of Multifunctional Antibodies to MET and EGFR

A surface plasmon resonance biosensor such as a BIAcore® 2000, BIAcore® 3000, or a BIAcore® T100 (Biacore Life Sciences Division, GE Healthcare, Piscataway, N.J.) may be used to measure binding kinetics and affinity of antibodies such as the antibodies disclosed herein according to methods known in the art. Except as noted, all reagents and materials can be purchased from BIAcore® AB (Upsala, Sweden), and measurements may be performed at 25° C. Briefly described, samples may be dissolved in HBS-EP buffer (150 mM sodium chloride, 3 mM EDTA, 0.005% (w/v) surfactant P-20, and 10 mM N-2-hydroxyethyl-piperazine-N'-2-ethanesulfonic acid (HEPES) at pH 7.4). A CM5 chip containing immobilized protein A (which may be generated using standard NHS-EDC amine coupling) on all four flow cells (Fc) may be used to employ a capture methodology. Antibody samples can be prepared at 1 mcg/mL by dilution into running buffer initially and then their capture may be tested at flow rate 10 µl/min for 30 seconds. Based on the amount captured, the antibody concentration can be adjusted accordingly to target the capture amount between about 70 RU to 90 RU. MET-ECD or human EGFR-ECD may be prepared at final concentrations of 100, 50, 25, 12.5, 6.25, 3.13, 1.56, 0.78, 0.39 and 0 (blank) nM by dilution into running buffer. Each analysis cycle may consist of (1) capturing antibody samples on separate flow cells (Fc2, Fc3, and Fc4), (2) injection of 250 mcL (300-sec) of MET-ECD or EGFR-ECD overall Fc at 50 mcL/min, (3) return to buffer flow for 20 minutes to monitor dissociation phase, (4) regeneration of chip surfaces with a 25 mcL (30-sec) injection of glycine, pH 1.5, (5) equilibration of chip surfaces with a 25 mcL (30-sec) injection of HBS-EP+ buffer (i.e., HBS-EP buffer with 0.05% (w/v) surfactant P-20 instead of 0.005%). Data can be processed using standard double-referencing and fit to a 1:1 binding model using Biacore T100 Evaluation software, version 2.0 or Biacore T200 Evaluation software, version 1.0, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) may be calculated as from the relationship $K_D = k_{off}/k_{on}$.

Four anti-MET/EGFR multifunctional antibodies of the present invention were tested to determine their binding kinetics and binding affinity to MET-ECD and EGFR-ECD essentially as described above and the results are summarized in Tables 4 and 5 below. The antibodies NH-YK, NH-H9, H9, and YK bind both MET-ECD (Table 4) and EGFR-ECD (Table 5) with high binding affinity ($K_D$).

TABLE 4

Binding Kinetics and Affinity of multifunctional antibodies to MET-ECD

| Multifunctional Antibodies | $k_{on}$ $M^{-1}s^{-1}$ ($10^4$) | $k_{off}$ $s^{-1}$ ($10^{-5}$) | $K_D$ (nM) |
|---|---|---|---|
| NH-YK | 7.5 | 6.3 | 0.84 |
| NH-H9 | 10.5 | 7.9 | 0.75 |
| H9 | 9.5 | 10.9 | 1.15 |
| YK | 12.6 | 3.3 | 0.26 |

TABLE 5

Binding Kinetics and Affinity of multifunctional antibodies to EGFR-ECD

| Multifunctional Antibodies | $k_{on}$ $M^{-1}s^{-1}$ ($10^6$) | $k_{off}$ $s^{-1}$ ($10^{-4}$) | $K_D$ (nM) |
|---|---|---|---|
| NH-YK | 4.0 | 7.5 | 0.19 |
| NH-H9 | 1.8 | 1.8 | 0.10 |
| H9 | 0.57 | 1.8 | 0.32 |
| YK | 1.3 | 5.7 | 0.44 |

Example 2

Binding of NH-YK to Both Cell Surface MET and EGFR

The NSCLC cell line H441 (ATCC, Manassas, Va.; catalog #HTB-174) expresses both MET and EGFR on the surface. H441 cells ($6\times10^6$) may be plated onto 100 mm poly-D-lysine coated tissue culture dishes and incubated 2 days at 37° C., 5% $CO_2$. Then the cells can be treated with 100 nM control IgG4, a combination of 100 nM cetuximab and 100 nM anti-MET antibody, or 100 nM NH-YK for 20 minutes at 4° C. The cells can be washed with ice-cold DPBS and lysed using CHAPS lysis buffer with HALT protease and phosphatase inhibitors (Thermo Scientific, Rockford, Ill.). Immunoprecipitations (IP) can be performed on 600 g of each cell lysate sample using anti-MET agarose or anti-EGFR sepharose and incubated overnight at 4° C. The resin may be washed and the bound protein eluted from the resin, then loaded onto 4-20% SDS-PAGE and blotted onto nitrocellulose membranes for Western blot. The membranes may be probed for total MET or total EGFR.

Immunoprecipatation experiments performed essentially as described above, demonstrate that MET and EGFR co-immunoprecipitate after treatment with the anti-MET/EGFR multifunctional antibody NH-YK, but not after treatment with either the anti-MET antibody, cetuximab, or even a combination of anti-MET antibody and cetuximab. These data indicate that NH-YK can bind to both MET and EGFR (data not shown).

Example 3

Multifunctional Antibodies NH-YK and NH-H9 Exhibit Enhanced Avidity Binding to Cell-surface MET The NSCLC cancer cell line HCC827 has high levels of MET expression. Briefly, HCC827 cells may be removed from a cell culture flask using enzyme-free dissociation buffer and added at approximately $5\times10^5$ cells per well in a 96-well plate. Then the cells may be treated with dose titrations of unlabeled antibodies (starting at 500 nM) in combination with 5 nM Alexa488-labeled anti-MET antibody for 1 hour at 4° C. in order to determine the ability of the unlabeled antibodies to compete for binding to cell surface MET with labeled anti-MET antibody. Finally, binding of labeled anti-MET antibody may be detected by FACS.

As demonstrated by assays performed essentially as described in this Example, the anti-MET/EGFR multifunctional antibodies NH-YK and NH-H9 have demonstrably higher avidity binding than their parental anti-MET antibody (Table 6).

TABLE 6

ANTI-MET/EGFR multifunctional antibodies have increased avidity binding to HCC827 cells

| Antibody conc., (nM) | anti-EGFR Ab MFI | anti-MET Ab MFI | NH-YK MFI | NH-H9 MFI | HGF (ng/mL) |
|---|---|---|---|---|---|
| 500.00 | 65.01 | 3.03 | 3.05 | 3.08 | 25.11 |
| 100.00 | 65.05 | 4.92 | 3.49 | 4.06 | 43.73 |
| 20.00 | 65.95 | 13.50 | 4.88 | 7.43 | 53.44 |
| 4.00 | 64.30 | 35.60 | 10.03 | 18.27 | 57.41 |
| 0.80 | 64.97 | 51.77 | 27.35 | 41.01 | 57.62 |
| 0.16 | 64.96 | 59.25 | 47.81 | 54.91 | 60.22 |
| 0.03 | 65.76 | 59.04 | 55.62 | 60.31 | 61.44 |

MFI = mean fluorescence intensity as indicated by competition with Alexa 488-labeled anti-MET Ab Example 4

Anti-MET/EGFR Multifunctional Antibodies NH-YK and NH-H9 Exhibit Better Activity than Cetuximab does for Internalization and Degradation of Cell Surface EGFR Part A: The NSCLC cell line H441 expresses moderate levels of both MET and EGFR on its cell surface. Anti-MET/EGFR multifunctional antibodies may be tested for their capability of depleting cell surface MET and EGFR from H441 cells. Briefly, $1.5 \times 10^5$ cells in 2 mL culture medium may be plated per well in 6 well plates and incubated overnight at 37° C., 5% $CO_2$. Antibodies NH-YK, NH-H9 or control antibodies can be added at 50 nM to H441 cells. After overnight treatment, the cells may be removed from wells with enzyme-free dissociation buffer, washed, and then stained with labeled EGFR or MET antibodies (that recognize different epitope from multifunctional antibodies or control antibody treatments) for 1 hour. Cells are washed and measured for labeled antibody staining by FACS.

To assess the ability of the anti-MET/EGFR multifunctional antibodies NH-YK and NH-H9 to promote the degradation of MET and EGFR in vivo, assays were performed essentially as described in part A of this Example. The results from these studies demonstrate that the anti-MET/EGFR multifunctional antibodies NH-YK and NH-H9 are capable of depleting cell surface MET from H441 cells similarly to its parental anti-MET antibody. Surprisingly, though, the anti-MET/EGFR multifunctional antibodies NH-YK and NH-H9 triggered significant EGFR degradation whereas cetuximab or the combination of anti-MET antibody and cetuximab did not (Table 7).

Part B: The NSCLC cell line H1993 expresses a high level of MET and a moderate level of EGFR; the gastric cancer cell line MKN45 expresses a high level of MET and a low level of EGFR; the NSCLC cell line H441 expresses moderate levels of both MET and EGFR on its cell surface. Briefly, $5 \times 10^5$ cells in 2 mL culture medium may be plated per well in 6 well plates and incubated overnight at 37° C., 5% $CO_2$. The anti-MET/EGFR multi-functional antibodies NH-YK, NH-H9 or control antibodies may be added to the cells at 100 nM. After overnight treatment, the cells can be lysed and 15 g of each sample may be run on 4-12% BisTris gels and then blotted onto PVDF membranes. Membranes may be probed by western blotting for total EGFR, total MET, and GAPDH.

To assess the ability of the anti-MET/EGFR multifunctional antibodies NH-YK and NH-H9 to promote the degradation of MET and EGFR in vitro, assays were performed essentially as described in part B of this Example. The results from these studies demonstrate that the antibodies NH-YK and NH-H9 degrade MET from H1993, MKN45, and H441 cells similarly to the parental anti-MET antibody. However, surprisingly, the anti-MET/EGFR multifunctional antibodies NH-YK and NH-H9 trigger significant degradation of EGFR whereas cetuximab or a combination of the parental anti-MET antibody and cetuximab did not (FIG. 1).

TABLE 7

Anti-MET/EGFR multifunctional antibodies have increased internalization activity for EGFR on H441 cells

| Antibody conc., (50 nM) | AVG of MFI | hIgG4, AVG of MFI | | Std. Err |
|---|---|---|---|---|
| | | | % cell surface MET remaining | |
| hIgG4 | 77.40 | 77.40 | 100.00 | 0.08 |
| cetuximab | 76.20 | | 98.45 | 1.69 |
| anti-MET Ab | 47.44 | | 61.30 | 0.32 |
| anti-MET Ab + | | | | |
| cetuximab | 50.41 | | 65.13 | 0.10 |
| NH-H9 | 48.84 | | 63.10 | 0.07 |
| NH-YK | 44.89 | | 57.99 | 2.71 |
| | | | % cell surface EGFR remaining | |
| hIgG4 | 56.29 | 56.29 | 100.00 | 2.09 |
| cetuximab | 47.25 | | 83.95 | 0.71 |
| anti-MET Ab | 58.80 | | 104.47 | 1.42 |
| anti-MET Ab + | | | | |
| cetuximab | 50.08 | | 88.98 | 0.85 |
| NH-H9 | 17.93 | | 31.86 | 0.34 |
| NH-YK | 17.87 | | 31.74 | 0.51 |

MFI = mean fluorescence intensity;
AVG = average;
Std. Err = Standard Error

Example 5

Anti-MET/EGFR Multifunctional Antibodies NH-YK and NH-H9 Block Both MET and EGFR Activation Part A: NSCLC cancer cell line H596 has been shown to be resistant to the growth inhibitory effects of EGFR inhibitors in the presence of HGF. Thus, this cell line can be used to determine if antibodies can inhibit the proliferation of H596 cells in the presence of HGF. Briefly described, $3 \times 10^3$ cells/well in 100 μL culture medium may be plated in 96 well plates and incubated overnight at 37° C., 5% $CO_2$. The anti-MET/

EGFR multifunctional antibodies NH-YK and NH-H9 or control antibodies may be diluted 1:3 in serum-free culture medium starting from 100 nM (final) and added in combination with 50 ng/mL HGF (final) in 50 µL as 4× concentrations to the H596 cells. At the end of an additional 6 days of cell growth, plates may be equilibrated to room temperature for 30 minutes and 100 µL/well of CellTiter-Glo® reagent (Promega Corp., Fitchburg, Wis.) can be added. Cell viability can be determined by measuring luminescence.

Assays performed essentially as described in this Example demonstrate that the anti-MET/EGFR multifunctional antibodies NH-YK and NH-H9 inhibit in vitro proliferation of H596 stimulated with HGF better than cetuximab or a combination of the parental anti-MET antibody and cetuximab.

TABLE 8

Anti-MET/EGFR multifunctional antibodies exhibit superior activity than the combination of individual antibodies in inhibition of H596 proliferation in the presence of HGF

| Antibody conc. (nM) | hIgG4 AVG | Std. Err | cetuximab AVG | Std. Err | anti-MET Ab AVG | Std. Err |
|---|---|---|---|---|---|---|
| 100 | 132.3 | 1.1 | 129.2 | 4.0 | 108.6 | 3.1 |
| 33.3 | 130.9 | 0.7 | 127.4 | 1.8 | 112.8 | 1.4 |
| 11.1 | 138.6 | 1.9 | 132.6 | 0.2 | 121.0 | 3.1 |
| 3.7 | 137.0 | 1.6 | 129.7 | 2.7 | 121.4 | 1.8 |
| 1.2 | 138.5 | 2.5 | 132.0 | 4.7 | 128.2 | 0.0 |
| 0.4 | 138.9 | 0.9 | 128.6 | 2.4 | 129.8 | 1.8 |
| 0.0 | 100.0 | 0.6 | | | | |

| Antibody conc. (nM) | anti-MET Ab + cetuximab AVG | Std. Err | NH-YK AVG | Std. Err | NH-H9 AVG | Std. Err |
|---|---|---|---|---|---|---|
| 100 | 98.1 | 3.1 | 101.5 | 0.4 | 101.6 | 0.6 |
| 33.3 | 108.0 | 1.2 | 101.3 | 1.7 | 101.8 | 1.0 |
| 11.1 | 116.1 | 2.6 | 107.1 | 3.0 | 104.8 | 0.8 |
| 3.7 | 116.7 | 1.6 | 103.9 | 1.2 | 102.6 | 1.9 |
| 1.2 | 125.0 | 0.6 | 108.1 | 1.3 | 101.9 | 1.0 |
| 0.4 | 131.8 | 1.5 | 113.4 | 0.9 | 106.7 | 3.1 |
| 0.0 | | | | | | |

| Antibody only, (100 nM) | AVG | Std. Err |
|---|---|---|
| hIgG4 | 102.51 | 1.06 |
| cetuximab | 91.35 | 0.71 |
| anti-MET Ab | 92.33 | 0.98 |
| anti-MET Ab + cetuximab | 94.03 | 0.07 |
| NH-YK | 94.10 | 0.38 |
| NH-H9 | 91.55 | 0.75 |
| HGF, 50 ng/mL | 136.66 | 0.48 |

Abbreviations:
AVG = average % of cell viability;
Std. Err = Standard Error

Part B: Other tumor cell lines may also be used to determine if anti-MET/EGFR multifunctional antibodies have superior activity than the combination of two individual antibodies in inhibiting the proliferation of tumor cells in vitro assays. For example, colon cancer cell line GEO has been shown to be driven by EGFR ligand autocrine activation despite having a medium level of MET expression. The lung cancer cell line H1666 has EGFR gene amplification and its proliferation has been shown to be driven by EGFR activation. Both NSCLC cell lines H1993 and EBC-1 express a high level of MET, due to MET gene amplification, and a moderate level of EGFR.

Assays performed essentially as described in this Example demonstrate that the anti-MET/EGFR multifunctional antibodies NH-YK and NH-H9 inhibit in vitro proliferation of the colon cancer cell line GEO better than cetuximab and, surprisingly, even more potently than the combination of their parental anti-MET antibody and cetuximab (Table 9).

TABLE 9

Anti-MET/EGFR multifunctional antibodies exhibit superior activity than the combination of individual antibodies in inhibiting proliferation of GEO

| Antibody (nM) | hIgG4 AVG | Std. Err | cetuximab AVG | Std. Err | anti-MET Ab AVG | Std. Err |
|---|---|---|---|---|---|---|
| 100 | 102.64 | 0.54 | 46.39 | 1.55 | 101.71 | 0.39 |
| 33.33 | 102.43 | 0.33 | 50.06 | 0.55 | 101.48 | 0.66 |
| 11.11 | 102.43 | 0.11 | 57.67 | 1.27 | 102.82 | 0.66 |
| 3.70 | 102.22 | 1.12 | 67.23 | 0.68 | 103.03 | 0.58 |
| 1.23 | 103.80 | 0.45 | 73.63 | 2.71 | 103.42 | 0.55 |
| 0.41 | 102.56 | 1.08 | 77.70 | 2.46 | 103.42 | 0.22 |
| 0.14 | 103.30 | 1.66 | 89.99 | 5.56 | 104.67 | 0.33 |
| 0.05 | 103.00 | 1.40 | 100.83 | 0.80 | 105.67 | 0.41 |
| 0.02 | 103.42 | 1.11 | 101.64 | 0.93 | 103.90 | 1.28 |
| 0.00 | 100.00 | 0.33 | | | | |

| Antibody (nM) | anti-MET Ab + cetuximab AVG | Std. Err | NH-YK AVG | Std. Err | NH-H9 AVG | Std. Err |
|---|---|---|---|---|---|---|
| 100 | 57.93 | 0.52 | 46.15 | 1.67 | 42.65 | 0.96 |
| 33.33 | 61.99 | 2.02 | 45.05 | 1.03 | 41.33 | 1.31 |
| 11.11 | 69.07 | 2.36 | 44.44 | 0.57 | 43.99 | 0.44 |
| 3.70 | 76.49 | 1.58 | 47.99 | 0.79 | 45.52 | 1.05 |
| 1.23 | 77.92 | 0.99 | 47.09 | 0.76 | 44.21 | 1.11 |
| 0.41 | 92.10 | 4.98 | 51.33 | 0.80 | 47.07 | 0.65 |
| 0.14 | 103.72 | 1.57 | 61.90 | 1.74 | 59.98 | 1.30 |
| 0.05 | 104.32 | 0.41 | 77.54 | 1.87 | 76.05 | 1.52 |
| 0.02 | 104.90 | 0.55 | 103.62 | 2.22 | 102.97 | 1.04 |
| 0.00 | | | | | | |

Abbreviations:
AVG = average % of cell viability;
Std. Err = Standard Error

Similarly, the results shown in Table 10 demonstrate that the anti-MET/EGFR multifunctional antibodies NH-YK, NH-H9, and H9 each inhibits H1666 proliferation better than cetuximab and more potently than the combination of the parent anti-MET antibody and cetuximab.

TABLE 10

Anti-MET/EGFR multifunctional antibodies exhibit superior activity than the combination of individual antibodies in the inhibition of H1666 proliferation

| Antibody conc., (nM) | hIgG4 AVG | Std. Err | cetuximab AVG | Std. Err | anti-MET Ab AVG | Std. Err |
|---|---|---|---|---|---|---|
| 100 | 94.45 | 0.92 | 30.60 | 0.36 | 101.25 | 1.63 |
| 33.33 | 103.42 | 2.64 | 35.13 | 1.17 | 102.15 | 2.90 |
| 11.11 | 104.25 | 2.50 | 41.65 | 0.63 | 105.58 | 2.99 |
| 3.70 | 100.34 | 0.46 | 49.31 | 1.96 | 106.48 | 1.57 |
| 1.23 | 101.46 | 2.01 | 56.26 | 0.47 | 103.49 | 1.48 |
| 0.41 | 103.94 | 1.53 | 68.71 | 1.40 | 105.72 | 1.99 |
| 0.14 | 104.85 | 2.46 | 84.94 | 3.16 | 101.01 | 1.33 |
| 0.05 | 104.24 | 1.46 | 97.56 | 1.50 | 105.35 | 2.11 |
| 0.02 | 108.89 | 2.07 | 102.80 | 1.80 | 104.50 | 2.24 |
| 0.00 | 100.00 | 0.47 | | | | |

TABLE 10-continued

Anti-MET/EGFR multifunctional antibodies exhibit superior activity than the combination of individual antibodies in the inhibition of H1666 proliferation

| Anti-body conc., (nM) | Anti-MET Ab + cetuximab AVG | Std. Err | NH-YK AVG | Std. Err | NH-H9 AVG | Std. Err | H9 AVG | Std. Err |
|---|---|---|---|---|---|---|---|---|
| 100 | 36.78 | 0.73 | 26.36 | 0.14 | 23.11 | 0.27 | 28.02 | 0.25 |
| 33.33 | 42.61 | 0.66 | 27.94 | 0.39 | 24.12 | 0.29 | 31.22 | 1.43 |
| 11.11 | 48.24 | 0.59 | 31.92 | 0.18 | 26.58 | 0.40 | 34.67 | 0.66 |
| 3.70 | 53.18 | 1.57 | 36.86 | 0.61 | 31.64 | 0.52 | 41.65 | 0.14 |
| 1.23 | 63.92 | 1.76 | 45.62 | 0.96 | 38.65 | 0.75 | 49.45 | 0.40 |
| 0.41 | 70.46 | 0.34 | 65.52 | 2.92 | 52.90 | 0.75 | 58.90 | 1.11 |
| 0.14 | 81.73 | 1.58 | 87.22 | 3.16 | 77.78 | 2.82 | 79.34 | 2.48 |
| 0.05 | 96.94 | 1.74 | 105.13 | 3.84 | 100.45 | 2.88 | 96.50 | 1.02 |
| 0.02 | 103.30 | 1.02 | 106.30 | 2.88 | 104.51 | 1.19 | 99.45 | 2.59 |
| 0.00 | | | | | | | | |

Abbreviations:
AVG = average % of cell viability;
Std. Err = Standard Error

Similarly, the results shown in Table 11 demonstrate that the anti-MET/EGFR multifunctional antibodies NH-YK and NH-H9 each inhibit H1993 (Table 11) and EBC-1 (Table 12) proliferation as well as or better than the combination of their parental anti-MET antibody and cetuximab.

TABLE 11

Anti-MET/EGFR multifunctional antibodies exhibit superior activity than the combination of individual antibodies in inhibition of H1993 proliferation

| Antibody conc., (nM) | hIgG4 AVG | Std. Err | cetuximab AVG | Std. Err | anti-MET Ab AVG | Std. Err |
|---|---|---|---|---|---|---|
| 100 | 98.68 | 2.39 | 95.77 | 1.07 | 53.17 | 1.11 |
| 33.33 | 101.50 | 1.91 | 102.27 | 2.01 | 51.66 | 0.75 |
| 11.11 | 102.77 | 1.47 | 101.18 | 1.95 | 52.92 | 0.41 |
| 3.70 | 102.53 | 1.41 | 100.52 | 1.08 | 57.39 | 1.31 |
| 1.23 | 99.73 | 0.63 | 98.61 | 0.28 | 84.82 | 0.93 |
| 0.41 | 103.23 | 0.02 | 97.18 | 1.78 | 98.80 | 1.71 |
| 0.14 | 103.29 | 0.33 | 99.45 | 2.35 | 99.69 | 0.98 |
| 0.05 | 102.09 | 1.01 | 96.62 | 1.79 | 100.67 | 2.36 |
| 0.02 | 100.28 | 1.18 | 97.48 | 2.79 | 99.77 | 0.56 |
| 0.00 | 100.00 | 0.63 | | | | |

| Antibody conc., (nM) | Anti-MET Ab + cetuximab AVG | Std. Err | NH-YK AVG | Std. Err | NH-H9 AVG | Std. Err |
|---|---|---|---|---|---|---|
| 100 | 47.47 | 0.76 | 40.83 | 0.57 | 36.90 | 0.97 |
| 33.33 | 47.95 | 0.76 | 42.08 | 1.18 | 38.38 | 0.30 |
| 11.11 | 49.33 | 0.74 | 44.42 | 1.37 | 40.71 | 0.97 |
| 3.70 | 53.12 | 2.03 | 51.21 | 0.96 | 44.22 | 0.82 |
| 1.23 | 75.00 | 1.04 | 84.69 | 1.33 | 75.02 | 0.82 |
| 0.41 | 96.13 | 2.16 | 94.11 | 0.79 | 94.40 | 0.45 |
| 0.14 | 99.82 | 1.74 | 96.67 | 1.70 | 99.09 | 1.20 |
| 0.05 | 100.80 | 1.78 | 98.77 | 1.20 | 100.26 | 0.99 |
| 0.02 | 100.84 | 0.76 | 99.43 | 0.19 | 100.60 | 1.43 |
| 0.00 | | | | | | |

Abbreviations:
AVG = average % of cell viability;
Std. Err = Standard Error

TABLE 12

Anti-MET/EGFR multifunctional antibodies exhibit superior activity than the combination of individual antibodies in inhibition of EBC-1 proliferation

| Antibody conc., (nM) | hIgG4 AVG | Std. Err | cetuximab AVG | Std. Err | anti-MET Ab AVG | Std. Err |
|---|---|---|---|---|---|---|
| 100 | 105.35 | 1.61 | 107.55 | 1.27 | 43.38 | 0.14 |
| 33.33 | 102.82 | 0.74 | 105.74 | 1.31 | 38.11 | 0.57 |
| 11.11 | 102.08 | 0.63 | 105.58 | 0.98 | 37.24 | 0.55 |
| 3.70 | 103.72 | 1.19 | 106.17 | 1.48 | 35.75 | 0.87 |
| 1.23 | 103.53 | 2.28 | 106.03 | 0.80 | 38.84 | 0.44 |
| 0.41 | 103.48 | 0.72 | 105.02 | 1.70 | 80.23 | 1.47 |
| 0.14 | 100.42 | 1.09 | 103.51 | 0.57 | 99.04 | 1.21 |
| 0.05 | 100.00 | 1.96 | 100.73 | 0.95 | 102.58 | 0.54 |
| 0.02 | 102.36 | 0.92 | 102.02 | 1.88 | 102.25 | 0.77 |
| 0.00 | 100.00 | 0.38 | | | | |

| Antibody conc., (nM) | anti-MET Ab + cetuximab AVG | Std. Err | NH-YK AVG | Std. Err | NH-H9 AVG | Std. Err |
|---|---|---|---|---|---|---|
| 100 | 40.73 | 0.80 | 34.95 | 0.22 | 22.34 | 0.27 |
| 33.33 | 36.25 | 1.20 | 30.65 | 0.19 | 21.30 | 0.42 |
| 11.11 | 34.08 | 0.42 | 30.15 | 0.47 | 21.15 | 0.58 |
| 3.70 | 33.54 | 0.80 | 33.04 | 0.90 | 22.43 | 0.37 |
| 1.23 | 35.60 | 0.50 | 46.98 | 1.11 | 24.23 | 0.43 |
| 0.41 | 73.46 | 0.64 | 91.82 | 0.83 | 79.44 | 0.82 |
| 0.14 | 101.37 | 1.06 | 97.62 | 1.29 | 97.02 | 1.89 |
| 0.05 | 102.92 | 0.80 | 102.14 | 1.96 | 100.50 | 1.21 |
| 0.02 | 101.88 | 1.16 | 101.86 | 1.82 | 101.03 | 0.65 |
| 0.00 | | | | | | |

Abbreviations:
AVG = average % of cell viability;
Std. Err = Standard Error

Example 6

Anti-MET/EGFR Multifunctional Antibodies NH-YK and NH-H9 Induce Apoptosis

The gastric cancer cell line MKN45 can be used to assay apoptosis induced by antibodies. Briefly, $3 \times 10^3$ cells/well in 80 µL culture medium may be plated in 96 well plates and incubated overnight at 37° C., 5% $CO_2$. CellEvent™ reagent (Life Technologies, Carlsbad, Calif.) may be diluted in cell culture medium and added at 10 µL per well. NH-YK, NH-H9 or control antibodies were added as 10× concentrations at 10 µL to MKN45 cells for final concentrations of 100 nM. The caspase-3/7 positive cells may be measured in real-time by INCUCYTE™ Kinetic Imaging System (Essen Bioscience, Ann Arbor, Mich.) with 3 hours intervals at 37° C., 5% $CO_2$ for a total of 120 hours.

As determined by performance of assays essentially as described in this Example, the anti-MET/EGFR multifunctional antibodies NH-YK and NH-H9 each induce greater apoptosis in vitro in MKN45 than a combination of the parental MET Ab and cetuximab (Table 13). In addition, in assays performed essentially as described in this Example, NH-YK induces MKN45 apoptosis to a greater extent than the combination of one-armed 5D5 and erlotinib (data not shown).

TABLE 13

MKN45 Apoptosis assay

| Antibody conc., (100 nM) | 24 hr AVG | 24 hr Std. Err | 48 hr AVG | 48 hr Std. Err | 72 hr AVG | 72 hr Std. Err |
|---|---|---|---|---|---|---|
| untreated | 100.00 | 2.92 | 100.00 | 10.14 | 100.00 | 13.83 |
| hIgG4 | 83.60 | 8.92 | 106.20 | 3.55 | 111.25 | 13.78 |
| cetuximab | 73.56 | 4.69 | 121.70 | 26.26 | 102.24 | 10.34 |
| Anti-MET Ab | 100.35 | 7.27 | 222.81 | 28.70 | 275.40 | 21.16 |
| Anti-MET Ab + cetuximab | 126.73 | 22.78 | 235.60 | 29.73 | 292.40 | 23.35 |
| NH-YK | 114.20 | 9.96 | 291.31 | 19.04 | 393.83 | 43.63 |
| NH-H9 | 94.60 | 10.59 | 243.82 | 35.58 | 361.13 | 9.04 |

| Antibody conc., (100 nM) | 96 hr AVG | 96 hr Std. Err | 120 hr AVG | 120 hr Std. Err |
|---|---|---|---|---|
| untreated | 100.00 | 13.48 | 100.00 | 7.55 |
| hIgG4 | 91.24 | 10.61 | 108.28 | 12.02 |
| cetuximab | 107.11 | 3.56 | 127.04 | 14.16 |
| Anti-MET Ab | 286.63 | 32.84 | 353.84 | 30.08 |
| Anti-MET Ab + cetuximab | 326.83 | 32.56 | 386.84 | 19.08 |
| NH-YK | 446.24 | 28.10 | 557.79 | 32.44 |
| NH-H9 | 434.42 | 2.87 | 515.31 | 13.63 |

Abbreviations:
AVG = average % increase of cell apoptosis;
Std. Err = Standard Error

Example 7

Anti-MET/EGFR Multifunctional Antibody NH-YK Restores Erlotinib Sensitivity of Tumor Cells in the Presence of HGF The NSCLC cancer cell line HCC827 has EGFR gene amplification and high MET expression. HCC827 cells are sensitive to erlotinib treatment, but become resistant to erlotinib treatment in the presence of HGF. Briefly, $3 \times 10^3$ cells/well in 100 µL culture medium may be plated in 96 well plates and incubated overnight at 37° C., 5% $CO_2$. NH—YK or control antibodies (hIgG4) can be added to cells for 1 hour followed by addition of erlotinib and/or HGF for final concentrations of 50 nM antibody, 50 ng/mL HGF, and 1 µM erlotinib. At the end of an additional 3 days of cell growth at 37° C. under 95% relative humidity and 5% (v/v) $CO_2$, plates may be equilibrated to room temperature for 30 minutes and 100 µL/well of CellTiter-Glo® reagent (Promega Corp.) added. The plates may be shaken for two minutes on an orbital shaker to mix contents and then left to incubate at room temperature for 10 minutes to stabilize the luminescent signal. Cell viability may be determined by measuring luminescence.

As determined by performance of assays essentially as described in this Example, the antibody NH-YK is able to restore erlotinib sensitivity of HCC827 cells in vitro in the presence of HGF better than the parental anti-MET antibody in combination with cetuximab (Table 14).

TABLE 14

Anti-MET/EGFR multifunctional antibody NH-YK has superior activity than a combination of individual antibodies in restoring HCC827 sensitivity to erlotinib in the presence of HGF

| Antibody conc., (50 nM) | untreated | Erlotinib, 1 µM | Erlotinib + H 50 ng/mL | Erlotinib + H + hIgG4 |
|---|---|---|---|---|
| AVG | 101.27 | 17.98 | 80.00 | 85.14 |
| Std. Err | 2.26 | 0.20 | 3.95 | 1.39 |

| Antibody conc., (50 nM) | Erlotinib + H + cetuximab | Erlotinib + H + anti-MET Ab | Erlotinib + H + anti-METAb + cetuximab | Erlotinib + H + NH-YK |
|---|---|---|---|---|
| AVG | 102.76 | 46.35 | 61.33 | 27.25 |
| Std. Err | 0.86 | 0.65 | 1.59 | 1.01 |

Abbreviations:
AVG = average % of cell viability;
Std. Err = Standard Error;
H = HGF

Example 8

Anti-MET/EGFR Multifunctional Antibody, NH-YK, Restores B-Raf Inhibitor, PLX4032, Sensitivity of HT-29 Cells Treated with HGF and EGF The colon cancer cell line HT-29 has a B-Raf mutation and is sensitive to the B-Raf inhibitor PLX4032. HT-29 cells become resistant to PLX4032 or pan-Raf inhibitor treatment upon HGF and EGF stimulation. Anti-MET/EGFR multifunctional antibodies may be tested for their ability to restore PLX4032 inhibitor sensitivity of HT-29 cells treated with HGF and EGF. Briefly, $3 \times 10^3$ cells/well in 100 µL culture medium may be plated in 96 well plates and incubated overnight at 37° C., 5% $CO_2$. Antibody NH-YK, PLX4032, HGF, EGF, positive controls, and negative controls were diluted in serum-free culture medium and added to HT-29 cells in 50 µL as 4× concentrations. The final concentrations of reagents may be: 50 nM for antibodies, 50 ng/mL for HGF and EGF, and 1:5 dilutions of PLX4032 starting at 1 µM. At the end of an additional 5 days of cell growth, plates may be equilibrated to room temperature for 30 minutes and 100 µL per well of CellTiter-Glo® reagent (Promega Corp.) may be added. Cell viability can be determined by measuring luminescence.

As determined by performance of assays essentially as described in this Example antibody NH-YK is able to restore PLX4032 sensitivity of HT-29 cells treated with HGF and EGF (Table 15). In addition, antibody NH-YK is superior to the combination of the parental anti-MET antibody and cetuximab in restoring lapatinib (i.e., a EGFR/HER-2 inhibitor) sensitivity in FaDu cells (Table 16).

TABLE 15

Antibody NH-YK has superior activity than the combination of individual antibodies in restoring HT-29 sensitivity to B-Raf inhibitor PLX4032 in the presence of HGF and EGF

| PLX conc., (nM) | PLX AVG | PLX Std. Err | PLX + H + E AVG | PLX + H + E Std. Err | PLX + H + E + hIgG4 AVG | PLX + H + E + hIgG4 Std. Err | PLX + H + E + cetuximab AVG | PLX + H + E + cetuximab Std. Err |
|---|---|---|---|---|---|---|---|---|
| 1000 | 33.67 | 0.19 | 104.02 | 0.58 | 108.76 | 0.64 | 103.80 | 2.43 |
| 200.00 | 56.66 | 0.36 | 120.67 | 1.65 | 124.38 | 4.18 | 121.05 | 1.36 |
| 40.00 | 83.14 | 0.18 | 122.51 | 1.39 | 124.52 | 1.61 | 123.21 | 1.19 |
| 8.00 | 97.63 | 1.05 | 120.42 | 0.51 | 125.81 | 0.31 | 124.51 | 0.44 |
| 1.60 | 99.92 | 0.94 | 117.09 | 1.98 | 116.77 | 2.15 | 127.26 | 0.76 |
| 0.32 | 101.11 | 1.13 | 113.02 | 1.57 | 120.78 | 1.56 | 125.35 | 2.78 |
| 0.00 | 100.00 | 1.01 | | | | | | |

| PLX conc., (nM) | PLX + H + E + anti-MET Ab AVG | PLX + H + E + anti-MET Ab Std.Err | PLX + H + E + anti-MET Ab + cetuximab AVG | PLX + H + E + anti-MET Ab + cetuximab Std. Err | PLX + H + E + NH-YK AVG | PLX + H + E + NH-YK Std. Err |
|---|---|---|---|---|---|---|
| 1000 | 110.65 | 2.28 | 97.86 | 1.41 | 39.98 | 0.89 |
| 200.00 | 120.52 | 1.18 | 116.73 | 1.20 | 59.53 | 0.94 |
| 40.00 | 122.38 | 0.19 | 121.34 | 0.65 | 85.59 | 1.03 |
| 8.00 | 123.57 | 1.94 | 122.98 | 0.70 | 98.74 | 0.86 |
| 1.60 | 126.02 | 0.86 | 125.28 | 0.50 | 100.39 | 0.11 |
| 0.32 | 123.46 | 3.30 | 124.17 | 0.31 | 101.93 | 1.59 |
| 0.00 | | | | | | |

Abbreviations:
PLX = PLX4032;
AVG = average % of cell viability;
Std. Err = Standard Error;
H = HGF (50 ng/mL);
E = EGF (50 ng/mL)
All antibodies at 50 nM

TABLE 16

Anti-MET/EGFR multifunctional antibodies NH-YK and NH-H9 have superior activity than the combination of individual antibodies in restoring FaDu sensitivity to lapatinib in the presence of HGF

| | % of cell viability | | | | | | |
|---|---|---|---|---|---|---|---|
| lapatinib, µM | lapatinib alone | lapatinib + H | lapatinib + H + cetuximab | lapatinib + H + anti-MET | lapatinib + H + cetuximab + anti-MET | lapatinib + H + NH-H9 | lapatinib + H + NH-YK |
| 0 | 95.99 | 154.12 | 139.07 | 130.33 | 98.43 | 59.67 | 60.33 |
| 0.001 | 99.49 | 154.06 | 151.14 | 128.70 | 98.47 | 64.58 | 62.16 |
| 0.003 | 101.04 | 165.69 | 155.31 | 158.30 | 111.36 | 63.61 | 56.71 |
| 0.01 | 95.77 | 157.19 | 146.42 | 143.19 | 107.71 | 53.75 | 53.64 |
| 0.03 | 68.82 | 150.88 | 140.30 | 127.18 | 92.73 | 53.60 | 53.56 |
| 0.1 | 45.42 | 142.78 | 131.75 | 102.62 | 73.76 | 42.42 | 48.89 |
| 0.3 | 32.49 | 131.23 | 120.62 | 79.03 | 64.03 | 38.82 | 45.47 |
| 1 | 26.85 | 112.89 | 104.69 | 60.76 | 57.14 | 33.93 | 37.68 |
| 3 | 18.52 | 15.06 | 12.15 | 15.37 | 10.44 | 20.42 | 29.46 |
| 10 | 17.07 | 9.65 | 6.54 | 9.05 | 7.41 | 20.85 | 17.59 |

H = HGF (50 ng/ml); all antibodies at 50 nM

| | % of cell viability | | | | | | |
|---|---|---|---|---|---|---|---|
| lapatinib, µM | lapatinib alone | lapatinib + E | lapatinib + E + cetuximab | lapatinib + E + anti-MET | lapatinib + E + cetuximab + anti-MET | lapatinib + E + NH-H9 | lapatinib + E + NH-YK |
| 0 | 102.84 | 145.35 | 136.60 | 144.82 | 120.07 | 90.91 | 110.53 |
| 0.001 | 109.28 | 149.73 | 145.86 | 155.81 | 132.52 | 106.86 | 118.84 |
| 0.003 | 108.81 | 170.83 | 156.56 | 163.50 | 146.05 | 108.79 | 115.48 |
| 0.01 | 78.67 | 158.71 | 149.86 | 147.32 | 154.82 | 90.88 | 109.72 |

TABLE 16-continued

Anti-MET/EGFR multifunctional antibodies NH-YK and NH-H9 have superior activity than the combination of individual antibodies in restoring FaDu sensitivity to lapatinib in the presence of HGF

| 0.03 | 69.43 | 160.76 | 150.95 | 148.64 | 122.95 | 65.99 | 102.30 |
|------|-------|--------|--------|--------|--------|-------|--------|
| 0.1  | 45.64 | 152.45 | 101.10 | 143.07 | 101.54 | 42.00 | 62.87  |
| 0.3  | 32.47 | 161.37 | 47.58  | 137.03 | 56.25  | 33.46 | 40.24  |
| 1    | 26.27 | 141.20 | 31.90  | 128.06 | 36.16  | 29.66 | 27.80  |
| 3    | 18.99 | 37.11  | 21.17  | 18.19  | 23.48  | 18.10 | 19.41  |
| 10   | 19.62 | 21.39  | 17.61  | 15.87  | 22.55  | 14.88 | 7.06   |

E = EGF (50 ng/ml); all antibodies at 50 nM

Example 9

Degradation of MET and EGFR in Mouse Xenograft Models

The ability of anti-MET/EGFR multifunctional antibodies to promote the degradation of MET and EGFR in vivo may be assessed in mice bearing H441 (NSCLC) and MKN45 (gastric carcinoma) xenograft tumors according to methods well-known in the art.

Administration of the antibody NH-YK at two different dose levels (10 and 27 mg/kg) induced degradation of MET at comparable levels to the combination of the parental anti-MET antibody and cetuximab (both dosed at 20 mg/kg) 48 hours post-dosing in H441 xenografts. In contrast, the combination of the parental anti-MET antibody and cetuximab (both dosed at 20 mg/kg) failed to induce EGFR degradation when compared to PBS-treated control animals in the same xenograft model. Surprisingly, the administration of antibody NH-YK triggered significant EGFR degradation when compared to either PBS-treated or the parental anti-MET antibody and cetuximab-treated (both dosed at 20 mg/kg) mice. Similarly, in animals bearing MKN45 gastric xenografts, antibody NH-YK promoted equivalent degradation of MET but surprisingly much greater degradation of EGFR when compared to the combination of the parental anti-MET antibody and cetuximab (both dosed at 20 mg/kg).

Example 10

Inhibition of Tumor Growth in Mouse Xenograft Models for NSCLC (H1993, H441, EBC-1) and Gastric Cancer Female athymic nude mice age 6- to 7-weeks old are available commercially, including from Harlan Laboratories (Indianapolis, Ind.). The mice are allowed to acclimate for one week and fed ad libitum on a normal low fat (4.5%) diet, which may be continued for the duration of the study. Tumor cells are available for purchase from ATCC and may be cultured in cell culture media such as RPMI 1640 (Life Technologies) with L-glutamine, 25 mM HEPES supplemented with 10% FBS and 1 mM Na Pyruvate. Cells may be detached, washed with serum free medium and then resuspended at a final concentration of $50 \times 10^6$ cells/mL in serum free RPMI 1640. Tumor cells, approximately $5 \times 10^6$ may be injected subcutaneously in the rear flank of subject mice in a 1:1 mixture of serum free growth medium and Matrigel (Becton Dickinson, Bedford, Mass.). Tumor and body weight measurements are performed twice weekly. Prior to treatment, mice can be randomized based on tumor size using a randomization algorithm. Treatments may be started when the average tumor volume reaches 100 mm³. The randomized mice were separated into different groups and dosed with antibodies through tail vein injection once a week.

All test or control antibodies are prepared in phosphate Buffered Saline (PBS) prior to dose. Tumor size may be determined by caliper measurements. Tumor volume (mm³) may be estimated from the formula $A^2 \times B \times 0.536$, where A is the smaller and B is the larger of perpendicular diameters. Tumor volume data can be transformed to a log scale to equalize variance across time and treatment groups. Log volume data can be analyzed with two-way repeated measures ANOVA by time and treatment using SAS PROC MIXED software (SAS Institutes Inc, Cary, N.C.). Treatment groups are compared with the specified control group at each time point.

Figure 2:
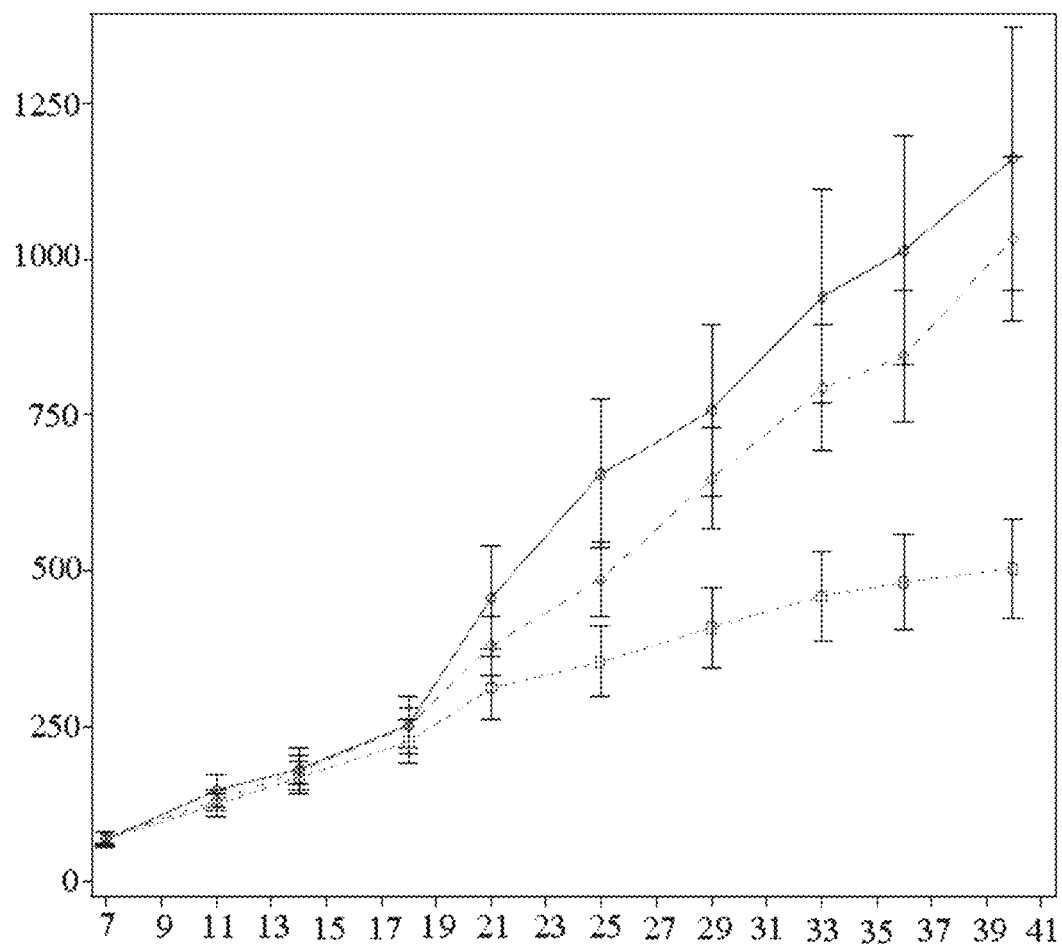
FIG. 2 is a graph showing that administration of the anti-MET/EGFR multifunctional antibody NH-YK results in a significantly greater decrease in tumor volume (T/C % of 28.5%, p<0.001) in a H1993 mouse xenograft model as compared to administration of a vehicle control or a combination of the parental anti-Met antibody and cetuximab (T/C % of 86.1%).
Figure 3:
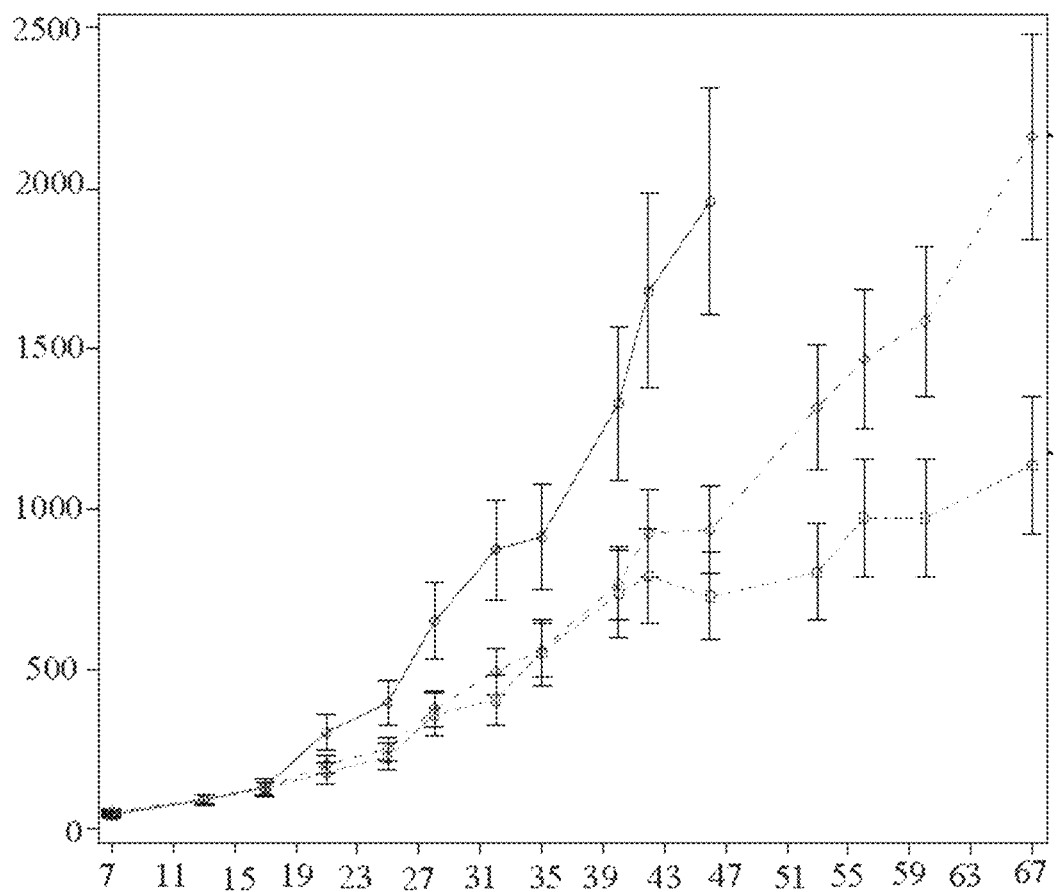
FIG. 3 is a graph showing that administration of the anti-MET/EGFR multifunctional antibody NH-YK results in a significantly greater decrease in tumor volume (T/C % of 28.5%, p<0.001) in a H441 mouse xenograft model as compared to administration of a vehicle control or a combination of the parental anti-Met antibody and cetuximab.

Part A: Immunodeficient mice bearing H1993 NSCLC xenografts were generated as described above in this Example and treated with either vehicle control, the antibody NH-YK, or the combination of the parental MET antibody plus cetuximab once a week for 5 consecutive weeks. The combination of the parental MET antibody and cetuximab (both dosed at 20 mg/kg) resulted in a percentage of the average treated-tumor-volume divided by the average vehicle-control-tumor-volume (T/C %) value of 86.1% while an equimolar dose of antibody NH-YK (27 mg/kg) resulted in a significantly greater decrease in tumor volume (T/C % of 28.5%, p<0.001) (FIG. 2). When tested in H441 xenografts, the antibody NH-YK also showed superior efficacy when compared to either the vehicle control or the combination of the parental MET antibody and cetuximab (FIG. 3).

Figure 4:
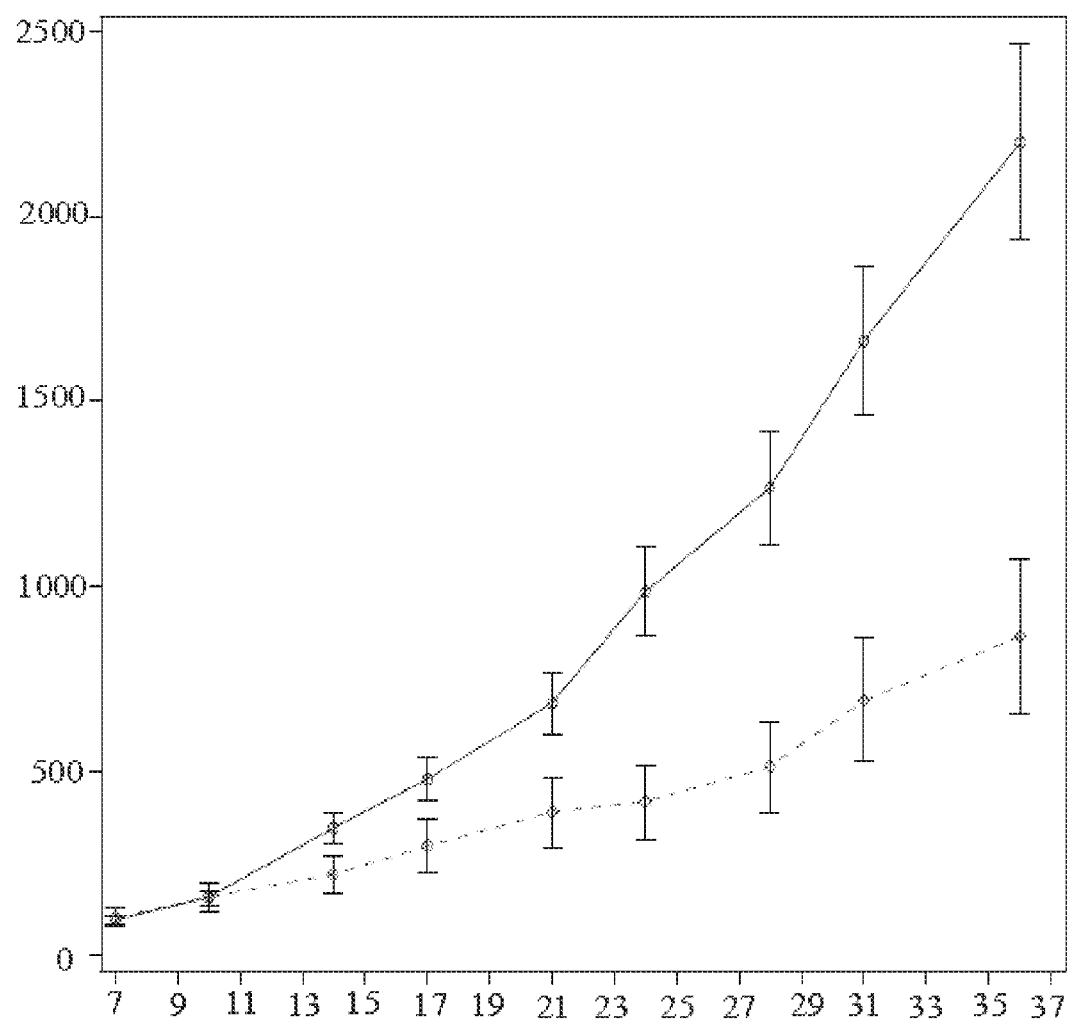
FIG. 4 is a graph showing that administration of the anti-MET/EGFR multifunctional antibody NH-YK results in a significantly greater decrease in tumor volume (T/C % of 32.9% (p<0.001)) in a EBC-1 NSCLC mouse xenograft model as compared to administration of a vehicle control.

Part B: In an EBC-1 NSCLC xenograft model, treatment (10 mpk) with the antibody NH-YK resulted in T/C % of 32.9% (p<0.001) (FIG. 4).

Figure 5:
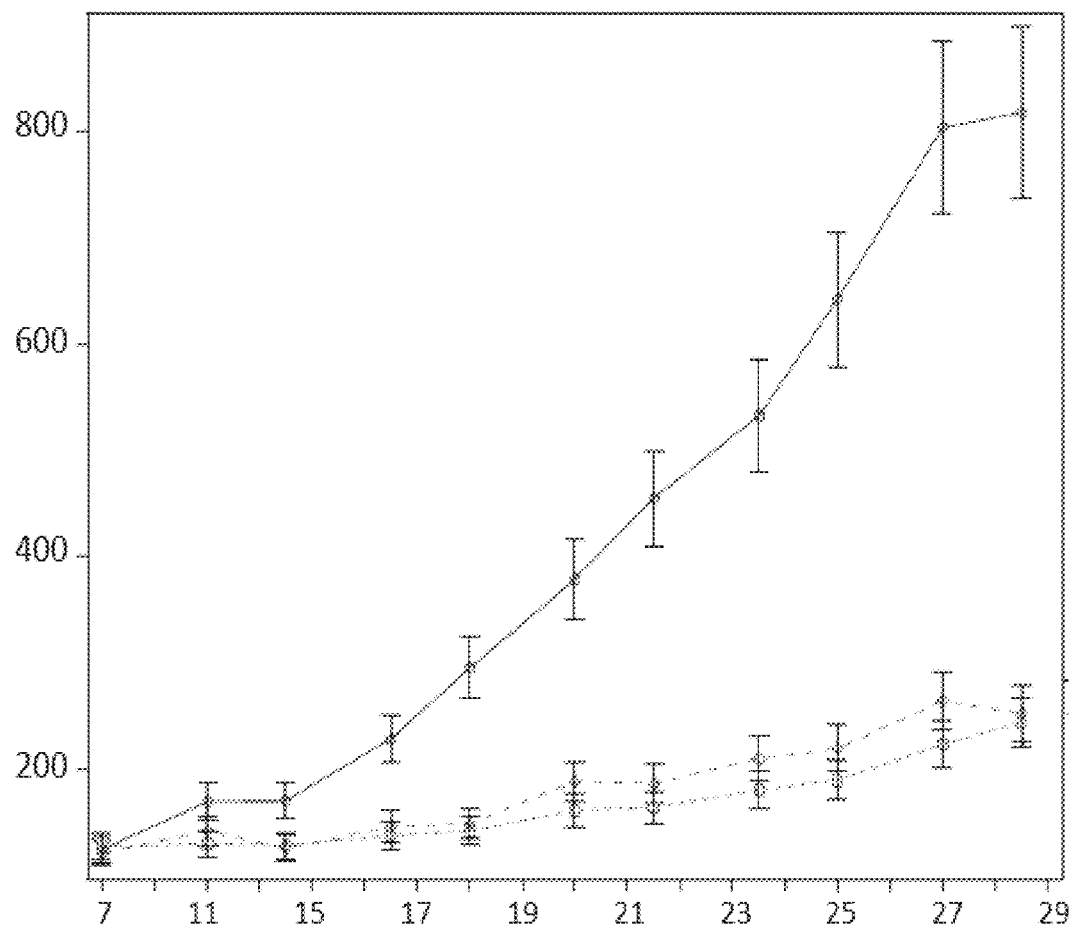
FIG. 5 is a graph showing that administration of the anti-MET/EGFR multifunctional antibody NH-YK results in comparable anti-tumor efficacy as compared to the administration of a combination of the parental MET antibody and cetuximab (T/C %=17.4%, p<0.001 and 18.6%, p<0.001, respectively) or a vehicle control in a MKN45 gastric xenograft model.

Part C: Gastric cancer cell line MKN45 has a high level of MET gene amplification and is very sensitive to MET inhibitors. In a MKN45 gastric xenograft model, the antibody NH-YK showed comparable anti-tumor efficacy to the combination of the parental MET antibody and cetuximab (T/C %=17.4%, p<0.001 and 18.6%, p<0.001, respectively) (FIG. 5).

Part D: In the H1993 NSCLC xenograft model, immunodeficient mice bearing xenografts were treated with either vehicle control, the anti-MET/EGFR multifunctional antibody H9 (4 and 27 mg/kg), anti-MET alone (3 and 20 mg/kg), cetuximab (3 and 20 mg/kg) or the combination of anti-MET plus cetuximab (3 mg/kg and 20 mg/kg of each antibody) once a week for five consecutive weeks. The anti-MET/EGFR multifunctional antibody H9 at 27 mg/kg resulted in significant greater antitumor efficacy than any other treatment (p<0.001) (FIG. 6).

When tested in H441 xenografts, the antibody H9 also showed superior efficacy when compared to individual treatments or the combination of the parental MET antibody and cetuximab (FIG. 7).

Example 11

Inhibition of Tumor Growth in Patient-derived Xenograft (PDX) Models for Colorectal Cancer Patient-derived colorectal carcinoma samples may be procured and tumor fragments derived from an individual patient can be implanted in a single immune-compromised mouse and allowed to grow until it reaches an approximate volume of 100-200 mm$^3$. The antibody NH-YK at 27 mg/kg or vehicle control may be administered once a week for 3-4 consecutive weeks. Tumors may be measured via electronic caliper twice a week. Body weight can also be assessed regularly. The vehicle control group may be treated with phosphate buffered saline (PBS) administered through intraperitoneal (i.p.) injection on a once weekly schedule for four cycles. Tumor volume may be calculated using the formula: $A^2 \times B \times 0.536$, where A is the smaller and B is the larger of perpendicular diameters.

Colorectal carcinoma tumor samples from two patients were individually implanted into two different immunecompromised mice essentially as described above in this Example 11. As shown in Tables 17 and 18, weekly administration of the antibody NH-YK significantly reduced the volume of each of the PDX tumors when compared to vehicle-treated animals harboring PDX tumors.

TABLE 17

| Absolute Tumor Volume (mm$^3$) of PDX (from Patient #1) | Day 0 | Day 25 |
|---|---|---|
| Vehicle | 192.1 | 1186.1 |
| NH-YK | 195.2 | 23.6 |

TABLE 18

| Absolute Tumor Volume (mm$^3$) of PDX (from Patient #2) | Day 0 | Day 21 |
|---|---|---|
| Vehicle | 248.4 | 1141.1 |
| NH-YK | 207.8 | 46.2 |

Example 12

Inhibition of Tumor Growth in Patient-derived Xenograft (PDX) Models for Squamous Cell Carcinoma of the Head and Neck (SCCHN)

Patient-derived squamous cell carcinoma of the head and neck (SCCHN) samples may be procured and tumor fragments derived from an individual patient can be implanted in a single immune-compromised mouse and allowed to grow until it reaches an approximate volume of 100-200 mm$^3$. The antibody NH-YK at 27 mg/kg or vehicle control may be administered twice a week for 4 consecutive weeks. Tumors may be measured via electronic caliper twice a week. Body weight can also be assessed regularly. The vehicle control group may be treated with PBS administered through i.p. injection on a once weekly schedule for four cycles and 20% PEG 400/80% [20% captisol in distilled de-ionized water] administered through oral gavage (p.o.) on a once daily schedule for 28 cycles. Tumor volume may be calculated using the formula: Tumor Volume (mm$^3$)=width$^2 \times$length$\times$0.52.

Squamous cell carcinoma of the head and neck tumor samples from two patients were individually implanted into two different immunecompromised mice essentially as described above in this Example 12. As shown in Table 19, twice weekly administration of the antibody NH-YK significantly reduced the volume of the PDX tumor when compared to a vehicle-treated animal harboring a PDX tumor.

TABLE 19

| Absolute Tumor Volume (mm$^3$) of PDX (from Patient #1) | Day 0 | Day 46 |
|---|---|---|
| Vehicle | 200 | 1221 ± 236 (SEM) |
| NH-YK | 200 | 222 ± 121 (SEM) |

The standard error of the mean (SEM)

Example 13

Inhibition of Tumor Growth in Mouse Xenograft Model for Erlotinib-resistant NSCLC (Erlotinib-resistant HCC-827)

Female athymic nude mice age 6- to 7-weeks old are available commercially, including from Harlan Laboratories. The mice are allowed to acclimate for one week and fed ad libitum on a normal low fat (4.5%) diet, which may be continued for the duration of the study. HCC-827 tumor cells are available for purchase from ATCC and may be cultured in cell culture media such as RPMI 1640 with L-glutamine, 25 mM HEPES supplemented with 10% FBS and 1 mM Na Pyruvate. Cells may be detached, washed with serum free medium and then resuspended at a final concentration of $50 \times 10^6$ cells/mL in serum free RPMI 1640. Viable tumor cells, approximately $5 \times 10^6$, may be subcutaneously implanted in the rear flank of female athymic nude mice in a 1:1 mixture of serum free growth medium and Matrigel. Once tumors are established, the mice may be treated with daily doses of 25 mg/kg erlotinib until resistant tumors start to regrow, even in the presence of erlotinib. Once resistant tumors reach a mean volume of approximately 1000 mm$^3$, they may be excised, divided into 50 mm$^3$ fragments and reimplanted into subject female athmic nude mice. In order to monitor regrowth, tumor and body weight measurements may be performed twice weekly. Once the average tumor volume reached 100 mm$^3$, animals were randomized using a randomization algorithm and divided into treatment groups. Antibodies were diluted in PBS and administered via tail vein injection once a week. In order to assure tumors are erlotinib resistant, animals in the control group received PBS vehicle and 25 mg/kg erlotinib. Tumor volume (mm$^3$) was determined via electronic calipers and may be estimated from the formula $A^2 \times B \times 0.536$, where A is the smaller and B is the larger of perpendicular diameters.

Immunodeficient mice bearing erlotinib-resistant HCC-827 NSCLC xenografts were generated as described above in this Example and treated with either (A) the vehicle plus 25 mg/kg erlotinib (i.e., control group), (B) the combination of 25 mg/kg erlotinib and 27 mg/kg antibody NH-YK, (C) the combination of 25 mg/kg erlotinib and 20 mg/kg cetuximab, (D) the combination of the parental MET antibody dosed at 20 mg/kg and 25 mg/kg erlotinib, or (E) the combination of the parental MET antibody dosed at 20 mg/kg, cetuximab dosed at 20 mg/kg, and 25 mg/kg erlotinib. The combination of antibody NH-YK and erlotinib (i.e., treatment group (B)) resulted in a significant reduction in absolute tumor volume after the same or longer period of time as compared to all of the other treatment groups (Table 20). Thus, tumor growth in mice carrying erlotinib-resistant tumors is significantly reduced upon treatment with the antibody NH-YK in combination with erlotinib, particularly when compared to animals treated with erlotinib combined with PBS vehicle, cetuximab, or the parental MET antibody. The antibody NH-YK in combination with erlotinib (B) also showed superior antitumor efficacy when compared to the combination of erlotinib, cetuximab and the parental MET antibody (E).

TABLE 20

| Treatment Group | Day of Final Measurement | Absolute Tumor Volume (mm$^3$) |
| --- | --- | --- |
| A | 110 | 2587 |
| B | 152 | 304 |
| C | 126 | 2312 |
| D | 126 | 1706 |
| E | 152 | 1172 |

We claim:

1. A multifunctional antibody that binds MET and EGFR comprising:
    (a) two first polypeptides wherein both first polypeptides comprise the amino acid sequence of SEQ ID NO: 25, SEQ ID NO: 26, SEQ ID NO: 27, SEQ ID NO: 29, SEQ ID NO: 31, or SEQ ID NO: 52; and
    (b) two second polypeptides wherein both second polypeptides comprise the amino acid sequence of SEQ ID NO: 33.

2. The multifunctional antibody of claim 1 wherein both first polypeptides comprise the amino acid sequence of SEQ ID NO: 27 or SEQ ID NO: 29.

3. The multifunctional antibody of claim 2 wherein both first polypeptides comprise the amino acid sequence of SEQ ID NO: 27.

4. The multifunctional antibody of claim 2 wherein both first polypeptides comprise the amino acid sequence of SEQ ID NO: 29.

5. The multifunctional antibody of claim 3 wherein the amino acid sequence of both first polypeptides is the amino acid sequence of SEQ ID NO: 27 and the amino acid sequence of both second polypeptides is the amino acid sequence of SEQ ID NO: 33.

6. A pharmaceutical composition, comprising the multifunctional antibody of claim 1, and a pharmaceutically acceptable carrier, diluent, or excipient.

7. A pharmaceutical composition, comprising the multifunctional antibody of claim 4, and a pharmaceutically acceptable carrier, diluent, or excipient.

8. A pharmaceutical composition, comprising the multifunctional antibody of claim 5, and a pharmaceutically acceptable carrier, diluent, or excipient.

* * * * *

SEQUENCE LISTING

```
<160> NUMBER OF SEQ ID NOS: 53

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Gly Phe Ser Leu Thr Asn Tyr Gly Val His
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic construct

<400> SEQUENCE: 2

Val Ile Tyr Ser Gly Gly Asn Thr Asp Tyr Asn Thr Pro Phe Lys Gly
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic construct

<400> SEQUENCE: 3

Ala Arg Ala Leu Asp Tyr Tyr Asp Tyr Asp Phe Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic construct

<400> SEQUENCE: 4

Arg Ala Ser Tyr Ser Ile Gly Thr Asn Ile His
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic construct

<400> SEQUENCE: 5

Arg Tyr Ala Lys Glu Ser Ile Ser
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Gln Gln Asn Asn Ala Trp Pro Thr Thr
1               5

<210> SEQ ID NO 7
<211> LENGTH: 16
<212> TYPE: PRT
<213> ORGANISM: Artificial Sequence
<220> FEATURE:
<223> OTHER INFORMATION: Synthetic construct

<400> SEQUENCE: 7

Val Ile Trp Ser Gly Gly Asn Thr Asp Tyr Asn Thr Pro Phe Thr Gly
1               5                   10                  15

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Tyr Tyr Ala Ser Arg Ser Ile Ser
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa at position 3 = Tyr or Trp
<220> FEATURE:
<221> NAME/KEY: MISC_FEATURE
<222> LOCATION: (15)..(15)
<223> OTHER INFORMATION: Xaa at position 15 = Lys or Thr

<400> SEQUENCE: 9

Val Ile Xaa Ser Gly Gly Asn Thr Asp Tyr Asn Thr Pro Phe Xaa Gly
1               5                   10                  15

<210> SEQ ID NO 10
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa at position 1 = Arg or Tyr
<220> FEATURE:
<221> NAME/KEY: MISC_FEATURE
<222> LOCATION: (4)..(4)
<223> OTHER INFORMATION: Xaa at position 4 = Lys or Ser
<220> FEATURE:
<221> NAME/KEY: MISC_FEATURE
```

```
<222> LOCATION: (5)..(5)
<223> OTHER INFORMATION: Xaa at position 5 = Glu or Arg

<400> SEQUENCE: 10

Xaa Tyr Ala Xaa Xaa Ser Ile Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Gly Tyr Thr Phe Thr Asp Tyr Tyr Met His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic construct

<400> SEQUENCE: 12

Arg Val Asn Pro Asn Arg Arg Gly Thr Thr Tyr Asn Gln Lys Phe Glu
1               5                   10                  15

Gly

<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Ala Arg Ala Asn Trp Leu Asp Tyr
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic construct

<400> SEQUENCE: 14

Ser Val Ser Ser Ser Val Ser Ser Ile Tyr Leu His
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic construct

<400> SEQUENCE: 15

Tyr Ser Thr Ser Asn Leu Ala Ser
1               5

<210> SEQ ID NO 16
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 16

Gln Val Tyr Ser Gly Tyr Pro Leu Thr
1               5

<210> SEQ ID NO 17
<211> LENGTH: 119
<212> TYPE: PRT
<213> ORGANISM: Artificial Sequence
<220> FEATURE:
<223> OTHER INFORMATION: Synthetic construct

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Asn Tyr
                20                  25                  30

Gly Val His Trp Val Arg Gln Ala Pro Gly Gln Cys Leu Glu Trp Met
            35                  40                  45

Gly Val Ile Tyr Ser Gly Gly Asn Thr Asp Tyr Asn Thr Pro Phe Lys
        50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Leu Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic construct

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ala Ser Tyr Ser Ile Gly Thr Asn
                20                  25                  30

Ile His Trp Tyr Gln Gln Lys Pro Gly Gln Pro Pro Lys Leu Leu Ile
            35                  40                  45

Arg Tyr Ala Lys Glu Ser Ile Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asn Asn Ala Trp Pro Thr
                85                  90                  95

Thr Phe Gly Cys Gly Thr Lys Val Glu Ile Lys
            100                 105

<210> SEQ ID NO 19
<211> LENGTH: 119
<212> TYPE: PRT
<213> ORGANISM: Artificial Sequence
```

<220> FEATURE:
<223> OTHER INFORMATION: Synthetic construct

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Asn Tyr
            20                  25                  30

Gly Val His Trp Val Arg Gln Ala Pro Gly Gln Cys Leu Glu Trp Met
        35                  40                  45

Gly Val Ile Trp Ser Gly Gly Asn Thr Asp Tyr Asn Thr Pro Phe Thr
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Leu Val Thr Val Ser Ser
        115
```

<210> SEQ ID NO 20
<211> LENGTH: 107
<212> TYPE: PRT
<213> ORGANISM: Artificial Sequence
<220> FEATURE:
<223> OTHER INFORMATION: Synthetic construct

<400> SEQUENCE: 20

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Tyr Ser Ile Gly Thr Asn
            20                  25                  30

Ile His Trp Tyr Gln Gln Lys Pro Gly Gln Pro Pro Lys Leu Leu Ile
        35                  40                  45

Tyr Tyr Ala Ser Arg Ser Ile Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asn Asn Ala Trp Pro Thr
                85                  90                  95

Thr Phe Gly Cys Gly Thr Lys Val Glu Ile Lys
            100                 105
```

<210> SEQ ID NO 21
<211> LENGTH: 115
<212> TYPE: PRT
<213> ORGANISM: Artificial Sequence
<220> FEATURE:
<223> OTHER INFORMATION: Synthetic construct

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45
```

```
Gly Arg Val Asn Pro Asn Arg Arg Gly Thr Thr Tyr Asn Gln Lys Phe
     50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Ala Asn Trp Leu Asp Tyr Trp Gly Gln Gly Thr Thr Val Thr
                100                 105                 110

Val Ser Ser
        115

<210> SEQ ID NO 22
<211> LENGTH: 108
<212> TYPE: PRT
<213> ORGANISM: Artificial Sequence
<220> FEATURE:
<223> OTHER INFORMATION: Synthetic construct

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Ser Val Ser Ser Val Ser Ser Ile
                 20                  25                  30

Tyr Leu His Trp Tyr Gln Gln Lys Pro Gly Lys Ala Pro Lys Leu Leu
             35                  40                  45

Ile Tyr Ser Thr Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Val Tyr Ser Gly Tyr Pro
                 85                  90                  95

Leu Thr Phe Gly Gly Gly Thr Lys Val Glu Ile Lys
                100                 105

<210> SEQ ID NO 23
<211> LENGTH: 251
<212> TYPE: PRT
<213> ORGANISM: Artificial Sequence
<220> FEATURE:
<223> OTHER INFORMATION: Synthetic construct

<400> SEQUENCE: 23

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Ser Leu Thr Asn Tyr
                 20                  25                  30

Gly Val His Trp Val Arg Gln Ala Pro Gly Gln Cys Leu Glu Trp Met
             35                  40                  45

Gly Val Ile Tyr Ser Gly Gly Asn Thr Asp Tyr Asn Thr Pro Phe Lys
 50                  55                  60

Gly Arg Val Thr Ile Thr Ala Asp Glu Ser Thr Ser Thr Ala Tyr Met
 65                  70                  75                  80

Glu Leu Ser Ser Leu Arg Ser Glu Asp Thr Ala Val Tyr Tyr Cys Ala
                 85                  90                  95

Arg Ala Leu Asp Tyr Tyr Asp Tyr Asp Phe Ala Tyr Trp Gly Gln Gly
                100                 105                 110

Thr Leu Val Thr Val Ser Ser Gly Gly Gly Ser Gly Gly Gly Gly
             115                 120                 125
```

```
Ser Gly Gly Gly Gly Ser Gly Gly Gly Ser Gly Gly Gly Ser
    130                 135                 140

Asp Ile Val Met Thr Gln Ser Pro Asp Ser Leu Ala Val Ser Leu Gly
145                 150                 155                 160

Glu Arg Ala Thr Ile Asn Cys Arg Ala Ser Tyr Ser Ile Gly Thr Asn
                165                 170                 175

Ile His Trp Tyr Gln Gln Lys Pro Gly Gln Pro Pro Lys Leu Leu Ile
            180                 185                 190

Arg Tyr Ala Lys Glu Ser Ile Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Asn Asn Ala Trp Pro Thr
225                 230                 235                 240

Thr Phe Gly Cys Gly Thr Lys Val Glu Ile Lys
                245                 250

<210> SEQ ID NO 24
<211> LENGTH: 251
<212> TYPE: PRT
<213> ORGANISM: Artificial Sequence
<220> FEATURE:
<223> OTHER INFORMATION: Synthetic construct

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Asn Tyr
            20                  25                  30

Gly Val His Trp Val Arg Gln Ala Pro Gly Gln Cys Leu Glu Trp Met
        35                  40                  45

Gly Val Ile Trp Ser Gly Gly Asn Thr Asp Tyr Asn Thr Pro Phe Thr
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Asp Ile Val Met Thr Gln Ser Pro Asp Ser Leu Ala Val Ser Leu Gly
145                 150                 155                 160

Glu Arg Ala Thr Ile Asn Cys Arg Ala Ser Tyr Ser Ile Gly Thr Asn
                165                 170                 175

Ile His Trp Tyr Gln Gln Lys Pro Gly Gln Pro Pro Lys Leu Leu Ile
            180                 185                 190

Tyr Tyr Ala Ser Arg Ser Ile Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Asn Asn Ala Trp Pro Thr
225                 230                 235                 240
```

```
Thr Phe Gly Cys Gly Thr Lys Val Glu Ile Lys
            245                 250

<210> SEQ ID NO 25
<211> LENGTH: 384
<212> TYPE: PRT
<213> ORGANISM: Artificial Sequence
<220> FEATURE:
<223> OTHER INFORMATION: Synthetic construct

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Asn Tyr
            20                  25                  30

Gly Val His Trp Val Arg Gln Ala Pro Gly Gln Cys Leu Glu Trp Met
        35                  40                  45

Gly Val Ile Tyr Ser Gly Gly Asn Thr Asp Tyr Asn Thr Pro Phe Lys
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Asp Ile Val Met Thr Gln Ser Pro Asp Ser Leu Ala Val Ser Leu Gly
145                 150                 155                 160

Glu Arg Ala Thr Ile Asn Cys Arg Ala Ser Tyr Ser Ile Gly Thr Asn
                165                 170                 175

Ile His Trp Tyr Gln Gln Lys Pro Gly Gln Pro Pro Lys Leu Leu Ile
            180                 185                 190

Arg Tyr Ala Lys Glu Ser Ile Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Asn Asn Ala Trp Pro Thr
225                 230                 235                 240

Thr Phe Gly Cys Gly Thr Lys Val Glu Ile Lys Gly Gly Gly Ser Gly
                245                 250                 255

Gly Gly Gly Ser Gly Gly Gly Gly Ser Thr Gly Gln Val Gln
            260                 265                 270

Leu Val Gln Ser Gly Ala Glu Val Lys Lys Pro Gly Ala Ser Val Lys
        275                 280                 285

Val Ser Cys Lys Ala Ser Gly Tyr Thr Phe Thr Asp Tyr Tyr Met His
    290                 295                 300

Trp Val Arg Gln Ala Pro Gly Gln Gly Leu Glu Trp Met Gly Arg Val
305                 310                 315                 320

Asn Pro Asn Arg Arg Gly Thr Thr Tyr Asn Gln Lys Phe Glu Gly Arg
                325                 330                 335

Val Thr Met Thr Thr Asp Thr Ser Thr Ser Thr Ala Tyr Met Glu Leu
            340                 345                 350
```

```
Arg Ser Leu Arg Ser Asp Asp Thr Ala Val Tyr Tyr Cys Ala Arg Ala
            355                 360                 365

Asn Trp Leu Asp Tyr Trp Gly Gln Gly Thr Thr Val Thr Val Ser Ser
    370                 375                 380
```

<210> SEQ ID NO 26
<211> LENGTH: 384
<212> TYPE: PRT
<213> ORGANISM: Artificial Sequence
<220> FEATURE:
<223> OTHER INFORMATION: Synthetic construct

<400> SEQUENCE: 26

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Asn Tyr
            20                  25                  30

Gly Val His Trp Val Arg Gln Ala Pro Gly Gln Cys Leu Glu Trp Met
        35                  40                  45

Gly Val Ile Trp Ser Gly Gly Asn Thr Asp Tyr Asn Thr Pro Phe Thr
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Asp Ile Val Met Thr Gln Ser Pro Asp Ser Leu Ala Val Ser Leu Gly
145                 150                 155                 160

Glu Arg Ala Thr Ile Asn Cys Arg Ala Ser Tyr Ser Ile Gly Thr Asn
                165                 170                 175

Ile His Trp Tyr Gln Gln Lys Pro Gly Gln Pro Pro Lys Leu Leu Ile
            180                 185                 190

Tyr Tyr Ala Ser Arg Ser Ile Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Asn Asn Ala Trp Pro Thr
225                 230                 235                 240

Thr Phe Gly Cys Gly Thr Lys Val Glu Ile Lys Gly Gly Gly Ser Gly
                245                 250                 255

Gly Gly Gly Ser Gly Gly Gly Ser Gly Ser Thr Gly Gln Val Gln
            260                 265                 270

Leu Val Gln Ser Gly Ala Glu Val Lys Lys Pro Gly Ala Ser Val Lys
        275                 280                 285

Val Ser Cys Lys Ala Ser Gly Tyr Thr Phe Thr Asp Tyr Tyr Met His
    290                 295                 300

Trp Val Arg Gln Ala Pro Gly Gln Gly Leu Glu Trp Met Gly Arg Val
305                 310                 315                 320

Asn Pro Asn Arg Arg Gly Thr Thr Tyr Asn Gln Lys Phe Glu Gly Arg
                325                 330                 335
```

```
Val Thr Met Thr Thr Asp Thr Ser Thr Ser Thr Ala Tyr Met Glu Leu
            340                 345                 350

Arg Ser Leu Arg Ser Asp Asp Thr Ala Val Tyr Tyr Cys Ala Arg Ala
        355                 360                 365

Asn Trp Leu Asp Tyr Trp Gly Gln Gly Thr Thr Val Thr Val Ser Ser
    370                 375                 380
```

<210> SEQ ID NO 27
<211> LENGTH: 710
<212> TYPE: PRT
<213> ORGANISM: Artificial Sequence
<220> FEATURE:
<223> OTHER INFORMATION: Synthetic construct

<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Asn Tyr
            20                  25                  30

Gly Val His Trp Val Arg Gln Ala Pro Gly Gln Cys Leu Glu Trp Met
        35                  40                  45

Gly Val Ile Tyr Ser Gly Gly Asn Thr Asp Tyr Asn Thr Pro Phe Lys
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ala Leu Asp Tyr Tyr Asp Tyr Asp Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Asp Ile Val Met Thr Gln Ser Pro Asp Ser Leu Ala Val Ser Leu Gly
145                 150                 155                 160

Glu Arg Ala Thr Ile Asn Cys Arg Ala Ser Tyr Ser Ile Gly Thr Asn
                165                 170                 175

Ile His Trp Tyr Gln Gln Lys Pro Gly Gln Pro Pro Lys Leu Leu Ile
            180                 185                 190

Arg Tyr Ala Lys Glu Ser Ile Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Asn Asn Ala Trp Pro Thr
225                 230                 235                 240

Thr Phe Gly Cys Gly Thr Lys Val Glu Ile Lys Gly Gly Gly Ser Gly
                245                 250                 255

Gly Gly Gly Ser Gly Gly Gly Ser Gly Ser Thr Gly Gln Val Gln
            260                 265                 270

Leu Val Gln Ser Gly Ala Glu Val Lys Lys Pro Gly Ala Ser Val Lys
        275                 280                 285

Val Ser Cys Lys Ala Ser Gly Tyr Thr Phe Thr Asp Tyr Tyr Met His
    290                 295                 300

Trp Val Arg Gln Ala Pro Gly Gln Gly Leu Glu Trp Met Gly Arg Val
305                 310                 315                 320
```

```
Asn Pro Asn Arg Arg Gly Thr Thr Tyr Asn Gln Lys Phe Glu Gly Arg
                325                 330                 335

Val Thr Met Thr Thr Asp Thr Ser Thr Ser Thr Ala Tyr Met Glu Leu
            340                 345                 350

Arg Ser Leu Arg Ser Asp Asp Thr Ala Val Tyr Tyr Cys Ala Arg Ala
            355                 360                 365

Asn Trp Leu Asp Tyr Trp Gly Gln Gly Thr Thr Val Thr Val Ser Ser
        370                 375                 380

Ala Ser Thr Lys Gly Pro Ser Val Phe Pro Leu Ala Pro Cys Ser Arg
385                 390                 395                 400

Ser Thr Ser Glu Ser Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
            435                 440                 445

Leu Ser Ser Val Val Thr Val Pro Ser Ser Ser Leu Gly Thr Lys Thr
    450                 455                 460

Tyr Thr Cys Asn Val Asp His Lys Pro Ser Asn Thr Lys Val Asp Lys
465                 470                 475                 480

Arg Val Glu Ser Lys Tyr Gly Pro Pro Cys Pro Pro Cys Pro Ala Pro
                485                 490                 495

Glu Ala Ala Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
            515                 520                 525

Asp Val Ser Gln Glu Asp Pro Glu Val Gln Phe Asn Trp Tyr Val Asp
    530                 535                 540

Gly Val Glu Val His Asn Ala Lys Thr Lys Pro Arg Glu Glu Gln Phe
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Gly Leu
            580                 585                 590

Pro Ser Ser Ile Glu Lys Thr Ile Ser Lys Ala Lys Gly Gln Pro Arg
            595                 600                 605

Glu Pro Gln Val Tyr Thr Leu Pro Pro Ser Gln Glu Glu Met Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Arg Leu Thr Val Asp Lys Ser Arg Trp Gln Glu Gly Asn Val Phe Ser
            675                 680                 685

Cys Ser Val Met His Glu Ala Leu His Asn His Tyr Thr Gln Lys Ser
    690                 695                 700

Leu Ser Leu Ser Leu Gly
705                 710

<210> SEQ ID NO 28
<211> LENGTH: 2136
```

<212> TYPE: DNA
<213> ORGANISM: Artificial Sequence
<220> FEATURE:
<223> OTHER INFORMATION: Synthetic construct

<400> SEQUENCE: 28

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cttctggttt | ctcattaact | aactatggtg | tacactgggt | gcgacaggcc | 120 |
| cctggacaat | gtcttgagtg | gatgggagtg | atatatagtg | gtggaaacac | agattataat | 180 |
| acacctttca | aaggacgcgt | cacgattacc | gcggacgaat | ccacgagcac | agcctacatg | 240 |
| gagctgagca | gcctgagatc | tgaggacacg | gccgtgtatt | actgtgcgag | agccctcgac | 300 |
| tactatgatt | acgactttgc | ttactggggc | cagggcaccc | tggtcaccgt | ctcctcaggc | 360 |
| ggcggaggct | ctggcggagg | tggtagtggt | ggcggtggat | caggggggagg | cggatctggc | 420 |
| ggtggcggca | gcgacatcgt | gatgacccag | tctccagact | ccctggctgt | gtctctgggc | 480 |
| gagagggcca | ccatcaactg | cagggccagt | tatagtattg | gcacaaacat | acactggtac | 540 |
| cagcagaaac | caggacagcc | tcctaagctg | ctcattagat | atgctaagga | gtctatctct | 600 |
| ggggtccctg | accgattcag | tggcagcggg | tctgggacag | atttcactct | caccatcagc | 660 |
| agcctgcagg | ctgaagatgt | ggcagtttat | tactgtcaac | aaaataacgc | ttggccaacc | 720 |
| acgttcggct | gcgggaccaa | ggtggagatc | aaaggcggag | gatctggggg | aggggggcagc | 780 |
| ggaggcgggg | gctcgggatc | cactggtcag | gttcagctgg | tgcagtctgg | tgctgaggtg | 840 |
| aagaagcctg | gtgcctcagt | gaaggtctcc | tgcaaggctt | ctggttacac | attcactgac | 900 |
| tactacatgc | actgggtgcg | tcaggcccct | ggtcaaggtc | ttgagtggat | gggtcgtgtt | 960 |
| aatcctaacc | ggaggggtac | tacctacaac | cagaaattcg | agggccgtgt | caccatgacc | 1020 |
| acagacacat | ccacgagcac | agcctacatg | gagctgcgta | gcctgcgttc | tgacgacacg | 1080 |
| gccgtgtatt | actgtgcgcg | tgcgaactgg | cttgactact | ggggccaggg | caccaccgtc | 1140 |
| accgtctcct | ccgcctccac | caagggccca | tcggtcttcc | cgctagcgcc | ctgctccagg | 1200 |
| agcacctccg | agagcacagc | cgccctgggc | tgcctggtca | aggactactt | ccccgaaccg | 1260 |
| gtgacggtgt | cgtggaactc | aggcgccctg | accagcggcg | tgcacacctt | cccggctgtc | 1320 |
| ctacagtcct | caggactcta | ctccctcagc | agcgtggtga | ccgtgccctc | cagcagcttg | 1380 |
| ggcacgaaga | cctacacctg | caacgtagat | cacaagccca | gcaacaccaa | ggtggacaag | 1440 |
| agagttgagt | ccaaatatgg | tcccccatgc | ccaccctgcc | cagcacctga | ggccgccggg | 1500 |
| ggaccatcag | tcttcctgtt | ccccccaaaa | cccaaggaca | ctctcatgat | ctcccggacc | 1560 |
| cctgaggtca | cgtgcgtggt | ggtggacgtg | agccaggaag | accccgaggt | ccagttcaac | 1620 |
| tggtacgtga | tggcgtgga | ggtgcataat | gccaagacaa | agccgcggga | ggagcagttc | 1680 |
| aacagcacgt | accgtgtggt | cagcgtcctc | accgtcctgc | accaggactg | gctgaacggc | 1740 |
| aaggagtaca | agtgcaaggt | ctccaacaaa | ggcctcccgt | cctccatcga | gaaaaccatc | 1800 |
| tccaaagcca | aagggcagcc | ccgagagcca | caggtgtaca | ccctgccccc | atcccaggag | 1860 |
| gagatgacca | agaaccaggt | cagcctgacc | tgcctggtca | aaggcttcta | ccccagcgac | 1920 |
| atcgccgtgg | agtgggaaag | caatgggcag | ccggagaaca | actacaagac | cacgcctccc | 1980 |
| gtgctggact | ccgacggctc | cttcttcctc | tacagcaggc | taaccgtgga | caagagcagg | 2040 |
| tggcaggagg | ggaatgtctt | ctcatgctcc | gtgatgcatg | aggctctgca | caaccactac | 2100 |
| acacagaaga | gcctctccct | gtctctgggt | tgatag | | | 2136 |

```
<210> SEQ ID NO 29
<211> LENGTH: 710
<212> TYPE: PRT
<213> ORGANISM: Artificial Sequence
<220> FEATURE:
<223> OTHER INFORMATION: Synthetic construct

<400> SEQUENCE: 29
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Phe | Ser | Leu | Thr | Asn | Tyr |
| | | | 20 | | | | | 25 | | | | | 30 | | |
| Gly | Val | His | Trp | Val | Arg | Gln | Ala | Pro | Gly | Gln | Cys | Leu | Glu | Trp | Met |
| | | 35 | | | | | 40 | | | | | 45 | | | |
| Gly | Val | Ile | Trp | Ser | Gly | Gly | Asn | Thr | Asp | Tyr | Asn | Thr | Pro | Phe | Thr |
| | 50 | | | | | 55 | | | | | 60 | | | | |
| Gly | Arg | Val | Thr | Ile | Thr | Ala | Asp | Glu | Ser | Thr | Ser | Thr | Ala | Tyr | Met |
| 65 | | | | | 70 | | | | | 75 | | | | | 80 |
| Glu | Leu | Ser | Ser | Leu | Arg | Ser | Glu | Asp | Thr | Ala | Val | Tyr | Tyr | Cys | Ala |
| | | | | 85 | | | | | 90 | | | | | 95 | |
| Arg | Ala | Leu | Asp | Tyr | Tyr | Asp | Tyr | Asp | Phe | Ala | Tyr | Trp | Gly | Gln | Gly |
| | | | 100 | | | | | 105 | | | | | 110 | | |
| Thr | Leu | Val | Thr | Val | Ser | Ser | Gly | Gly | Gly | Ser | Gly | Gly | Gly | Gly |
| | | 115 | | | | | 120 | | | | | 125 | | | |
| Ser | Gly | Gly | Gly | Gly | Ser | Gly | Gly | Gly | Ser | Gly | Gly | Gly | Gly | Ser |
| | 130 | | | | | 135 | | | | | 140 | | | | |
| Asp | Ile | Val | Met | Thr | Gln | Ser | Pro | Asp | Ser | Leu | Ala | Val | Ser | Leu | Gly |
| 145 | | | | | 150 | | | | | 155 | | | | | 160 |
| Glu | Arg | Ala | Thr | Ile | Asn | Cys | Arg | Ala | Ser | Tyr | Ser | Ile | Gly | Thr | Asn |
| | | | | 165 | | | | | 170 | | | | | 175 | |
| Ile | His | Trp | Tyr | Gln | Gln | Lys | Pro | Gly | Gln | Pro | Pro | Lys | Leu | Leu | Ile |
| | | | 180 | | | | | 185 | | | | | 190 | | |
| Tyr | Tyr | Ala | Ser | Arg | Ser | Ile | Ser | Gly | Val | Pro | Asp | Arg | Phe | Ser | Gly |
| | | 195 | | | | | 200 | | | | | 205 | | | |
| Ser | Gly | Ser | Gly | Thr | Asp | Phe | Thr | Leu | Thr | Ile | Ser | Ser | Leu | Gln | Ala |
| | 210 | | | | | 215 | | | | | 220 | | | | |
| Glu | Asp | Val | Ala | Val | Tyr | Tyr | Cys | Gln | Gln | Asn | Asn | Ala | Trp | Pro | Thr |
| 225 | | | | | 230 | | | | | 235 | | | | | 240 |
| Thr | Phe | Gly | Cys | Gly | Thr | Lys | Val | Glu | Ile | Lys | Gly | Gly | Gly | Ser | Gly |
| | | | | 245 | | | | | 250 | | | | | 255 | |
| Gly | Gly | Gly | Ser | Gly | Gly | Gly | Gly | Ser | Gly | Ser | Thr | Gly | Gln | Val | Gln |
| | | | 260 | | | | | 265 | | | | | 270 | | |
| Leu | Val | Gln | Ser | Gly | Ala | Glu | Val | Lys | Lys | Pro | Gly | Ala | Ser | Val | Lys |
| | | 275 | | | | | 280 | | | | | 285 | | | |
| Val | Ser | Cys | Lys | Ala | Ser | Gly | Tyr | Thr | Phe | Thr | Asp | Tyr | Tyr | Met | His |
| | 290 | | | | | 295 | | | | | 300 | | | | |
| Trp | Val | Arg | Gln | Ala | Pro | Gly | Gln | Gly | Leu | Glu | Trp | Met | Gly | Arg | Val |
| 305 | | | | | 310 | | | | | 315 | | | | | 320 |
| Asn | Pro | Asn | Arg | Arg | Gly | Thr | Thr | Tyr | Asn | Gln | Lys | Phe | Glu | Gly | Arg |
| | | | | 325 | | | | | 330 | | | | | 335 | |
| Val | Thr | Met | Thr | Thr | Asp | Thr | Ser | Thr | Ser | Thr | Ala | Tyr | Met | Glu | Leu |
| | | | 340 | | | | | 345 | | | | | 350 | | |
| Arg | Ser | Leu | Arg | Ser | Asp | Asp | Thr | Ala | Val | Tyr | Tyr | Cys | Ala | Arg | Ala |
| | | 355 | | | | | 360 | | | | | 365 | | | |

Asn Trp Leu Asp Tyr Trp Gly Gln Gly Thr Thr Val Thr Val Ser Ser
370                 375                 380

Ala Ser Thr Lys Gly Pro Ser Val Phe Pro Leu Ala Pro Cys Ser Arg
385                 390                 395                 400

Ser Thr Ser Glu Ser Thr Ala Ala Leu Gly Cys Leu Val Lys Asp Tyr
            405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Lys Thr
450                 455                 460

Tyr Thr Cys Asn Val Asp His Lys Pro Ser Asn Thr Lys Val Asp Lys
465                 470                 475                 480

Arg Val Glu Ser Lys Tyr Gly Pro Pro Cys Pro Pro Cys Pro Ala Pro
            485                 490                 495

Glu Ala Ala Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser Gln Glu Asp Pro Glu Val Gln Phe Asn Trp Tyr Val Asp
530                 535                 540

Gly Val Glu Val His Asn Ala Lys Thr Lys Pro Arg Glu Glu Gln Phe
545                 550                 555                 560

Asn Ser Thr Tyr Arg Val Val Ser Val Leu Thr Val Leu His Gln Asp
            565                 570                 575

Trp Leu Asn Gly Lys Glu Tyr Lys Cys Lys Val Ser Asn Lys Gly Leu
            580                 585                 590

Pro Ser Ser Ile Glu Lys Thr Ile Ser Lys Ala Lys Gly Gln Pro Arg
        595                 600                 605

Glu Pro Gln Val Tyr Thr Leu Pro Pro Ser Gln Glu Glu Met Thr Lys
610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
            645                 650                 655

Thr Thr Pro Pro Val Leu Asp Ser Asp Gly Ser Phe Phe Leu Tyr Ser
            660                 665                 670

Arg Leu Thr Val Asp Lys Ser Arg Trp Gln Glu Gly Asn Val Phe Ser
        675                 680                 685

Cys Ser Val Met His Glu Ala Leu His Asn His Tyr Thr Gln Lys Ser
690                 695                 700

Leu Ser Leu Ser Leu Gly
705                 710

<210> SEQ ID NO 30
<211> LENGTH: 2136
<212> TYPE: DNA
<213> ORGANISM: Artificial Sequence
<220> FEATURE:
<223> OTHER INFORMATION: Synthetic construct

<400> SEQUENCE: 30
caggtgcagc tggtgcagtc tggggctgag gtgaagaagc ctgggtcctc ggtgaaggtc        60
tcctgcaagg cttctggttt ctcattaact aactatggtg tacactgggt gcgacaggcc       120

```
cctggacaat gtcttgagtg gatgggagtg atatggagtg gtggaaacac agattataat    180
acacctttca caggacgcgt cacgattacc gcggacgaat ccacgagcac agcctacatg    240
gagctgagca gcctgagatc tgaggacacg gccgtgtatt actgtgcgag agccctcgac    300
tactatgatt acgactttgc ttactggggc cagggcaccc tggtcaccgt ctcctcaggc    360
ggcggaggct ctggcggagg tggtagtggt ggcggtggat caggggggagg cggatctggc    420 ggtggcggca gcgacatcgt gatgacccag tctccagact ccctggctgt gtctctgggc    480
gagagggcca ccatcaactg cagggccagt tatagtattg cacaaacat acactggtac    540 cagcagaaac aggacagcc tcctaagctg ctcatttact atgcttctcg gtctatctct    600
ggggtccctg accgattcag tggcagcggg tctgggacag atttcactct caccatcagc    660
agcctgcagg ctgaagatgt ggcagtttat tactgtcaac aaaataacgc ttggccaacc    720
acgttcggct gcgggaccaa ggtggagatc aaaggcggag gatctggggg aggggggcagc    780 ggaggcgggg gctcgggatc cactggtcag gttcagctgg tgcagtctgg tgctgaggtg    840
aagaagcctg gtgcctcagt gaaggtctcc tgcaaggctt ctggttacac attcactgac    900
tactacatgc actgggtgcg tcaggcccct ggtcaaggtc ttgagtggat gggtcgtgtt    960
aatcctaacc ggagggggtac tacctacaac cagaaattcg agggccgtgt caccatgacc    1020
acagacacat ccacgagcac agcctacatg gagctgcgta gcctgcgttc tgacgacacg    1080
gccgtgtatt actgtgcgcg tgcgaactgg cttgactact ggggccaggg caccaccgtc    1140
accgtctcct ccgcctccac caagggccca tcggtcttcc cgctagcgcc ctgctccagg    1200
agcacctccg agagcacagc cgccctgggc tgcctggtca aggactactt ccccgaaccg    1260
gtgacggtgt cgtggaactc aggcgccctg accagcggcg tgcacacctt cccggctgtc    1320
ctacagtcct caggactcta ctccctcagc agcgtggtga ccgtgccctc cagcagcttg    1380
ggcacgaaga cctacacctg caacgtagat cacaagccca gcaacaccaa ggtggacaag    1440
agagttgagt ccaaatatgg tcccccatgc ccaccctgcc cagcacctga gccgccgggg    1500
ggaccatcag tcttcctgtt cccccccaaaa cccaaggaca ctctcatgat ctcccggacc    1560
cctgaggtca cgtgcgtggt ggtggacgtg agccaggaag acccccgaggt ccagttcaac    1620 tggtacgtgg atggcgtgga ggtgcataat gccaagacaa agccgcggga ggagcagttc    1680
aacagcacgt accgtgtggt cagcgtcctc accgtcctgc accaggactg gctgaacggc    1740
aaggagtaca agtgcaaggt ctccaacaaa ggcctcccgt cctccatcga gaaaaccatc    1800
tccaaagcca aagggcagcc ccgagagcca caggtgtaca cctgccccc atcccaggag    1860 gagatgacca gaaccaggt cagcctgacc tgcctggtca aaggcttcta ccccagcgac    1920
atcgccgtgg agtgggaaag caatgggcag ccggagaaca actacaagac cacgcctccc    1980
gtgctggact ccgacggctc cttcttcctc tacagcaggc taaccgtgga caagagcagg    2040
tggcaggagg ggaatgtctt ctcatgctcc gtgatgcatg aggctctgca caaccactac    2100
acacagaaga gcctctccct gtctctgggt tgatag    2136
```

<210> SEQ ID NO 31
<211> LENGTH: 706
<212> TYPE: PRT
<213> ORGANISM: Artificial Sequence
<220> FEATURE:
<223> OTHER INFORMATION: Synthetic construct

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
    275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
```

```
            420                 425                 430
Gln Lys Ser Leu Ser Leu Ser Leu Gly Gly Gly Ser Gly Gly Gly
            435                 440                 445
Gly Ser Gly Gly Gly Ser Gln Val Gln Leu Val Gln Ser Gly Ala
            450                 455                 460
Glu Val Lys Lys Pro Gly Ser Ser Val Lys Val Ser Cys Lys Ala Ser
465                 470                 475                 480
Gly Phe Ser Leu Thr Asn Tyr Gly Val His Trp Val Arg Gln Ala Pro
                    485                 490                 495
Gly Gln Cys Leu Glu Trp Met Gly Val Ile Tyr Ser Gly Gly Asn Thr
                    500                 505                 510
Asp Tyr Asn Thr Pro Phe Lys Gly Arg Val Thr Ile Thr Ala Asp Glu
                    515                 520                 525
Ser Thr Ser Thr Ala Tyr Met Glu Leu Ser Ser Leu Arg Ser Glu Asp
                    530                 535                 540
Thr Ala Val Tyr Tyr Cys Ala Arg Ala Leu Asp Tyr Tyr Asp Tyr Asp
545                 550                 555                 560
Phe Ala Tyr Trp Gly Gln Gly Thr Leu Val Thr Val Ser Ser Gly Gly
                    565                 570                 575
Gly Gly Ser Gly Gly Gly Ser Gly Gly Gly Ser Gly Gly Gly
                    580                 585                 590
Gly Ser Gly Gly Gly Ser Asp Ile Val Met Thr Gln Ser Pro Asp
                    595                 600                 605
Ser Leu Ala Val Ser Leu Gly Glu Arg Ala Thr Ile Asn Cys Arg Ala
                    610                 615                 620
Ser Tyr Ser Ile Gly Thr Asn Ile His Trp Tyr Gln Gln Lys Pro Gly
625                 630                 635                 640
Gln Pro Pro Lys Leu Leu Ile Arg Tyr Ala Lys Glu Ser Ile Ser Gly
                    645                 650                 655
Val Pro Asp Arg Phe Ser Gly Ser Gly Ser Gly Thr Asp Phe Thr Leu
                    660                 665                 670
Thr Ile Ser Ser Leu Gln Ala Glu Asp Val Ala Val Tyr Tyr Cys Gln
                    675                 680                 685
Gln Asn Asn Ala Trp Pro Thr Thr Phe Gly Cys Gly Thr Lys Val Glu
            690                 695                 700
Ile Lys
705

<210> SEQ ID NO 32
<211> LENGTH: 2124
<212> TYPE: DNA
<213> ORGANISM: Artificial Sequence
<220> FEATURE:
<223> OTHER INFORMATION: Synthetic construct

<400> SEQUENCE: 32
caggttcagc tggtgcagtc tggtgctgag gtgaagaagc tggtgcctc agtgaaggtc      60 tcctgcaagg cttctggtta cacattcact gactactaca tgcactgggt gcgtcaggcc     120
cctggtcaag tcttgagtg gatgggtcgt gttaatccta accggagggg tactacctac     180
aaccagaaat cgagggccg tgtcaccatg accagagaca tccacgag cacagcctac        240 atggagctgc gtagcctgcg ttctgacgac acgccgtgt attactgtgc gcgtgcgaac      300
tggcttgact actggggcca gggcaccacc gtcaccgtct cctccgcctc caccaagggc     360
ccatcggtct tccccgctag cgccctgctc caggagcacct ccgagagcac agccgccctg   420
```

```
ggctgcctgg tcaaggacta cttccccgaa ccggtgacgg tgtcgtggaa ctcaggcgcc      480
ctgaccagcg gcgtgcacac cttccgggct gtcctacagt cctcaggact ctactccctc      540
agcagcgtgg tgaccgtgcc ctccagcagc ttgggcacga agacctacac ctgcaacgta      600
gatcacaagc ccagcaacac caaggtggac aagagagttg agtccaaata tggtccccca      660
tgcccaccct gcccagcacc tgaggccgcc ggggaccat cagtcttcct gttcccccca       720
aaacccaagg acactctcat gatctcccgg accccctgagg tcacgtgcgt ggtggtggac      780
gtgagccagg aagacccga ggtccagttc aactggtacg tggatggcgt ggaggtgcat       840
aatgccaaga caaagccgcg ggaggagcag ttcaacagca cgtaccgtgt ggtcagcgtc      900
ctcaccgtcc tgcaccagga ctggctgaac ggcaaggagt acaagtgcaa ggtctccaac     960
aaaggcctcc cgtcctccat cgagaaaacc atctccaaag ccaaggggca gccccgagag     1020
ccacaggtgt acaccctgcc cccatcccag gaggagatga ccaagaacca ggtcagcctg     1080
acctgcctgg tcaaaggctt ctaccccagc gacatcgccg tggagtggga aagcaatggg     1140
cagccggaga caactacaa gaccacgcct cccgtgctgg actccgacgg ctccttcttc       1200
ctctacagca ggctaaccgt ggacaagagc aggtggcagg agggggatgt cttctcatgc     1260
tccgtgatgc atgaggctct gcacaaccac tacacacaga agagcctctc cctgtctctg     1320
ggtggcggag gctccggggg aggggtagc ggaggagggg gatcccaggt gcagctggtg       1380
cagtctgggg ctgaggtgaa gaagcctggg tcctcggtga aggtctcctg caaggcttct     1440
gggttcctcat taactaacta tggtgtacac tgggtgcgac aggcccctgg acaatgtctt    1500
gagtggatgg gagtgatata tagtggtgga aacacagatt ataatacacc tttcaaagga    1560
cgcgtcacga ttaccgcgga cgaatccacg agcacagcct acatggagct gagcagcctg    1620
agatctgagg acacggccgt gtattactgt gcgagagccc tcgactacta tgattacgac     1680
tttgcttact ggggccaggg caccctggtc accgtctcct caggcggcgg aggctctggc    1740
ggaggtggta gtggtggcgg tggatcaggg ggaggcggat ctggcggtgg cggcagcgac    1800
atcgtgatga cccagtctcc agactccctg gctgtgtctc tgggcgagag gccaccatc    1860
aactgcaggg ccagttatag tattggcaca aacatacact ggtaccagca gaaaccagga    1920
cagcctccta agctgctcat tagatatgct aaggagtcta tctctggggt ccctgaccga    1980
ttcagtggca gcgggtctgg gacagatttc actctcacca tcagcagcct gcaggctgaa    2040
gatgtggcag tttattactg tcaacaaaat aacgcttggc caaccacgtt cggctgcggg    2100
accaaggtgg agatcaaata atag                                           2124
```

<210> SEQ ID NO 33
<211> LENGTH: 215
<212> TYPE: PRT
<213> ORGANISM: Artificial Sequence
<220> FEATURE:
<223> OTHER INFORMATION: Synthetic construct

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
```

-continued

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 34
<211> LENGTH: 651
<212> TYPE: DNA
<213> ORGANISM: Artificial Sequence
<220> FEATURE:
<223> OTHER INFORMATION: Synthetic construct

<400> SEQUENCE: 34
gacatccaga tgacccagtc tccatcctcc ctgtctgcat ctgtaggaga cagagtcacc      60
atcacttgca gtgtcagctc aagtgtatcc tccatttact gcactggtta tcagcagaaa     120
ccagggaaag cccctaagct cctgatctat agcacatcca acttggcttc tggagtccca     180
tcaaggttca gtggcagtgg atctgggaca gatttcactc tcaccatcag cagtctgcaa     240
cctgaagatt ttgcaactta ctactgtcaa gtctacagtg gttacccgct cacgttcggc     300
ggagggacca aggtggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgctaata g              651

<210> SEQ ID NO 35
<211> LENGTH: 932
<212> TYPE: PRT
<213> ORGANISM: Homo sapiens

<400> SEQUENCE: 35

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala

```
            35                  40                  45
Glu Thr Pro Ile Gln Asn Val Ile Leu His Glu His His Ile Phe Leu
 50                  55                  60
Gly Ala Thr Asn Tyr Ile Tyr Val Leu Asn Glu Glu Asp Leu Gln Lys
 65                  70                  75                  80
Val Ala Glu Tyr Lys Thr Gly Pro Val Leu Glu His Pro Asp Cys Phe
                 85                  90                  95
Pro Cys Gln Asp Cys Ser Ser Lys Ala Asn Leu Ser Gly Gly Val Trp
                100                 105                 110
Lys Asp Asn Ile Asn Met Ala Leu Val Val Asp Thr Tyr Tyr Asp Asp
                115                 120                 125
Gln Leu Ile Ser Cys Gly Ser Val Asn Arg Gly Thr Cys Gln Arg His
                130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                165                 170                 175
Val Ser Ala Leu Gly Ala Lys Val Leu Ser Ser Val Lys Asp Arg Phe
                180                 185                 190
Ile Asn Phe Phe Val Gly Asn Thr Ile Asn Ser Ser Tyr Phe Pro Asp
                195                 200                 205
His Pro Leu His Ser Ile Ser Val Arg Arg Leu Lys Glu Thr Lys Asp
                210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
                260                 265                 270
Thr Phe His Thr Arg Ile Ile Arg Phe Cys Ser Ile Asn Ser Gly Leu
                275                 280                 285
His Ser Tyr Met Glu Met Pro Leu Glu Cys Ile Leu Thr Glu Lys Arg
                290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
                355                 360                 365
Tyr Val Asn Asp Phe Phe Asn Lys Ile Val Asn Lys Asn Asn Val Arg
                370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
                435                 440                 445
Asp Leu Thr Ile Ala Asn Leu Gly Thr Ser Glu Gly Arg Phe Met Gln
450                 455                 460
```

```
Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880
```

```
Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr
        930

<210> SEQ ID NO 36
<211> LENGTH: 908
<212> TYPE: PRT
<213> ORGANISM: Homo sapiens

<400> SEQUENCE: 36

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320
```

```
Val Phe Ala Gln Ser Lys Pro Asp Ser Ala Glu Pro Met Asp Arg Ser
            325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
            355                 360                 365

Asn His Glu His Cys Phe Asn Arg Thr Leu Leu Arg Asn Ser Ser Gly
            370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
                420                 425                 430

Thr Ser Glu Gly Arg Phe Met Gln Val Val Ser Arg Ser Gly Pro
            435                 440                 445

Ser Thr Pro His Val Asn Phe Leu Leu Asp Ser His Pro Val Ser Pro
            450                 455                 460

Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
                500                 505                 510

Gln Cys Gly Trp Cys His Asp Lys Cys Val Arg Ser Glu Glu Cys Leu
                515                 520                 525

Ser Gly Thr Trp Thr Gln Gln Ile Cys Leu Pro Ala Ile Tyr Lys Val
            530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
            595                 600                 605

His Phe Asn Met Ser Ile Ile Ile Ser Asn Gly His Gly Thr Thr Gln
610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
            690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735
```

```
Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
        755                 760                 765

Arg Ser Asn Ser Glu Ile Ile Cys Cys Thr Thr Pro Ser Leu Gln Gln
770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
            805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
            850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
            885                 890                 895

Gly Lys Val Ile Val Gln Pro Asp Gln Asn Phe Thr
            900                 905

<210> SEQ ID NO 37
<211> LENGTH: 283
<212> TYPE: PRT
<213> ORGANISM: Homo sapiens

<400> SEQUENCE: 37

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
            85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
            115                 120                 125

Asp Ile Gln Ser Glu Val His Cys Ile Phe Ser Pro Gln Ile Glu Glu
            130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
            165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
            195                 200                 205
```

-continued

Ser Tyr Ile Asp Val Leu Pro Glu Phe Arg Asp Ser Tyr Pro Ile Lys
210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
        245                 250                 255

Phe Cys Ser Ile Asn Ser Gly Leu His Ser Tyr Met Glu Met Pro Leu
        260                 265                 270

Glu Cys Ile Leu Thr Glu Lys Arg Lys Lys Arg
        275                 280

<210> SEQ ID NO 38
<211> LENGTH: 212
<212> TYPE: PRT
<213> ORGANISM: Homo sapiens

<400> SEQUENCE: 38

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
            20                  25                  30

Asp Ile Leu Phe Gly Val Phe Ala Gln Ser Lys Pro Asp Ser Ala Glu
        35                  40                  45

Pro Met Asp Arg Ser Ala Met Cys Ala Phe Pro Ile Lys Tyr Val Asn
    50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
            100                 105                 110

Phe Thr Thr Ala Leu Gln Arg Val Asp Leu Phe Met Gly Gln Phe Ser
        115                 120                 125

Glu Val Leu Leu Thr Ser Ile Ser Thr Phe Ile Lys Gly Asp Leu Thr
    130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Thr Leu Asn Gln Asn
            180                 185                 190

Gly Tyr Thr Leu Val Ile Thr Gly Lys Lys Ile Thr Lys Ile Pro Leu
        195                 200                 205

Asn Gly Leu Gly
    210

<210> SEQ ID NO 39
<211> LENGTH: 10
<212> TYPE: PRT
<213> ORGANISM: Homo sapiens

<400> SEQUENCE: 39

Val Val Asp Thr Tyr Tyr Asp Asp Gln Leu
1               5                   10

<210> SEQ ID NO 40

```
<211> LENGTH: 26
<212> TYPE: PRT
<213> ORGANISM: Homo sapiens

<400> SEQUENCE: 40

Ile Ser Cys Gly Ser Val Asn Arg Gly Thr Cys Gln Arg His Val Phe
1               5                   10                  15

Pro His Asn His Thr Ala Asp Ile Gln Ser
            20                  25

<210> SEQ ID NO 41
<211> LENGTH: 17
<212> TYPE: PRT
<213> ORGANISM: Homo sapiens

<400> SEQUENCE: 41

Ala Leu Gly Ala Lys Val Leu Ser Ser Val Lys Asp Arg Phe Ile Asn
1               5                   10                  15

Phe

<210> SEQ ID NO 42
<211> LENGTH: 12
<212> TYPE: PRT
<213> ORGANISM: Homo sapiens

<400> SEQUENCE: 42

Val Arg Arg Leu Lys Glu Thr Lys Asp Gly Phe Met
1               5                   10

<210> SEQ ID NO 43
<211> LENGTH: 6
<212> TYPE: PRT
<213> ORGANISM: Homo sapiens

<400> SEQUENCE: 43

Asp Thr Tyr Tyr Asp Asp
1               5

<210> SEQ ID NO 44
<211> LENGTH: 13
<212> TYPE: PRT
<213> ORGANISM: Homo sapiens

<400> SEQUENCE: 44

His Val Phe Pro His Asn His Thr Ala Asp Ile Gln Ser
1               5                   10

<210> SEQ ID NO 45
<211> LENGTH: 4
<212> TYPE: PRT
<213> ORGANISM: Homo sapiens

<400> SEQUENCE: 45

Phe Ile Asn Phe
1

<210> SEQ ID NO 46
<211> LENGTH: 8
<212> TYPE: PRT
<213> ORGANISM: Homo sapiens

<400> SEQUENCE: 46

Lys Glu Thr Lys Asp Gly Phe Met
1               5
```

```
<210> SEQ ID NO 47
<211> LENGTH: 10
<212> TYPE: PRT
<213> ORGANISM: Artificial Sequence
<220> FEATURE:
<223> OTHER INFORMATION: Synthetic construct

<400> SEQUENCE: 47

Gly Gly Gly Gly Ser Gly Gly Gly Gly Ser
1               5                   10

<210> SEQ ID NO 48
<211> LENGTH: 15
<212> TYPE: PRT
<213> ORGANISM: Artificial Sequence
<220> FEATURE:
<223> OTHER INFORMATION: Synthetic construct

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 20
<212> TYPE: PRT
<213> ORGANISM: Artificial Sequence
<220> FEATURE:
<223> OTHER INFORMATION: Synthetic construct

<400> SEQUENCE: 49

Gly Gly Gly Gly Ser Gly Gly Gly Gly Ser Gly Gly Gly Gly Ser Gly
1               5                   10                  15

Gly Gly Gly Ser
            20

<210> SEQ ID NO 50
<211> LENGTH: 25
<212> TYPE: PRT
<213> ORGANISM: Artificial Sequence
<220> FEATURE:
<223> OTHER INFORMATION: Synthetic construct

<400> SEQUENCE: 50

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 51
<211> LENGTH: 18
<212> TYPE: PRT
<213> ORGANISM: Artificial Sequence
<220> FEATURE:
<223> OTHER INFORMATION: Synthetic construct

<400> SEQUENCE: 51

Gly Gly Gly Ser Gly Gly Gly Gly Ser Gly Gly Gly Gly Ser Gly Ser
1               5                   10                  15

Thr Gly

<210> SEQ ID NO 52
<211> LENGTH: 706
<212> TYPE: PRT
<213> ORGANISM: Artificial Sequence
```

<220> FEATURE:
<223> OTHER INFORMATION: Synthetic construct

<400> SEQUENCE: 52

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asp | Tyr |
| | | | 20 | | | | | 25 | | | | | 30 | | |
| Tyr | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Arg | Val | Asn | Pro | Asn | Arg | Arg | Gly | Thr | Thr | Tyr | Asn | Gln | Lys | Phe |
| | 50 | | | | | 55 | | | | | 60 | | | | |
| Glu | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Ala | Asn | Trp | Leu | Asp | Tyr | Trp | Gly | Gln | Gly | Thr | Thr | Val | Thr |
| | | | 100 | | | | | 105 | | | | | 110 | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Cys | Ser | Arg | Ser | Thr | Ser | Glu | Ser | Thr | Ala | Ala | Leu | Gly | Cys | Leu | Val |
| | 130 | | | | | 135 | | | | | 140 | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |
| Thr | Lys | Thr | Tyr | Thr | Cys | Asn | Val | Asp | His | Lys | Pro | Ser | Asn | Thr | Lys |
| | | 195 | | | | | 200 | | | | | 205 | | | |
| Val | Asp | Lys | Arg | Val | Glu | Ser | Lys | Tyr | Gly | Pro | Pro | Cys | Pro | Pro | Cys |
| 210 | | | | | 215 | | | | | 220 | | | | | |
| Pro | Ala | Pro | Glu | Ala | Ala | Gly | Gly | Pro | Ser | Val | Phe | Leu | Phe | Pro | Pro |
| 225 | | | | | 230 | | | | | 235 | | | | | 240 |
| Lys | Pro | Lys | Asp | Thr | Leu | Met | Ile | Ser | Arg | Thr | Pro | Glu | Val | Thr | Cys |
| | | | | 245 | | | | | 250 | | | | | 255 | |
| Val | Val | Val | Asp | Val | Ser | Gln | Glu | Asp | Pro | Glu | Val | Gln | Phe | Asn | Trp |
| | | | 260 | | | | | 265 | | | | | 270 | | |
| Tyr | Val | Asp | Gly | Val | Glu | Val | His | Asn | Ala | Lys | Thr | Lys | Pro | Arg | Glu |
| | | 275 | | | | | 280 | | | | | 285 | | | |
| Glu | Gln | Phe | Asn | Ser | Thr | Tyr | Arg | Val | Val | Ser | Val | Leu | Thr | Val | Leu |
| | 290 | | | | | 295 | | | | | 300 | | | | |
| His | Gln | Asp | Trp | Leu | Asn | Gly | Lys | Glu | Tyr | Lys | Cys | Lys | Val | Ser | Asn |
| 305 | | | | | 310 | | | | | 315 | | | | | 320 |
| Lys | Gly | Leu | Pro | Ser | Ser | Ile | Glu | Lys | Thr | Ile | Ser | Lys | Ala | Lys | Gly |
| | | | | 325 | | | | | 330 | | | | | 335 | |
| Gln | Pro | Arg | Glu | Pro | Gln | Val | Tyr | Thr | Leu | Pro | Pro | Ser | Gln | Glu | Glu |
| | | | 340 | | | | | 345 | | | | | 350 | | |
| Met | Thr | Lys | Asn | Gln | Val | Ser | Leu | Thr | Cys | Leu | Val | Lys | Gly | Phe | Tyr |
| | | 355 | | | | | 360 | | | | | 365 | | | |
| Pro | Ser | Asp | Ile | Ala | Val | Glu | Trp | Glu | Ser | Asn | Gly | Gln | Pro | Glu | Asn |
| | 370 | | | | | 375 | | | | | 380 | | | | |
| Asn | Tyr | Lys | Thr | Thr | Pro | Pro | Val | Leu | Asp | Ser | Asp | Gly | Ser | Phe | Phe |
| 385 | | | | | 390 | | | | | 395 | | | | | 400 |

```
Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Gly Gly Gly Ser Gly Gly Gly
        435                 440                 445

Gly Ser Gly Gly Gly Ser Gln Val Gln Leu Val Gln Ser Gly Ala
450                 455                 460

Glu Val Lys Lys Pro Gly Ser Ser Val Lys Val Ser Cys Lys Ala Ser
465                 470                 475                 480

Gly Phe Ser Leu Thr Asn Tyr Gly Val His Trp Val Arg Gln Ala Pro
            485                 490                 495

Gly Gln Cys Leu Glu Trp Met Gly Val Ile Trp Ser Gly Gly Asn Thr
            500                 505                 510

Asp Tyr Asn Thr Pro Phe Thr Gly Arg Val Thr Ile Thr Ala Asp Glu
            515                 520                 525

Ser Thr Ser Thr Ala Tyr Met Glu Leu Ser Ser Leu Arg Ser Glu Asp
        530                 535                 540

Thr Ala Val Tyr Tyr Cys Ala Arg Ala Leu Asp Tyr Tyr Asp Tyr Asp
545                 550                 555                 560

Phe Ala Tyr Trp Gly Gln Gly Thr Leu Val Thr Val Ser Ser Gly Gly
            565                 570                 575

Gly Gly Ser Gly Gly Gly Gly Ser Gly Gly Gly Gly Ser Gly Gly Gly
            580                 585                 590

Gly Ser Gly Gly Gly Gly Ser Asp Ile Val Met Thr Gln Ser Pro Asp
            595                 600                 605

Ser Leu Ala Val Ser Leu Gly Glu Arg Ala Thr Ile Asn Cys Arg Ala
610                 615                 620

Ser Tyr Ser Ile Gly Thr Asn Ile His Trp Tyr Gln Gln Lys Pro Gly
625                 630                 635                 640

Gln Pro Pro Lys Leu Leu Ile Tyr Tyr Ala Ser Arg Ser Ile Ser Gly
            645                 650                 655

Val Pro Asp Arg Phe Ser Gly Ser Gly Ser Gly Thr Asp Phe Thr Leu
            660                 665                 670

Thr Ile Ser Ser Leu Gln Ala Glu Asp Val Ala Val Tyr Tyr Cys Gln
            675                 680                 685

Gln Asn Asn Ala Trp Pro Thr Thr Phe Gly Cys Gly Thr Lys Val Glu
        690                 695                 700

Ile Lys
705

<210> SEQ ID NO 53
<211> LENGTH: 441
<212> TYPE: PRT
<213> ORGANISM: Artificial Sequence
<220> FEATURE:
<223> OTHER INFORMATION: Synthetic construct

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45
```

```
Gly Arg Val Asn Pro Asn Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440
```